US010654902B2

(12) United States Patent
Scott et al.

(10) Patent No.: US 10,654,902 B2
(45) Date of Patent: May 19, 2020

(54) METHODS AND COMPOSITIONS FOR THE DISPLAY OF POLYPEPTIDES ON THE PILI OF GRAM-POSITIVE BACTERIA

(71) Applicant: EMORY UNIVERSITY, Atlanta, GA (US)

(72) Inventors: June R. Scott, Atlanta, GA (US); Dorothea Zähner, Atlanta, GA (US); Bernard Quigley, Atlanta, GA (US)

(73) Assignee: Emory University, Atlanta, GA (US)

( * ) Notice: Subject to any disclaimer, the term of this patent is extended or adjusted under 35 U.S.C. 154(b) by 302 days.

(21) Appl. No.: 14/513,797

(22) Filed: Oct. 14, 2014

(65) Prior Publication Data

US 2016/0304567 A1    Oct. 20, 2016

Related U.S. Application Data

(63) Continuation of application No. 12/990,264, filed as application No. PCT/US2009/043286 on May 8, 2009, now abandoned.

(60) Provisional application No. 61/126,883, filed on May 8, 2008, provisional application No. 61/088,250, filed on Aug. 12, 2008.

(51) Int. Cl.
| | |
|---|---|
| *A61K 35/12* | (2015.01) |
| *A61K 39/00* | (2006.01) |
| *C07K 14/315* | (2006.01) |
| *C12N 15/74* | (2006.01) |
| *A61K 39/108* | (2006.01) |
| *A61K 39/07* | (2006.01) |
| *C12N 15/62* | (2006.01) |
| *A61K 39/09* | (2006.01) |
| *C12P 21/02* | (2006.01) |
| *C07K 14/245* | (2006.01) |
| *C12N 9/52* | (2006.01) |

(52) U.S. Cl.
CPC ........ *C07K 14/315* (2013.01); *A61K 39/0258* (2013.01); *A61K 39/07* (2013.01); *A61K 39/09* (2013.01); *A61K 39/092* (2013.01); *C07K 14/245* (2013.01); *C12N 9/52* (2013.01); *C12N 15/62* (2013.01); *C12N 15/746* (2013.01); *C12P 21/02* (2013.01); *C12Y 304/22* (2013.01); *A61K 35/12* (2013.01); *A61K 39/00* (2013.01); *A61K 2039/523* (2013.01); *A61K 2039/6068* (2013.01); *C07K 2319/02* (2013.01); *C07K 2319/035* (2013.01); *C07K 2319/35* (2013.01)

(58) Field of Classification Search
CPC .... A61K 35/12; A61K 39/00; A61K 39/0258; A61K 39/07; A61K 39/09; A61K 39/092; A61K 2039/6068; A61K 2039/523; C07K 14/315; C07K 2319/35; C07K 14/245; C07K 2319/02; C07K 2319/035; C12N 15/746; C12N 9/52; C12N 15/62; C12Y 304/22; C12P 21/02
See application file for complete search history.

(56) References Cited

U.S. PATENT DOCUMENTS

| | | | |
|---|---|---|---|
| 6,913,750 B2 | 6/2005 | Hultgren | |
| 9,861,693 B2 | 1/2018 | Amara | |
| 2008/0026988 A1 | 1/2008 | Baker | |
| 2011/0189236 A1 | 8/2011 | Scott | |
| 2018/0125967 A1 | 5/2018 | Amara | |

FOREIGN PATENT DOCUMENTS

| | | |
|---|---|---|
| WO | 2009027768 | 3/2009 |
| WO | WO 2009/027768 A2 * | 3/2009 |
| WO | 2009137763 | 11/2009 |

OTHER PUBLICATIONS

Chen, Mucosal and Systemic Immune Responses to Chimeric Fimbriae Expressed by *Salmonella enterica* Serovar Typhimurium Vaccine Strains, Infection and Immunity, 2000, p. 3129-3139, 68(6).
Dramsi et al.,Covalent attachmentof proteins to peptidoglycan, FEMS Microbiol Rev 32 (2008) 307-320.
Mandlik et al. Pili in Gram-positive bacteria: assembly, involvement in colonization and biofilm development Trends Microbiol. Jan. 2008; 16(1): 33-40.
PCT Search Report, 2009/137763.
Quigley et al., Linkage of T3 and Cpa pilins in the *Streptococcus pyogenes* M3 pilus, Molecular Microbiology (2009) 72(6), 1379-1394.
Quigley et al., A Foreign Protein Incorporated on the Tip of T3 Pili in Lactococcus lactis Elicits Systemic and Mucosal Immunity, Infection and Immunity, 2010, p. 1294-1303, 78(3).
Scott & Barnett Surface Proteins of Gram-Positive Bacteria and How They Get There, Annu. Rev. Microbiol. 2006. 60:397-423.

(Continued)

*Primary Examiner* — Gary B Nickol
*Assistant Examiner* — Lakia J Jackson-Tongue
(74) *Attorney, Agent, or Firm* — Emory Patent Group

(57) ABSTRACT

Provided herein are methods and compositions for the display of polypeptides of interest on the tip of pili of Gram-positive bacteria. According to the present invention, the polypeptide of interest is amino terminal to a Gram-positive bacterial pilus tip protein or an active variant or fragment thereof, wherein the active variant or fragment comprises a cleaved cell wall sorting signal (CWSS) motif. The Gram-positive bacterium displaying a polypeptide of interest on the tip of pili that are disclosed herein are useful, for example, in methods for immunizing a subject with an antigen and methods for removing contaminants from a composition.

9 Claims, 17 Drawing Sheets
Specification includes a Sequence Listing.

(56) References Cited

OTHER PUBLICATIONS

Shi et al., (English Abstract) Progress on lactococcus lactis expressing heterologous antigens as live mucosal vaccines Wei Sheng Wu Xue Bao. 2006, 46(4):680-3.

Starks et al. Assembly of CS1 Pili: the Role of Specific Residues of the Major Pilin, CooA, Journal of Bacteriology, 2006, p. 231-239.

Zahner & Scott SipA Is Required for Pilus Formation in *Streptococcus pyogenes* Serotype M3, Journal of Bacteriology, 2008, vol. 190, No. 2, p. 527-535.

Buccato et al., Use of Lactococcus lactis Expressing Pili from Group B *Streptococcus* as a Broad-Coverage Vaccine against Streptococcal Disease, JID, 2006, 194:331-340.

Scott, J. R. and Zahner, D. (2006), Pili with strong attachments: Gram-positive bacteria do it differently. Molecular Microbiology, 62: 320-330.

Aggarwal et al. Augmentation of HIV-1 Subtype C Vaccine Constructs Induced Immune Response in Mice by CpG Motif 1826-ODN, Viral Immunol. 2005, 18(1):213-23.

Bahey-El-Din et al. "Lactococcus lactis-based vaccines: Current status and future perspectives" Human Vaccines, 7 (1): 106-109. 2011.

Brenchley et al. "CD4+ T cell depletion during all stages of HIV disease occurs predominantly in the gastrointestinal tract" J Exp Med., 2004; 200(6): 749-759.

Chamcha et al. Oral immunization with a recombinant Lactococcus lactis expressing HIV-1 Gag on the tip of the pilus induces strong mucosal immune responses, Retrovirology, 2012; 9(Suppl 2): O12.

Chamcha et al. "Oral Immunization with a Recombinant Lactococcus lactis—Expressing HIV-1 Antigen on Group A Streptococcus Pilus Induces Strong Mucosal Immunity in the Gut" J Immunol, 2015; 195: 5025-5034.

Goepfert et al. "Phase 1 Safety and Immunogenicity Testing of DNA and Recombinant Modified Vaccinia Ankara Vaccines Expressing HIV-1 Virus-like Particles" The Journal of Infectious Diseases, 2011; 203: 610-619.

Kajikawa et al. "Dissimilar Properties of Two Recombinant Lactobacillus acidophilus Strains Displaying Salmonella FliC with Different Anchoring Motifs" Appl. Environ. Microbiol., 2011; 77(18): 6587-6596.

Kajikawa et al. "Construction and immunological evaluation of dual cell surface display of HIV-1 gag and *Salmonella enterica* serovar Typhimurium FliC in Lactobacillus acidophilus for vaccine delivery" Clin Vaccine Immunol., 2012; 19 (9): 1374-1381.

Kintu et al. "Feasibility and Safety of ALVAC-HIV vCP1521 Vaccine in HIV-Exposed Infants in Uganda: Results From the First HIV Vaccine Trial in Infants in Africa" Acquir Immune Defic Syndr; 2013; 63(1): 1-8.

Lei et al. "Evaluation of oral immunization with recombinant avian influenza virus HA1 displayed on the Lactococcus lactis surface and combined with the mucosal adjuvant cholera toxin subunit B" Clin Vaccine Immunol., 2011; (7): 1046-1051.

Li et al. "Peak SIV replication in resting memory CD4+ T cells depletes gut lamina propria CD4+ T cells" Nature, 2005; 434(7037): 1148-1152.

MacGregor et al. Plasmid vaccination of stable HIV-positive subjects on antiviral treatment results in enhanced CD8 T-cell immunity and increased control of viral "blips", Vaccine 23 (2005) 2066-2073.

Mattapallil et al. "Massive infection and loss of memory CD4+ T cells in multiple tissues during acute SIV Infection" Nature, 2005; 434(7037): 1093-1097.

Pillai et al. "Different Patterns of Expansion, Contraction and Memory Differentiation of HIV-1 Gag-Specific CD8 T Cells Elicited by Adenovirus Type 5 and Modified Vaccinia Ankara Vaccines" Vaccine, 2011; 29(33): 5399-5406.

Pino et al. Cellular Mechanisms of the Adjuvant Activity of the Flagellin Component FljB of *Salmonella enterica* Serovar Typhimurium to Potentiate Mucosal and Systemic Responses, Infection and Immunity, Oct. 2005, vol. 73, No. 10., p. 6763-6770.

Rerks-Ngarm et al. "Vaccination with ALVAC and AIDSVAX to Prevent HIV-1 Infection in Thailand" N Engl J Med, 2009; 361: 2209-2220.

Santra et al. Recombinant poxvirus boosting of DNA-primed rhesus monkeys augments peak but not memory T lymphocyte responses, Proc Natl Acad Sci U S A. 2004, 101(30):11088-93.

Ton-That et al. Assembly of pili on the surface of Corynebacterium diphtheriae, Molecular Microbiology (2003) 50 (4), 1429-1438.

Ton-That et al. Protein sorting to the cell wall envelope of Gram-positive bacteria, Biochimica et Biophysica Acta 1694 (2004) 269-278.

Veazey et al. "Gastrointestinal tract as a major site of CD4+ T cell depletion and viral replication in SIV infection" Science, 1998; 280(5362): 427-431.

Xin et al. "Immunogenicity and protective efficacy of orally administered recombinant Lactococcus lactis expressing surface-bound HIV Env" Blood, 2003; 102: 223-228.

Zahner et al. SipA is Required for Pilus Formation in *Streptococcus pyogenes* Serotype M3, Journal of Bacteriology, 2008, vol. 190, No. 2, p. 527-535.

\* cited by examiner

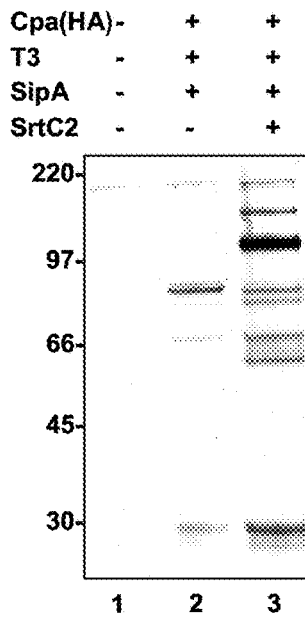

FIG. 2A

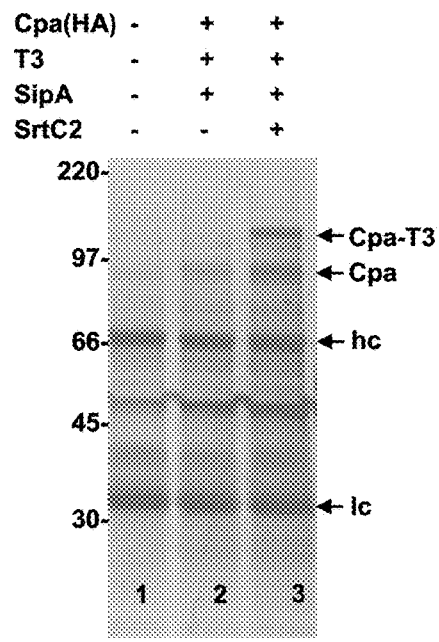

FIG. 2B

```
              SP                              K43
  1 MKKNKLLLATAILATALGTASLNQNVKAETAGVSENAKLIVKKTFDSYTD

51 NEVLMPKADYTFKVEADSTASGKTKDGLEIKPGIVNGLTEQIISYTNTDK

101 PDSKVKSTEFDFSKVVFPGIGVYRYTVSEKQGDVEGITYDTKKWTVDVYV
                            K173          K191
151 GNKEGGGFEPKFIVSKEQGTDVKKPVNFNNSFATTSLKVKKNVSGNTGEL

201 QKEFDFTLTLNESTNFKKDQIVSLQKGNEKFEVKIGTPYKFKLKNGESIQ

251 LDKLPVGITYKVNEMEANKDGYKTTASLKEGDGQSKMYQLDMEQKTDESA    SEQ ID NO: 7

301 DEIVVTNKRDTQVPTGVVGTLAPFAVLSIVAIGGVIYITKRKKA
                       CWSS
```

FIG. 2C

```
                          K43                                                K81
M3_MGAS315    29  ETAGVSENAKLIVKKTFDSYTDNEVLMPKADYTFKVEADSTAS--GKTKDGLEIKPGIVN  86
M1_SF370      22  HGETVVNGAKLTVTKNLDLVNSN-ALIPNTDFTFKIEPDTTVN--------EDGNKFKG---VA  72
M28_MGAS6180  29  ETAGVSENAKLIVKKTFDSYTDNEVLMPKADYTFKVEADSSAT--DKTKDGLEIKPGVTE  86
emmstD33_D633 29  ETAGVTNGTQLTIKKTIANYNDSEVLMPKATFTFEVKPDNSVTGVEKTVDGLTIKAGIAE  88
M49_591       29  ETAGVIDGSTLVVKKTFPSYTDDNVLMPKADYSFKVEADDNAK---GKTKDGLDIKPGVID  86
M18_MGAS8232  29  ETAGVIDGSTLVVKKTFPSYTDDKVLMPKADYTFKVEADDNAK--GKTKDGLDIKPGVID  86
emm33_29487   29  ETAGVVTGKTLPITKSMI-YTDNEILMPKTTFTFTIEPDTTAS--GKTKDGLEIKSGETT  85
M5_Manfredo   29  ETAGVVTGKSLQVTKTMT-YDDEEVLMPETAFTFTIEPDMTAS---GK-EGSLDIKNGIVE 84
M12_A735      29  ETAGVVSSGQLTIKKSITNFNDDTLLMPKTDYTFSVNPDSAAT---GTESNLPIKPGIAV  85

K100    K106                      K129
M3_MGAS315    87  GLT-EQIISYTNTDKPDSKVKSTEFDFSKVVFPGIGVYRYTVSEK-QGDVEGITYDTKKW  144
M1_SF370      73  LNTPMTKVTYTNSDKGGSNTKTAEFDFSEVTFEKPGVYYYKVTEEKIDKVPGVSYDTTSY  133
M28_MGAS6180  87  GLTTEQTIAYDNSVKPSDKSKTATFDFSTVKFPEVGVYRYTVSEI-DSKVSGIKYDTKTW  145
emmstD33_D633 89  GLVKTGNVEYSNTDKVENKDKTTTFDFSTVKFPEVGVYRYTVSET-DSKVSGIKYDTKTW  147
M49_591       87  GLENTKTIRYSNSDKITAKEKSVNFEFANVKFPGVGVYRYTVSAEV-NGNKAGITYDSQQW  145
M18_MGAS8232  87  GLENTKTIHYGNSDKTTAKEKSVNFDFANVKFPGVGVYRYTVSEV-NGNKAGIAYDSQQW  145
emm33_29487   86  GLTTKAIVSYDNTDKESAKNKTSNFNFETVTFSGIGIYRYTVSEQ-NDGIEGIQYDKKW   144
M5_Manfredo   85  GLDKQVTVKYKNTDKTSQKTKIAQFDFSKVKFPAIGVYRYMVSEK-NDKKDGITYDDKKW  143
M12_A735      86  NNQ-DIKVSYSNTDKTSGKEKQVVVDFMKVTFPSVGIYRYVVTEN-KGTAEGVTYDDTKW  143

N180    K191
M3_MGAS315    145 TVDVYVGNKEGG---GFEPKFIVSKEQGTDVKPVNFNNSFATTSLKVKKNVSGNTGELQK  202
M1_SF370      134 TVQVHVLWNEEQQ-KPVATYIVGYKEGS---VPIQFPKNSLDSTTLTVKKKVSGTGGDRSK  190
M28_MGAS6180  146 IVDVYVVNDGNG---GFKARYIVSKEKGQNDKPVVFENSFKTTSLKVEKQVTGNTGELKK  203
emmstD33_D633 148 IVDVYVVNDGNG---GFKAQYIVSKEKGQNDKPVVFENSFKTTSLKVEKQVTGNTGELKK  205
M49_591       146 TVDVYVVNKEGG--GFEVKYIVSTEVGQSEKPVVFKNSFDTTSLKIEKQVTGNTGEHQR  203
M18_MGAS8232  146 TVDVYVVNREDG--GFEAKYIVSTEGGQSDKPVLFKNFFDTTSLKVTKKVTGNTGEHQR  203
emm33_29487   145 TVDVYVGNKEGG---GFEPKYVVSKEVNSDVKPIRFENSFKTTSLKIEKQVTGNTGELQK  202
M5_Manfredo   144 TVDVYVGNKANNEEGFEVLYIVSKEGTSSTKPIEFTNSIKTTSLKIEKQITGNAGDRKK  203
M12_A735      144 LVDVYVGNNEKG--GLEPKYIVSKKGDSATEPIQFNNSFETTSLKIEKEVTGNTGDHKK  201

M3_MGAS315    203 EFDFTLTLNESTNFKKDQIVSLQKGNE------KFEVKIGTPYKFKLKNGESIQLDKLPV  256
M1_SF370      191 DFNFGLTLKANQYYKASEKVMIEKTTKGGQAPVQTEASIDQLYHFTLKDGESIKVTNLPV  250
M28_MGAS6180  204 DFNFTLTINPNDNFVAGQVIKLEKGGI------KADVKIGEPYKFALKNGEKVTLSKLPV  257
emmstD33_D633 206 DFNFTLTINPNDNFVAGQVIKLEKGGI------KADVKIGEPYKFALKNGEKVTLSKLPV  259
M49_591       204 LFSFTLLLTPNECFEKGQVVNILQGGE------TKKVVIGEEYSFTLKDKESVTLSQLPV  257
M18_MGAS8232  204 SFSFTLLLTPNECFEKGQVVNILQGGE------TKKVVIGEEYSFTLKDKESVTLSQLPV  257
emm33_29487   203 DFNFTLILEASALYEKGQVVNLEKGGE------TKDVKIGQEYKFTLHDHQSIMLAKLPI  256
M5_Manfredo   204 SFNFTLTLQPSEYYKTGSVVKIEQDGS------KKDVTIGTPYKFTLGHGKSVMLSKLPI  257
M12_A735      202 AFTFTLTLQPNEYYEASSVVKIEENGQ------TKDVKIGEAYKFTLNDSQSVILSKLPV  255

E264                                 N307
M3_MGAS315    257 GITYKVNKMEANKDGYKTTASLKE-GDGQSKMYQLDM-EQKTDESADEIVVTNKRDTQVP  314
M1_SF370      251 GVDYVVTEDDYKSEKYTTNVEVSPQDGAVKNIAGNSTEQETSTDKDMTITFTNKKDFEVP  310
M28_MGAS6180  258 GVTYSIIEDEADKDGYTTNAKITD-GTAAPVEYKLGN-QQLADESADEIVVTNNRDTQVP  315
emmstD33_D633 260 GITYSIIEDDAGKDGYKTTAILKD-GEQS-STYELGK-NQKTDESADEIVVTNNRDTQVP  316
M49_591       258 GIEYKLTEEDVTKDGYKTSATLKD-GEQS-STYELGK-DHKTDKSADEIVVTNKRDTQVP  314
M18_MGAS8232  258 GIEYKVTEEDVTKDGYKTSATLKD-GDVT-DGYNLGD-SKTTDKSTDEIVVTNKRDTQVP  314
emm33_29487   257 GISYKLTEDKA--DGYTTTATLKE-GEIDAKEYVLGN-LQKTDESADEIVVTNKRDTQVP  312
M5_Manfredo   258 GINYYLSEDEANKDGYTTTATLKEQGKEKSSDFTLSTQNQKTDESADEIVVTNKRDTQVP  317
M12_A735      256 GINYKVEEAEANQGGYTTTATLKD--GEKLSTYNLGQ-EHKTDKTADEIVVTNNRDTQVP  312

M3_MGAS315    315 TG  316  SEQ ID NO 36
M1_SF370      311 TG  312  SEQ ID NO 37
M28_MGAS6180  316 TG  317  SEQ ID NO 38
emmstD33_D633 317 TG  318  SEQ ID NO 39
M49_591       315 TG  316  SEQ ID NO 40
M18_MGAS8232  315 TG  316  SEQ ID NO 41
emm33_29487   312 TG  313  SEQ ID NO 42
M5_Manfredo   318 TG  319  SEQ ID NO 43
M12_A735      313 TG  314  SEQ ID NO 44
```

FIG. 5

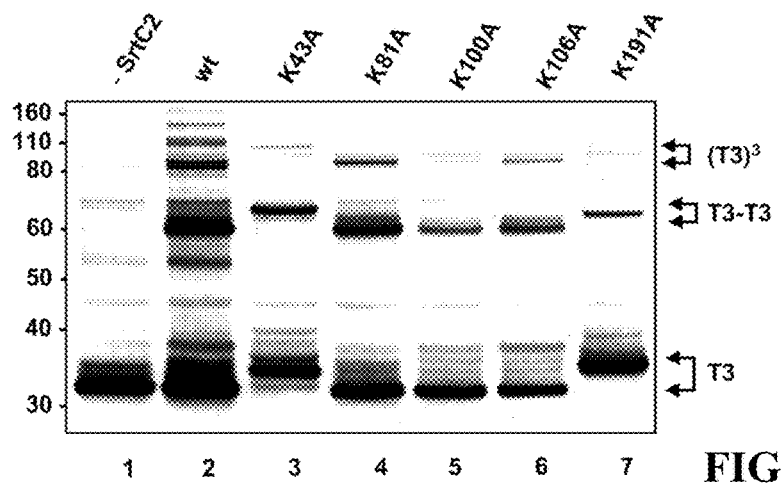
FIG. 6A
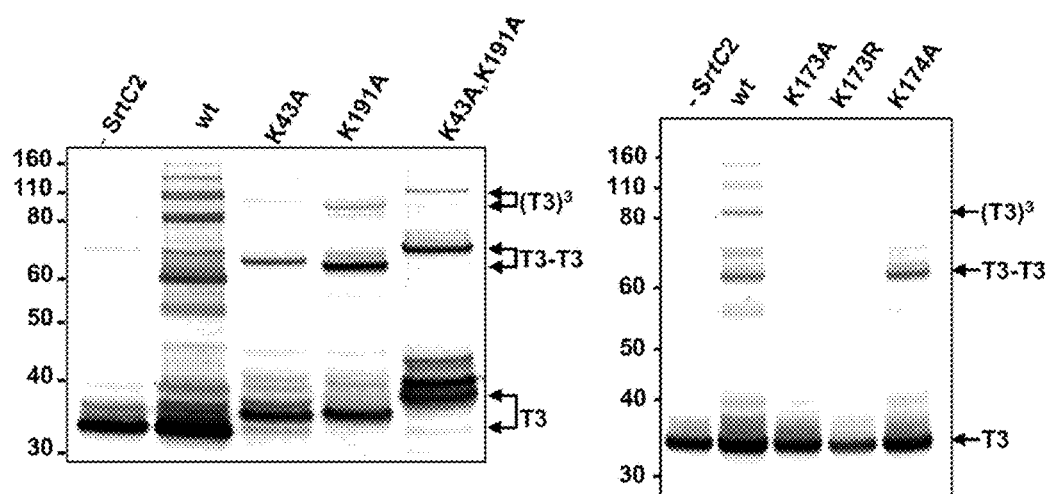
FIG. 6B
FIG. 6C

SEQUENCE LISTING

```
<160> NUMBER OF SEQ ID NOS: 103

<210> SEQ ID NO 1
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Where X is any Amino Acid

<400> SEQUENCE: 1

Leu Pro Xaa Thr Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic construct

<400> SEQUENCE: 2

Leu Pro Ser Thr Gly
1               5

<210> SEQ ID NO 3
<211> LENGTH: 747
<212> TYPE: PRT
<213> ORGANISM: Streptococcus pyogenes

<400> SEQUENCE: 3

Met Gln Lys Arg Asp Lys Thr Asn Tyr Gly Lys Ser Ala Asn Asn Lys
```

-continued

```
1               5                   10                  15
Arg Arg Gln Thr Thr Ile Gly Leu Leu Lys Val Phe Leu Thr Phe Val
                20                  25                  30

Ala Leu Ile Gly Ile Val Gly Phe Ser Ile Arg Ala Phe Gly Ala Glu
                35                  40                  45

Glu Gln Ser Val Pro Asn Lys Gln Ser Ser Val Gln Asp Tyr Pro Trp
    50                  55                  60

Tyr Gly Tyr Asp Ser Tyr Ser Lys Gly Tyr Pro Asp Tyr Ser Pro Leu
65                  70                  75                  80

Lys Thr Tyr His Asn Leu Lys Val Asn Leu Asp Gly Lys Ser Lys Glu
                85                  90                  95

Tyr Gln Ala Tyr Cys Phe Asn Leu Thr Lys His Phe Pro Ser Lys Ser
                100                 105                 110

Asp Ser Val Arg Ser Gln Trp Tyr Lys Lys Leu Glu Gly Thr Asn Glu
                115                 120                 125

Asn Phe Ile Lys Leu Ala Asp Lys Pro Arg Ile Glu Asp Gly Gln Leu
130                 135                 140

Gln Gln Asn Ile Leu Arg Ile Leu Tyr Asn Gly Tyr Pro Asn Asp Arg
145                 150                 155                 160

Asn Gly Ile Met Lys Gly Ile Asp Pro Leu Asn Ala Ile Leu Val Thr
                165                 170                 175

Gln Asn Ala Ile Trp Tyr Tyr Thr Asp Ser Ser Tyr Ile Ser Asp Thr
                180                 185                 190

Ser Lys Ala Phe Gln Gln Glu Thr Asp Leu Lys Leu Asp Ser Gln
                195                 200                 205

Gln Leu Gln Leu Met Arg Asn Ala Leu Lys Arg Leu Ile Asn Pro Lys
    210                 215                 220

Glu Val Glu Ser Leu Pro Asn Gln Val Pro Ala Asn Tyr Gln Leu Ser
225                 230                 235                 240

Ile Phe Gln Ser Ser Asp Lys Thr Phe Gln Asn Leu Leu Ser Ala Glu
                245                 250                 255

Tyr Val Pro Asp Thr Pro Lys Pro Gly Glu Glu Pro Ala Lys
                260                 265                 270

Thr Glu Lys Thr Ser Val Ile Ile Arg Lys Tyr Ala Glu Gly Asp Tyr
                275                 280                 285

Ser Lys Leu Leu Glu Gly Ala Thr Leu Lys Leu Ala Gln Ile Glu Gly
    290                 295                 300

Lys Ser Gly Phe Gln Glu Lys Ile Phe Asp Ser Asn Lys Ser Gly Glu
305                 310                 315                 320

Lys Val Glu Leu Pro Asn Gly Thr Tyr Val Leu Ser Glu Leu Lys Pro
                325                 330                 335

Pro Gln Gly Tyr Gly Val Ala Thr Pro Ile Thr Phe Lys Val Ala Ala
                340                 345                 350

Glu Lys Val Leu Ile Lys Asn Lys Glu Gly Gln Phe Val Glu Asn Gln
                355                 360                 365

Asn Lys Glu Ile Ala Glu Pro Tyr Ser Val Thr Ala Phe Asn Asp Phe
    370                 375                 380

Glu Glu Ile Gly Tyr Leu Ser Asp Phe Asn Asn Tyr Gly Lys Phe Tyr
385                 390                 395                 400

Tyr Ala Lys Asn Thr Asn Gly Thr Asn Gln Val Val Tyr Cys Phe Asn
                405                 410                 415

Ala Asp Leu His Ser Pro Pro Asp Ser Tyr Asp His Gly Ala Asn Ile
                420                 425                 430
```

-continued

Asp Pro Asp Val Ser Glu Ser Lys Glu Ile Lys Tyr Thr His Val Ser
         435                 440                 445

Gly Tyr Asp Leu Tyr Lys Tyr Ala Ala Thr Pro Arg Asp Lys Asp Ala
    450                 455                 460

Asp Phe Phe Leu Lys His Ile Lys Lys Ile Leu Asp Lys Gly Tyr Lys
465                 470                 475                 480

Lys Lys Gly Asp Thr Tyr Lys Thr Leu Thr Glu Ala Gln Phe Arg Ala
            485                 490                 495

Ala Thr Gln Leu Ala Ile Tyr Tyr Thr Asp Ser Ala Asp Leu Thr
            500                 505             510

Thr Leu Lys Thr Tyr Asn Asp Asn Lys Gly Tyr His Gly Phe Asp Lys
        515                 520                 525

Leu Asp Asp Ala Thr Leu Ala Val Val His Glu Leu Ile Thr Tyr Ala
    530                 535                 540

Glu Asp Val Thr Leu Pro Met Thr Gln Asn Leu Asp Phe Phe Val Pro
545                 550                 555                 560

Asn Ser Ser Arg Tyr Gln Ala Leu Ile Gly Thr Gln Tyr His Pro Asn
                565                 570                 575

Glu Leu Ile Asp Val Ile Ser Met Glu Asp Lys Gln Ala Pro Ile Ile
            580                 585                 590

Pro Ile Thr His Lys Leu Thr Ile Ser Lys Thr Val Thr Gly Thr Ile
            595                 600                 605

Ala Asp Lys Lys Lys Glu Phe Asn Phe Glu Ile His Leu Lys Ser Ser
    610                 615                 620

Asp Gly Gln Ala Ile Ser Gly Thr Tyr Pro Thr Asn Ser Gly Glu Leu
625                 630                 635                 640

Thr Val Thr Asp Gly Lys Ala Thr Phe Thr Leu Lys Asp Gly Glu Ser
                645                 650                 655

Leu Ile Val Glu Gly Leu Pro Ser Gly Tyr Ser Tyr Glu Ile Thr Glu
            660                 665                 670

Thr Gly Ala Ser Asp Tyr Glu Val Ser Val Asn Gly Lys Asn Ala Pro
        675                 680                 685

Asp Gly Lys Ala Thr Lys Ala Ser Val Lys Glu Asp Glu Thr Val Ala
    690                 695                 700

Phe Glu Asn Arg Lys Asp Leu Val Pro Pro Thr Gly Leu Thr Asp
705                 710                 715                 720

Gly Ala Ile Tyr Leu Trp Leu Leu Leu Val Pro Phe Gly Leu Leu
                725                 730                 735

Val Trp Leu Phe Gly Arg Lys Gly Thr Lys Lys
            740                 745

<210> SEQ ID NO 4
<211> LENGTH: 2187
<212> TYPE: PRT
<213> ORGANISM: Streptococcus pyogenes

<400> SEQUENCE: 4

Ala Thr Gly Cys Ala Ala Ala Gly Ala Gly Gly Ala Thr Ala
1               5                   10                  15

Ala Ala Ala Cys Cys Ala Thr Thr Ala Thr Gly Gly Ala Ala Gly
            20                  25                  30

Cys Gly Cys Thr Ala Ala Cys Ala Ala Cys Ala Ala Cys Gly Ala
        35                  40                  45

Cys Gly Ala Cys Ala Ala Ala Cys Gly Ala Cys Gly Ala Thr Cys Gly

-continued

```
    50                  55                  60

Gly Ala Thr Thr Ala Cys Thr Gly Ala Ala Ala Gly Thr Ala Thr Thr
65                  70                  75                  80

Thr Thr Thr Gly Ala Cys Gly Thr Thr Thr Gly Thr Ala Gly Cys Thr
                85                  90                  95

Cys Thr Gly Ala Thr Ala Gly Gly Ala Ala Thr Ala Gly Thr Ala Gly
            100                 105                 110

Gly Gly Thr Thr Thr Thr Cys Thr Ala Thr Cys Ala Gly Ala Gly Cys
        115                 120                 125

Gly Thr Thr Cys Gly Gly Ala Gly Cys Thr Gly Ala Ala Gly Ala Ala
    130                 135                 140

Gly Gly Cys Thr Ala Thr Gly Ala Thr Thr Cys Thr Thr Ala Thr Thr
145                 150                 155                 160

Cys Thr Ala Ala Ala Gly Gly Cys Thr Ala Cys Cys Cys Ala Gly Ala
                165                 170                 175

Cys Thr Ala Thr Ala Gly Thr Cys Cys Gly Thr Thr Ala Ala Ala Gly
            180                 185                 190

Ala Cys Thr Thr Ala Cys Cys Ala Thr Ala Ala Thr Thr Thr Ala Ala
        195                 200                 205

Ala Ala Gly Thr Ala Ala Ala Thr Thr Thr Ala Gly Ala Thr Gly Gly
    210                 215                 220

Ala Ala Gly Thr Ala Ala Gly Gly Ala Gly Thr Ala Thr Cys Ala Ala
225                 230                 235                 240

Gly Cys Ala Thr Ala Cys Thr Gly Cys Thr Thr Thr Ala Ala Thr Thr
                245                 250                 255

Thr Ala Ala Cys Ala Ala Ala Ala Cys Ala Cys Thr Thr Thr Cys Cys
            260                 265                 270

Ala Thr Cys Cys Ala Ala Gly Thr Cys Ala Gly Ala Thr Ala Gly Thr
        275                 280                 285

Gly Thr Thr Ala Gly Ala Thr Cys Ala Cys Ala Ala Thr Gly Gly Thr
    290                 295                 300

Ala Thr Ala Ala Ala Ala Ala Ala Cys Thr Thr Gly Ala Ala Gly Gly
305                 310                 315                 320

Ala Ala Cys Thr Ala Ala Thr Gly Ala Ala Ala Ala Cys Thr Thr Thr
                325                 330                 335

Ala Thr Cys Ala Ala Gly Thr Thr Ala Gly Cys Ala Gly Ala Thr Ala
            340                 345                 350

Ala Ala Cys Cys Ala Ala Gly Ala Ala Thr Ala Gly Ala Ala Gly Ala
        355                 360                 365

Cys Gly Gly Ala Cys Ala Gly Thr Thr Ala Cys Ala Ala Cys Ala Ala
    370                 375                 380

Ala Ala Thr Ala Thr Ala Thr Thr Gly Ala Gly Gly Ala Thr Thr Cys
385                 390                 395                 400

Thr Cys Thr Ala Thr Ala Ala Thr Gly Gly Ala Thr Ala Thr Cys Cys
                405                 410                 415

Thr Ala Ala Thr Gly Ala Thr Cys Gly Thr Ala Ala Thr Gly Gly Gly
            420                 425                 430

Ala Thr Ala Ala Thr Gly Ala Ala Ala Gly Gly Gly Ala Thr Ala Gly
        435                 440                 445

Ala Thr Cys Cys Thr Cys Thr Ala Ala Ala Cys Gly Cys Thr Ala Thr
    450                 455                 460

Thr Thr Thr Ala Gly Thr Gly Ala Cys Thr Cys Ala Ala Ala Ala Thr
465                 470                 475                 480
```

```
Gly Cys Thr Ala Thr Thr Thr Gly Gly Thr Ala Cys Thr Ala Thr Ala
                485                 490                 495

Cys Thr Gly Ala Thr Ala Gly Thr Thr Cys Cys Thr Ala Thr Ala Thr
            500                 505                 510

Thr Thr Cys Thr Gly Ala Thr Ala Cys Thr Ala Gly Thr Ala Ala Ala
        515                 520                 525

Gly Cys Thr Thr Thr Thr Cys Ala Ala Cys Ala Ala Gly Ala Ala Gly
    530                 535                 540

Ala Ala Ala Cys Ala Gly Ala Thr Cys Thr Thr Ala Ala Ala Thr Thr
545                 550                 555                 560

Ala Gly Ala Thr Thr Cys Ala Cys Ala Gly Cys Ala Ala Cys Thr Ala
                565                 570                 575

Cys Ala Ala Cys Thr Ala Ala Thr Gly Cys Gly Thr Ala Ala Thr Gly
            580                 585                 590

Cys Gly Cys Thr Ala Ala Ala Ala Ala Gly Ala Thr Thr Ala Ala Thr
        595                 600                 605

Thr Ala Ala Thr Cys Cys Ala Ala Ala Ala Gly Ala Gly Gly Thr Ala
    610                 615                 620

Gly Ala Ala Ala Gly Thr Thr Thr Ala Cys Cys Gly Ala Ala Thr Cys
625                 630                 635                 640

Ala Gly Gly Thr Thr Cys Cys Cys Gly Cys Ala Ala Ala Thr Thr Ala
                645                 650                 655

Thr Cys Ala Gly Thr Thr Ala Ala Gly Thr Ala Thr Thr Thr Thr Thr
            660                 665                 670

Cys Ala Ala Thr Cys Thr Thr Cys Thr Gly Ala Thr Ala Ala Gly Ala
        675                 680                 685

Cys Thr Thr Thr Cys Cys Ala Ala Ala Ala Thr Cys Thr Thr Thr Thr
    690                 695                 700

Ala Ala Gly Thr Gly Cys Thr Gly Ala Gly Thr Ala Thr Gly Thr Thr
705                 710                 715                 720

Cys Cys Gly Gly Ala Thr Ala Cys Thr Cys Cys Cys Cys Cys Ala Ala
                725                 730                 735

Ala Ala Cys Cys Ala Gly Gly Ala Gly Ala Ala Gly Ala Gly Cys Cys
            740                 745                 750

Thr Cys Cys Gly Gly Cys Thr Ala Ala Ala Ala Cys Thr Gly Ala Ala
        755                 760                 765

Ala Ala Ala Ala Cys Ala Thr Cys Ala Gly Thr Cys Ala Thr Thr Ala
    770                 775                 780

Thr Cys Ala Gly Ala Ala Ala Ala Thr Ala Thr Gly Cys Gly Gly Ala
785                 790                 795                 800

Ala Gly Gly Thr Gly Ala Cys Thr Ala Cys Thr Cys Thr Ala Ala Ala
                805                 810                 815

Cys Thr Thr Cys Thr Ala Gly Ala Gly Gly Gly Ala Gly Cys Ala Ala
            820                 825                 830

Cys Cys Thr Thr Ala Ala Ala Gly Cys Thr Thr Gly Cys Thr Cys Ala
        835                 840                 845

Ala Ala Thr Thr Gly Ala Ala Gly Gly Ala Ala Gly Thr Gly Gly Thr
    850                 855                 860

Thr Thr Thr Cys Ala Gly Gly Ala Gly Ala Ala Ala Ala Thr Thr Thr
865                 870                 875                 880

Thr Thr Gly Ala Thr Ala Gly Thr Ala Ala Cys Ala Ala Gly Thr Cys
                885                 890                 895
```

-continued

```
Thr Gly Gly Ala Gly Ala Gly Ala Ala Gly Thr Ala Gly Ala Gly
                900             905             910

Cys Thr Ala Cys Cys Thr Ala Ala Thr Gly Gly Ala Cys Thr Thr
                915             920             925

Ala Cys Gly Thr Thr Thr Thr Ala Ala Gly Thr Gly Ala Gly Cys Thr
            930             935             940

Ala Ala Ala Ala Cys Cys Thr Cys Cys Thr Cys Ala Ala Gly Gly Ala
945             950             955             960

Thr Ala Thr Gly Gly Ala Gly Thr Thr Gly Cys Cys Ala Cys Ala Cys
                965             970             975

Cys Cys Ala Thr Thr Ala Cys Thr Thr Thr Ala Ala Ala Gly Thr
            980             985             990

Thr Gly Cys Ala Gly Cys Thr Gly  Ala Gly Ala Ala Ala  Gly Thr Thr
            995             1000            1005

Thr Thr  Ala Ala Thr Ala Ala  Ala Ala Ala Ala Thr  Ala Ala Ala
    1010            1015            1020

Gly Ala  Ala Gly Gly Thr Cys  Ala Ala Thr Thr Thr  Gly Thr Ala
    1025            1030            1035

Gly Ala  Gly Ala Ala Cys Cys  Ala Ala Ala Ala Thr  Ala Ala Gly
    1040            1045            1050

Gly Ala  Ala Ala Thr Cys Gly  Cys Ala Gly Ala Gly  Cys Cys Ala
    1055            1060            1065

Thr Ala  Thr Thr Cys Thr Gly  Thr Ala Ala Cys Ala  Gly Cys Thr
    1070            1075            1080

Thr Thr  Cys Ala Ala Thr Gly  Ala Cys Thr Thr Thr  Gly Ala Ala
    1085            1090            1095

Gly Ala  Gly Ala Thr Thr Gly  Thr Thr Ala Thr  Thr Thr Ala
    1100            1105            1110

Thr Cys  Thr Gly Ala Thr Thr  Thr Thr Ala Ala Thr  Ala Ala Cys
    1115            1120            1125

Thr Ala  Thr Gly Gly Thr Ala  Ala Gly Thr Thr Thr  Thr Ala Cys
    1130            1135            1140

Thr Ala  Thr Gly Cys Ala Ala  Ala Ala Ala Ala Thr  Ala Cys Thr
    1145            1150            1155

Ala Ala  Thr Gly Gly Ala Ala  Cys Thr Ala Ala Thr  Cys Ala Ala
    1160            1165            1170

Gly Thr  Thr Gly Thr Cys Thr  Ala Cys Thr Gly Thr  Thr Thr Cys
    1175            1180            1185

Ala Ala  Thr Gly Cys Thr Gly  Ala Thr Thr Thr Ala  Cys Ala Cys
    1190            1195            1200

Thr Cys  Ala Cys Cys Ala Cys  Cys Thr Gly Ala Cys  Thr Cys Ala
    1205            1210            1215

Thr Ala  Thr Gly Ala Thr Cys  Ala Cys Gly Gly Ala  Gly Cys Ala
    1220            1225            1230

Ala Ala  Thr Ala Thr Thr Gly  Ala Thr Cys Cys Thr  Gly Ala Thr
    1235            1240            1245

Gly Thr  Cys Ala Gly Thr Gly  Ala Ala Ala Gly Thr  Ala Ala Ala
    1250            1255            1260

Gly Ala  Gly Ala Thr Ala Ala  Ala Gly Thr Ala Thr  Ala Cys Ala
    1265            1270            1275

Cys Ala  Thr Gly Thr Thr Thr  Cys Thr Gly Gly Cys  Thr Ala Thr
    1280            1285            1290

Gly Ala  Thr Thr Thr Gly Thr  Ala Thr Ala Ala Ala  Thr Ala Thr
```

-continued

```
                    1295                1300                1305
Gly Cys Ala Gly Cys Cys Ala Cys Ala Cys Cys Ala Ala Gly Ala
        1310                1315                1320
Gly Ala Cys Ala Ala Ala Gly Ala Thr Gly Cys Thr Gly Ala Thr
        1325                1330                1335
Thr Thr Cys Thr Thr Cys Thr Thr Ala Ala Ala Cys Ala Thr
        1340                1345                1350
Ala Thr Cys Ala Ala Gly Ala Ala Ala Ala Thr Thr Cys Thr Thr
        1355                1360                1365
Gly Ala Thr Ala Ala Ala Gly Gly Thr Thr Ala Thr Ala Ala Gly
        1370                1375                1380
Ala Ala Gly Ala Ala Gly Gly Gly Gly Ala Thr Ala Cys Cys
        1385                1390                1395
Thr Ala Thr Ala Ala Gly Ala Cys Ala Thr Thr Ala Ala Cys Thr
        1400                1405                1410
Gly Ala Ala Gly Cys Thr Cys Ala Gly Thr Thr Thr Ala Gly Ala
        1415                1420                1425
Gly Cys Ala Gly Cys Ala Ala Cys Cys Cys Ala Ala Thr Thr Ala
        1430                1435                1440
Gly Cys Thr Ala Thr Thr Thr Ala Thr Thr Ala Cys Thr Ala Thr
        1445                1450                1455
Ala Cys Ala Gly Ala Thr Ala Gly Thr Gly Cys Thr Gly Ala Thr
        1460                1465                1470
Thr Thr Ala Ala Cys Ala Ala Cys Ala Cys Thr Thr Ala Ala Gly
        1475                1480                1485
Ala Cys Ala Thr Ala Thr Ala Ala Thr Gly Ala Thr Ala Ala Cys
        1490                1495                1500
Ala Ala Gly Gly Gly Thr Thr Ala Thr Cys Ala Thr Gly Gly Thr
        1505                1510                1515
Thr Thr Thr Gly Ala Thr Ala Ala Ala Cys Thr Gly Gly Ala Thr
        1520                1525                1530
Gly Ala Thr Gly Cys Ala Ala Cys Ala Thr Thr Ala Gly Cys Thr
        1535                1540                1545
Gly Thr Ala Gly Thr Thr Cys Ala Thr Gly Ala Gly Thr Thr Gly
        1550                1555                1560
Ala Thr Cys Ala Cys Cys Thr Ala Thr Gly Cys Thr Gly Ala Gly
        1565                1570                1575
Gly Ala Thr Gly Thr Cys Ala Cys Cys Thr Thr Ala Cys Cys Ala
        1580                1585                1590
Ala Thr Gly Ala Cys Thr Cys Ala Ala Ala Ala Thr Cys Thr Ala
        1595                1600                1605
Gly Ala Thr Thr Thr Cys Thr Thr Thr Gly Thr Thr Cys Cys Thr
        1610                1615                1620
Ala Ala Thr Ala Gly Cys Ala Gly Thr Ala Gly Ala Thr Ala Cys
        1625                1630                1635
Cys Ala Gly Gly Cys Ala Cys Thr Thr Ala Thr Thr Gly Gly Ala
        1640                1645                1650
Ala Cys Gly Cys Ala Gly Thr Ala Thr Cys Ala Thr Cys Cys Ala
        1655                1660                1665
Ala Ala Thr Gly Ala Ala Thr Thr Gly Ala Thr Thr Gly Ala Thr
        1670                1675                1680
Gly Thr Thr Ala Thr Thr Thr Cys Thr Ala Thr Gly Gly Ala Ala
        1685                1690                1695
```

```
Gly Ala  Thr Ala Ala Ala Cys  Ala Gly Gly Cys Thr  Cys Cys Thr
    1700                 1705                 1710

Ala Thr  Thr Ala Thr Thr Cys  Cys Thr Ala Thr Thr  Ala Cys Thr
    1715                 1720                 1725

Cys Ala  Cys Ala Ala Gly Thr  Thr Ala Ala Cys Thr  Ala Thr Thr
    1730                 1735                 1740

Thr Cys  Thr Ala Ala Ala Ala  Cys Thr Gly Thr Thr  Ala Cys Thr
    1745                 1750                 1755

Gly Gly  Ala Ala Cys Thr Ala  Thr Thr Gly Cys Ala  Gly Ala Thr
    1760                 1765                 1770

Ala Ala  Gly Ala Ala Ala Ala  Ala Ala Gly Ala Ala  Thr Thr Thr
    1775                 1780                 1785

Ala Ala  Cys Thr Thr Thr Gly  Ala Ala Ala Thr Ala  Cys Ala Thr
    1790                 1795                 1800

Thr Thr  Ala Ala Ala Ala Thr  Cys Thr Thr Cys Thr  Gly Ala Thr
    1805                 1810                 1815

Gly Gly  Ala Cys Ala Ala Gly  Cys Thr Ala Thr Ala  Ala Gly Thr
    1820                 1825                 1830

Gly Gly  Ala Ala Cys Ala Thr  Ala Thr Cys Cys Gly  Ala Cys Ala
    1835                 1840                 1845

Ala Ala  Cys Thr Cys Thr Gly  Gly Ala Gly Ala Ala  Cys Thr Cys
    1850                 1855                 1860

Ala Cys  Ala Gly Thr Thr Ala  Cys Ala Gly Ala Thr  Gly Gly Ala
    1865                 1870                 1875

Ala Ala  Ala Gly Cys Thr Ala  Cys Cys Thr Thr Cys  Ala Cys Ala
    1880                 1885                 1890

Thr Thr  Ala Ala Ala Gly Gly  Ala Thr Gly Gly Ala  Gly Ala Ala
    1895                 1900                 1905

Thr Cys  Ala Thr Thr Gly Ala  Thr Thr Gly Thr Thr  Gly Ala Gly
    1910                 1915                 1920

Gly Gly  Gly Cys Thr Ala Cys  Cys Thr Thr Cys Ala  Gly Gly Thr
    1925                 1930                 1935

Thr Ala  Cys Thr Cys Thr Thr  Ala Thr Gly Ala Ala  Ala Thr Thr
    1940                 1945                 1950

Ala Cys  Ala Gly Ala Ala Ala  Cys Gly Gly Gly Thr  Gly Cys Thr
    1955                 1960                 1965

Thr Cys  Ala Gly Ala Thr Thr  Ala Thr Gly Ala Gly  Gly Thr Ala
    1970                 1975                 1980

Ala Gly  Thr Gly Thr Thr Ala  Ala Thr Gly Gly Ala  Ala Ala Ala
    1985                 1990                 1995

Ala Ala  Thr Gly Cys Ala Cys  Cys Ala Gly Ala Thr  Gly Gly Ala
    2000                 2005                 2010

Ala Ala  Ala Gly Cys Gly Ala  Cys Gly Ala Ala Ala  Gly Cys Cys
    2015                 2020                 2025

Thr Cys  Ala Gly Thr Thr Ala  Ala Gly Gly Ala Ala  Gly Ala Thr
    2030                 2035                 2040

Gly Ala  Gly Ala Cys Thr Gly  Thr Ala Gly Cys Thr  Thr Thr Thr
    2045                 2050                 2055

Gly Ala  Ala Ala Ala Cys Cys  Gly Ala Ala Ala Ala  Gly Ala Thr
    2060                 2065                 2070

Cys Thr  Thr Gly Thr Cys Cys  Cys Ala Cys Cys Ala  Ala Cys Thr
    2075                 2080                 2085
```

```
Gly Gly Thr Thr Thr Gly Ala Cys Ala Ala Cys Ala Gly Ala Thr
    2090                2095                2100

Gly Gly Gly Gly Cys Thr Ala Thr Cys Thr Ala Thr Cys Thr Thr
    2105                2110                2115

Thr Gly Gly Thr Thr Gly Thr Ala Thr Thr Ala Cys Thr Thr
    2120                2125                2130

Gly Thr Thr Cys Cys Ala Thr Thr Thr Gly Gly Gly Thr Thr Ala
    2135                2140                2145

Thr Thr Gly Gly Thr Thr Thr Gly Gly Cys Thr Ala Thr Thr Thr
    2150                2155                2160

Gly Gly Thr Cys Gly Thr Ala Ala Ala Gly Gly Gly Ala Cys Thr
    2165                2170                2175

Ala Ala Ala Ala Ala Ala Thr Gly Ala
    2180                2185

<210> SEQ ID NO 5
<211> LENGTH: 6
<212> TYPE: PRT
<213> ORGANISM: Artificial Sequence
<220> FEATURE:
<223> OTHER INFORMATION: Synthetic construct

<400> SEQUENCE: 5

Arg Lys Gly Thr Lys Lys
1               5

<210> SEQ ID NO 6
<211> LENGTH: 151
<212> TYPE: PRT
<213> ORGANISM: Streptococcus pyogenes

<400> SEQUENCE: 6

Lys Leu Thr Ile Ser Lys Thr Val Thr Gly Thr Ile Ala Asp Lys Lys
1               5                   10                  15

Lys Glu Phe Asn Phe Glu Ile His Leu Lys Ser Ser Asp Gly Gln Ala
            20                  25                  30

Ile Ser Gly Thr Tyr Pro Thr Asn Ser Gly Glu Leu Thr Val Thr Asp
        35                  40                  45

Gly Lys Ala Thr Phe Thr Leu Lys Asp Gly Glu Ser Leu Ile Val Glu
    50                  55                  60

Gly Leu Pro Ser Gly Tyr Ser Tyr Glu Ile Thr Glu Thr Gly Ala Ser
65                  70                  75                  80

Asp Tyr Glu Val Ser Val Asn Gly Lys Asn Ala Pro Asp Gly Lys Ala
                85                  90                  95

Thr Lys Ala Ser Val Lys Glu Asp Glu Thr Val Ala Phe Glu Asn Arg
            100                 105                 110

Lys Asp Leu Val Pro Pro Thr Gly Leu Thr Thr Asp Gly Ala Ile Tyr
        115                 120                 125

Leu Trp Leu Leu Leu Leu Val Pro Phe Gly Leu Leu Val Trp Leu Phe
    130                 135                 140

Gly Arg Lys Gly Thr Lys Lys
145                 150

<210> SEQ ID NO 7
<211> LENGTH: 239
<212> TYPE: PRT
<213> ORGANISM: Streptococcus pyogenes

<400> SEQUENCE: 7
```

Met Thr Ile Val Gln Val Ile Asn Lys Ala Ile Asp Thr Leu Ile Leu
1               5                   10                  15

Ile Phe Cys Leu Val Val Leu Phe Leu Ala Gly Phe Gly Leu Trp Asp
            20                  25                  30

Ser Tyr His Leu Tyr Gln Gln Ala Asp Ala Ser Asn Phe Lys Lys Phe
            35                  40                  45

Lys Thr Ala Gln Gln Pro Lys Phe Glu Asp Leu Leu Ala Leu Asn
        50                  55                  60

Glu Asp Val Ile Gly Trp Leu Asn Ile Pro Gly Thr His Ile Asp Tyr
65                  70                  75                  80

Pro Leu Val Gln Gly Lys Thr Asn Leu Glu Tyr Ile Asn Lys Ala Val
                85                  90                  95

Asp Gly Ser Val Ala Met Ser Gly Ser Leu Phe Leu Asp Thr Arg Asn
                100                 105                 110

His Asn Asp Phe Thr Asp Asp Tyr Ser Leu Ile Tyr Gly His His Met
            115                 120                 125

Ala Gly Asn Ala Met Phe Gly Glu Ile Pro Lys Phe Leu Lys Lys Asp
130                 135                 140

Phe Phe Ser Lys His Asn Lys Ala Ile Ile Glu Thr Lys Glu Arg Lys
145                 150                 155                 160

Lys Leu Thr Val Thr Ile Phe Ala Cys Leu Lys Thr Asp Ala Phe Asn
                165                 170                 175

Gln Leu Val Phe Asn Pro Asn Ala Ile Thr Asn Gln Asp Gln Gln Arg
            180                 185                 190

Gln Leu Val Asp Tyr Ile Ser Lys Arg Ser Lys Gln Phe Lys Pro Val
            195                 200                 205

Lys Leu Lys His His Thr Lys Phe Val Ala Phe Ser Thr Cys Glu Asn
210                 215                 220

Phe Ser Thr Asp Asn Arg Val Ile Val Val Gly Thr Ile Gln Glu
225                 230                 235

<210> SEQ ID NO 8
<211> LENGTH: 720
<212> TYPE: PRT
<213> ORGANISM: Streptococcus pyogenes

<400> SEQUENCE: 8

Ala Thr Gly Ala Cys Ala Ala Thr Thr Gly Thr Ala Cys Ala Gly Gly
1               5                   10                  15

Thr Thr Ala Thr Cys Ala Ala Thr Ala Ala Ala Gly Cys Cys Ala Thr
            20                  25                  30

Thr Gly Ala Thr Ala Cys Thr Cys Thr Cys Ala Thr Thr Cys Thr Thr
            35                  40                  45

Ala Thr Cys Thr Thr Thr Thr Gly Thr Thr Thr Ala Gly Thr Cys Gly
        50                  55                  60

Thr Ala Cys Thr Ala Thr Thr Thr Thr Thr Ala Gly Cys Thr Gly Gly
65                  70                  75                  80

Thr Thr Thr Thr Gly Gly Thr Thr Gly Thr Gly Gly Ala Thr
                85                  90                  95

Thr Cys Thr Thr Ala Thr Cys Ala Thr Cys Thr Cys Thr Ala Thr Cys
                100                 105                 110

Ala Ala Cys Ala Ala Gly Cys Ala Gly Ala Cys Gly Cys Thr Thr Cys
            115                 120                 125

Thr Ala Ala Thr Thr Thr Cys Ala Ala Ala Ala Ala Thr Thr Thr

-continued

```
    130                 135                 140

Ala Ala Ala Ala Cys Ala Gly Cys Thr Cys Ala Ala Cys Ala Ala Cys
145                 150                 155                 160

Ala Gly Cys Cys Thr Ala Ala Ala Thr Thr Thr Gly Ala Ala Gly Ala
                165                 170                 175

Cys Thr Thr Gly Thr Thr Ala Gly Cys Thr Thr Thr Gly Ala Ala Thr
            180                 185                 190

Gly Ala Gly Gly Ala Thr Gly Thr Cys Ala Thr Thr Gly Gly Thr Thr
        195                 200                 205

Gly Gly Thr Thr Ala Ala Ala Thr Ala Thr Cys Cys Cys Ala Gly Gly
    210                 215                 220

Gly Ala Cys Thr Cys Ala Thr Ala Thr Thr Gly Ala Thr Thr Ala Thr
225                 230                 235                 240

Cys Cys Thr Cys Thr Ala Gly Thr Thr Cys Ala Gly Gly Gly Ala Ala
                245                 250                 255

Ala Ala Ala Cys Gly Ala Ala Thr Thr Thr Ala Gly Ala Gly Thr Ala
            260                 265                 270

Thr Ala Thr Thr Ala Ala Thr Ala Ala Ala Gly Cys Ala Gly Thr Thr
        275                 280                 285

Gly Ala Thr Gly Gly Cys Ala Gly Thr Gly Thr Thr Gly Cys Cys Ala
    290                 295                 300

Thr Gly Thr Cys Thr Gly Gly Thr Ala Gly Thr Thr Thr Ala Thr Thr
305                 310                 315                 320

Thr Thr Thr Ala Gly Ala Thr Ala Cys Ala Cys Gly Gly Ala Ala Thr
                325                 330                 335

Cys Ala Thr Ala Ala Thr Gly Ala Thr Thr Thr Thr Ala Cys Gly Gly
            340                 345                 350

Ala Cys Gly Ala Thr Thr Ala Cys Thr Cys Thr Cys Thr Gly Ala Thr
        355                 360                 365

Thr Thr Ala Thr Gly Gly Cys Cys Ala Thr Cys Ala Thr Ala Thr Gly
    370                 375                 380

Gly Cys Ala Gly Gly Thr Ala Ala Thr Gly Cys Cys Ala Thr Gly Thr
385                 390                 395                 400

Thr Thr Gly Gly Cys Gly Ala Ala Ala Thr Thr Cys Cys Ala Ala Ala
                405                 410                 415

Ala Thr Thr Thr Thr Thr Ala Ala Ala Ala Ala Ala Gly Gly Ala Thr
            420                 425                 430

Thr Thr Thr Thr Thr Cys Ala Gly Cys Ala Ala Ala Cys Ala Thr Ala
        435                 440                 445

Ala Thr Ala Ala Ala Gly Cys Thr Ala Thr Cys Ala Thr Thr Gly Ala
    450                 455                 460

Ala Ala Cys Ala Ala Ala Ala Gly Ala Gly Ala Gly Ala Ala Ala Ala
465                 470                 475                 480

Ala Ala Ala Cys Thr Ala Ala Cys Cys Gly Thr Cys Ala Cys Thr Ala
                485                 490                 495

Thr Thr Thr Thr Thr Gly Cys Thr Thr Gly Cys Cys Thr Cys Ala Ala
            500                 505                 510

Gly Ala Cys Ala Gly Ala Thr Gly Cys Cys Thr Thr Thr Ala Ala Cys
        515                 520                 525

Cys Ala Gly Thr Thr Ala Gly Thr Thr Thr Thr Thr Ala Ala Thr Cys
    530                 535                 540

Cys Thr Ala Ala Thr Gly Cys Thr Ala Thr Thr Ala Cys Cys Ala Ala
545                 550                 555                 560
```

```
Thr Cys Ala Ala Gly Ala Cys Cys Ala Cys Ala Ala Gly Gly
            565                 570                 575

Cys Ala Gly Cys Thr Thr Gly Thr Gly Ala Thr Ala Thr Ala
        580                 585                 590

Thr Cys Ala Gly Thr Ala Ala Ala Ala Gly Ala Thr Cys Ala Ala
    595                 600                 605

Ala Cys Ala Ala Thr Thr Ala Ala Ala Cys Cys Thr Gly Thr Thr
    610                 615                 620

Ala Ala Ala Thr Thr Gly Ala Ala Gly Cys Ala Thr Cys Ala Thr Ala
625                 630                 635                 640

Cys Ala Ala Ala Gly Thr Thr Cys Gly Thr Thr Gly Cys Thr Thr Thr
                645                 650                 655

Thr Thr Cys Ala Ala Cys Gly Thr Gly Thr Gly Ala Ala Ala Ala Thr
            660                 665                 670

Thr Thr Thr Thr Cys Thr Ala Cys Thr Gly Ala Cys Ala Ala Thr Cys
            675                 680                 685

Gly Thr Gly Thr Thr Ala Thr Cys Cys Thr Thr Gly Thr Cys Gly Gly
        690                 695                 700

Thr Ala Cys Thr Ala Thr Thr Cys Ala Ala Gly Ala Ala Thr Ala Ala
705                 710                 715                 720

<210> SEQ ID NO 9
<211> LENGTH: 5
<212> TYPE: PRT
<213> ORGANISM: Artificial Sequence
<220> FEATURE:
<223> OTHER INFORMATION: Synthetic construct

<400> SEQUENCE: 9

Gln Val Pro Thr Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic construct

<400> SEQUENCE: 10

Val Pro Pro Thr Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(2)
<223> OTHER INFORMATION: where X is any protein

<400> SEQUENCE: 11

Xaa Xaa Pro Thr Gly
1               5

<210> SEQ ID NO 12
<211> LENGTH: 344
<212> TYPE: PRT
<213> ORGANISM: Streptococcus pyogenes
```

<400> SEQUENCE: 12

```
Met Lys Lys Asn Lys Leu Leu Ala Thr Ala Ile Leu Ala Thr Ala
1               5                   10                  15

Leu Gly Thr Ala Ser Leu Asn Gln Asn Val Lys Ala Glu Thr Ala Gly
            20                  25                  30

Val Ser Glu Asn Ala Lys Leu Ile Val Lys Lys Thr Phe Asp Ser Tyr
        35                  40                  45

Thr Asp Asn Glu Val Leu Met Pro Lys Ala Asp Tyr Thr Phe Lys Val
    50                  55                  60

Glu Ala Asp Ser Thr Ala Ser Gly Lys Thr Lys Asp Gly Leu Glu Ile
65                  70                  75                  80

Lys Pro Gly Ile Val Asn Gly Leu Thr Glu Gln Ile Ile Ser Tyr Thr
                85                  90                  95

Asn Thr Asp Lys Pro Asp Ser Lys Val Lys Ser Thr Glu Phe Asp Phe
            100                 105                 110

Ser Lys Val Val Phe Pro Gly Ile Gly Val Tyr Arg Tyr Thr Val Ser
        115                 120                 125

Glu Lys Gln Gly Asp Val Glu Gly Ile Thr Tyr Asp Thr Lys Lys Trp
    130                 135                 140

Thr Val Asp Val Tyr Val Gly Asn Lys Glu Gly Gly Phe Glu Pro
145                 150                 155                 160

Lys Phe Ile Val Ser Lys Glu Gln Gly Thr Asp Val Lys Lys Pro Val
                165                 170                 175

Asn Phe Asn Asn Ser Phe Ala Thr Thr Ser Leu Lys Val Lys Lys Asn
            180                 185                 190

Val Ser Gly Asn Thr Gly Glu Leu Gln Lys Glu Phe Asp Phe Thr Leu
        195                 200                 205

Thr Leu Asn Glu Ser Thr Asn Phe Lys Lys Asp Gln Ile Val Ser Leu
    210                 215                 220

Gln Lys Gly Asn Glu Lys Phe Glu Val Lys Ile Gly Thr Pro Tyr Lys
225                 230                 235                 240

Phe Lys Leu Lys Asn Gly Glu Ser Ile Gln Leu Asp Lys Leu Pro Val
                245                 250                 255

Gly Ile Thr Tyr Lys Val Asn Glu Met Glu Ala Asn Lys Asp Gly Tyr
            260                 265                 270

Lys Thr Thr Ala Ser Leu Lys Glu Gly Asp Gly Gln Ser Lys Met Tyr
        275                 280                 285

Gln Leu Asp Met Glu Gln Lys Thr Asp Glu Ser Ala Asp Glu Ile Val
    290                 295                 300

Val Thr Asn Lys Arg Asp Thr Gln Val Pro Thr Gly Val Val Gly Thr
305                 310                 315                 320

Leu Ala Pro Phe Ala Val Leu Ser Ile Val Ala Ile Gly Gly Val Ile
                325                 330                 335

Tyr Ile Thr Lys Arg Lys Lys Ala
            340
```

<210> SEQ ID NO 13
<211> LENGTH: 1035
<212> TYPE: PRT
<213> ORGANISM: Streptococcus pyogenes

<400> SEQUENCE: 13

```
Ala Thr Gly Ala Ala Ala Ala Ala Ala Ala Cys Ala Ala Ala Thr
1               5                   10                  15
```

```
Thr Ala Thr Thr Ala Cys Thr Thr Gly Cys Thr Ala Cys Thr Gly Cys
            20                  25                  30

Ala Ala Thr Cys Thr Thr Ala Gly Cys Ala Ala Cys Thr Gly Cys Thr
        35                  40                  45

Thr Thr Ala Gly Gly Ala Ala Cys Ala Gly Cys Thr Thr Cys Thr Thr
    50                  55                  60

Thr Ala Ala Ala Thr Cys Ala Ala Ala Ala Cys Gly Thr Ala Ala Ala
65                  70                  75                  80

Ala Gly Cys Thr Gly Ala Gly Ala Cys Gly Gly Cys Ala Gly Gly Ala
                85                  90                  95

Gly Thr Gly Thr Cys Cys Gly Ala Ala Ala Ala Thr Gly Cys Ala Ala
            100                 105                 110

Ala Ala Thr Thr Ala Ala Thr Ala Gly Thr Ala Ala Ala Ala Ala Ala
        115                 120                 125

Gly Ala Cys Ala Thr Thr Thr Gly Ala Cys Thr Cys Thr Thr Ala Thr
    130                 135                 140

Ala Cys Ala Gly Ala Cys Ala Ala Thr Gly Ala Ala Gly Thr Thr Thr
145                 150                 155                 160

Thr Ala Ala Thr Gly Cys Cys Ala Ala Ala Ala Gly Cys Thr Gly Ala
                165                 170                 175

Thr Thr Ala Thr Ala Cys Thr Thr Thr Thr Ala Ala Ala Gly Thr Ala
            180                 185                 190

Gly Ala Gly Gly Cys Ala Gly Ala Thr Ala Gly Thr Ala Cys Ala Gly
        195                 200                 205

Cys Thr Ala Gly Thr Gly Gly Cys Ala Ala Ala Ala Cys Gly Ala Ala
    210                 215                 220

Ala Gly Ala Cys Gly Gly Thr Thr Thr Ala Gly Ala Gly Ala Thr Thr
225                 230                 235                 240

Ala Ala Gly Cys Cys Ala Gly Gly Thr Ala Thr Thr Gly Thr Thr Ala
                245                 250                 255

Ala Thr Gly Gly Thr Thr Thr Ala Ala Cys Ala Gly Ala Ala Cys Ala
            260                 265                 270

Gly Ala Thr Thr Ala Thr Cys Ala Gly Cys Thr Ala Thr Ala Cys Thr
        275                 280                 285

Ala Ala Thr Ala Cys Thr Gly Ala Thr Ala Ala Ala Cys Cys Ala Gly
    290                 295                 300

Ala Thr Ala Gly Thr Ala Ala Ala Gly Thr Thr Ala Ala Ala Ala Gly
305                 310                 315                 320

Thr Ala Cys Ala Gly Ala Gly Thr Thr Thr Gly Ala Thr Thr Thr Thr
                325                 330                 335

Thr Cys Ala Ala Ala Ala Gly Thr Ala Gly Thr Ala Thr Thr Cys Cys
            340                 345                 350

Cys Thr Gly Gly Thr Ala Thr Thr Gly Gly Thr Gly Thr Thr Thr Ala
        355                 360                 365

Cys Cys Gly Cys Thr Ala Thr Ala Cys Thr Gly Thr Thr Thr Cys Ala
    370                 375                 380

Gly Ala Ala Ala Ala Ala Cys Ala Ala Gly Gly Thr Gly Ala Thr Gly
385                 390                 395                 400

Thr Thr Gly Ala Ala Gly Gly Ala Ala Thr Thr Ala Cys Cys Thr Ala
                405                 410                 415

Cys Gly Ala Thr Ala Cys Thr Ala Ala Gly Ala Ala Gly Thr Gly Gly
            420                 425                 430
```

```
Ala Cys Ala Gly Thr Ala Gly Ala Thr Thr Thr Ala Thr Gly
        435                 440                 445

Thr Thr Gly Gly Ala Ala Ala Cys Ala Ala Gly Ala Ala Gly Gly
450                 455                 460

Thr Gly Gly Thr Gly Gly Thr Thr Thr Gly Ala Ala Cys Cys Thr
465                 470                 475                 480

Ala Ala Gly Thr Thr Ala Thr Thr Gly Thr Ala Thr Cys Thr Ala
                485                 490                 495

Ala Gly Gly Ala Ala Cys Ala Ala Gly Ala Ala Cys Ala Gly Ala
                500                 505                 510

Cys Gly Thr Cys Ala Ala Ala Ala Ala Cys Cys Ala Gly Thr Thr
            515                 520                 525

Ala Ala Thr Thr Thr Thr Ala Ala Cys Ala Ala Cys Thr Cys Gly Thr
530                 535                 540

Thr Thr Gly Cys Ala Ala Cys Thr Ala Cys Thr Thr Cys Gly Thr Thr
545                 550                 555                 560

Ala Ala Ala Ala Gly Thr Thr Ala Ala Gly Ala Ala Gly Ala Ala Thr
                565                 570                 575

Gly Thr Ala Thr Cys Gly Gly Gly Ala Ala Thr Ala Cys Thr Gly
            580                 585                 590

Gly Ala Gly Ala Ala Thr Thr Gly Cys Ala Ala Ala Ala Gly Ala
            595                 600                 605

Ala Thr Thr Thr Gly Ala Cys Thr Thr Thr Ala Cys Ala Thr Thr Gly
                610                 615                 620

Ala Cys Gly Cys Thr Thr Ala Thr Gly Ala Ala Ala Gly Cys Ala
625                 630                 635                 640

Cys Gly Ala Ala Thr Thr Thr Ala Ala Ala Ala Ala Ala Gly Ala
                645                 650                 655

Thr Cys Ala Ala Ala Thr Thr Gly Thr Thr Cys Thr Thr Thr Ala
            660                 665                 670

Cys Ala Ala Ala Ala Ala Gly Gly Ala Ala Ala Cys Gly Ala Gly Ala
                675                 680                 685

Ala Ala Thr Thr Thr Gly Ala Ala Gly Thr Thr Ala Ala Gly Ala Thr
690                 695                 700

Thr Gly Gly Thr Ala Cys Thr Cys Cys Cys Thr Ala Cys Ala Ala Gly
705                 710                 715                 720

Thr Thr Thr Ala Ala Ala Cys Thr Cys Ala Ala Ala Ala Thr Gly
                725                 730                 735

Gly Gly Gly Ala Ala Thr Cys Thr Ala Thr Thr Cys Ala Ala Cys Thr
                740                 745                 750

Ala Gly Ala Cys Ala Ala Gly Thr Thr Ala Cys Cys Ala Gly Thr Thr
                755                 760                 765

Gly Gly Thr Ala Thr Thr Ala Cys Thr Thr Ala Thr Ala Ala Ala Gly
            770                 775                 780

Thr Cys Ala Ala Thr Gly Ala Ala Ala Thr Gly Gly Ala Ala Gly Cys
785                 790                 795                 800

Thr Ala Ala Thr Ala Ala Ala Gly Ala Thr Gly Gly Thr Ala Thr
                805                 810                 815

Ala Ala Ala Ala Cys Ala Cys Ala Gly Cys Ala Thr Cys Cys Thr
                820                 825                 830

Thr Gly Ala Ala Ala Gly Ala Gly Gly Gly Ala Gly Ala Thr Gly Gly
                835                 840                 845

Thr Cys Ala Ala Thr Cys Thr Ala Ala Ala Ala Thr Gly Thr Ala Thr
```

```
                    850                 855                 860
Cys Ala Ala Thr Thr Gly Gly Ala Thr Ala Thr Gly Gly Ala Ala Cys
865                 870                 875                 880

Ala Ala Ala Ala Ala Ala Cys Ala Gly Ala Cys Gly Ala Ala Thr Cys
                    885                 890                 895

Thr Gly Cys Thr Gly Ala Cys Gly Ala Ala Thr Cys Gly Thr Thr
                900                 905                 910

Gly Thr Cys Ala Cys Ala Ala Thr Ala Ala Gly Cys Gly Thr Gly
            915                 920                 925

Ala Cys Ala Cys Thr Cys Ala Ala Gly Thr Thr Cys Cys Ala Ala Cys
930                 935                 940

Thr Gly Gly Thr Gly Thr Thr Gly Thr Ala Gly Gly Cys Ala Cys Cys
945                 950                 955                 960

Cys Thr Thr Gly Cys Thr Cys Cys Ala Thr Thr Gly Cys Ala Gly
                965                 970                 975

Thr Thr Cys Thr Thr Ala Gly Cys Ala Thr Gly Thr Gly Gly Cys
                980                 985                 990

Thr Ala Thr Thr Gly Gly Thr Gly  Gly Ala Gly Thr Thr  Ala Thr Cys
            995                 1000                1005

Thr Ala  Thr Ala Thr Thr Ala  Cys Ala Ala Ala  Cys Gly Thr
        1010                1015                1020

Ala Ala  Ala Ala Ala Ala Gly  Cys Thr Thr Ala Ala
1025                1030                1035

<210> SEQ ID NO 14
<211> LENGTH: 172
<212> TYPE: PRT
<213> ORGANISM: Streptococcus pyogenes

<400> SEQUENCE: 14

Met Thr Asn Tyr Leu Asn Arg Leu Asn Glu Asn Pro Leu Leu Lys Ala
1               5                   10                  15

Phe Ile Arg Leu Val Leu Lys Ile Ser Ile Ile Gly Phe Leu Gly Tyr
                20                  25                  30

Ile Leu Phe Gln Tyr Val Phe Gly Val Met Ile Val Asn Thr Asn Gln
            35                  40                  45

Met Ser Pro Ala Val Ser Ala Gly Asp Gly Val Leu Tyr Tyr Arg Leu
50                  55                  60

Thr Asp Arg Tyr His Ile Asn Asp Val Val Tyr Glu Val Asp Asp
65                  70                  75                  80

Thr Leu Lys Val Gly Arg Ile Ala Ala Gln Ala Gly Asp Glu Val Asn
                85                  90                  95

Phe Thr Gln Glu Gly Gly Leu Leu Ile Asn Gly His Pro Pro Glu Lys
            100                 105                 110

Glu Val Pro Tyr Leu Thr Tyr Pro His Ser Ser Gly Pro Asn Phe Pro
        115                 120                 125

Tyr Lys Val Pro Thr Gly Thr Tyr Phe Ile Leu Asn Asp Tyr Arg Glu
    130                 135                 140

Glu Arg Leu Asp Ser Arg Tyr Tyr Gly Ala Leu Pro Ile Asn Gln Ile
145                 150                 155                 160

Lys Gly Lys Ile Ser Thr Leu Leu Arg Val Arg Gly
                165                 170

<210> SEQ ID NO 15
<211> LENGTH: 522
```

<212> TYPE: PRT
<213> ORGANISM: Streptococcus pyogenes

<400> SEQUENCE: 15

Ala Thr Gly Ala Cys Thr Ala Ala Thr Thr Ala Cys Cys Thr Ala Ala
1 5 10 15

Ala Thr Cys Gly Cys Thr Thr Ala Ala Ala Thr Gly Ala Gly Ala Ala
20 25 30

Thr Cys Cys Ala Cys Thr Ala Thr Thr Gly Ala Ala Ala Gly Cys Thr
35 40 45

Thr Thr Cys Ala Thr Ala Cys Gly Gly Thr Thr Ala Gly Thr Ala Cys
50 55 60

Thr Thr Ala Ala Gly Ala Thr Thr Thr Cys Thr Ala Thr Thr Ala Thr
65 70 75 80

Thr Gly Gly Ala Thr Thr Thr Cys Thr Ala Gly Gly Thr Thr Ala Cys
85 90 95

Ala Thr Thr Cys Thr Ala Thr Thr Thr Cys Ala Gly Thr Ala Thr Gly
100 105 110

Thr Thr Thr Thr Thr Gly Gly Cys Gly Thr Cys Ala Thr Gly Ala Thr
115 120 125

Thr Gly Thr Thr Ala Ala Cys Ala Cys Ala Ala Ala Thr Cys Ala Gly
130 135 140

Ala Thr Gly Ala Gly Thr Cys Cys Thr Gly Cys Thr Gly Thr Ala Ala
145 150 155 160

Gly Thr Gly Cys Thr Gly Gly Thr Gly Ala Thr Gly Gly Ala Gly Thr
165 170 175

Cys Thr Thr Ala Thr Ala Thr Thr Ala Thr Cys Gly Thr Thr Thr Gly
180 185 190

Ala Cys Thr Gly Ala Thr Cys Gly Cys Thr Ala Thr Cys Ala Thr Ala
195 200 205

Thr Thr Ala Ala Thr Gly Ala Thr Gly Thr Gly Gly Thr Gly Gly Thr
210 215 220

Gly Thr Ala Thr Gly Ala Gly Gly Thr Thr Gly Ala Thr Gly Ala Cys
225 230 235 240

Ala Cys Thr Thr Thr Gly Ala Ala Ala Gly Thr Thr Gly Gly Thr Cys
245 250 255

Gly Ala Ala Thr Thr Gly Cys Cys Gly Cys Thr Cys Ala Ala Gly Cys
260 265 270

Thr Gly Gly Cys Gly Ala Thr Gly Ala Gly Gly Thr Thr Ala Ala Thr
275 280 285

Thr Thr Thr Ala Cys Gly Cys Ala Ala Gly Ala Ala Gly Gly Ala Gly
290 295 300

Gly Ala Cys Thr Gly Thr Thr Gly Ala Thr Thr Ala Ala Thr Gly Gly
305 310 315 320

Cys Cys Ala Thr Cys Cys Ala Cys Cys Ala Gly Ala Ala Ala Ala Ala
325 330 335

Gly Ala Gly Gly Thr Cys Cys Cys Thr Thr Ala Cys Cys Thr Gly Ala
340 345 350

Cys Gly Thr Ala Thr Cys Cys Thr Cys Ala Cys Thr Cys Ala Ala Gly
355 360 365

Thr Gly Gly Thr Cys Cys Ala Ala Ala Cys Thr Thr Thr Cys Cys Cys
370 375 380

Thr Ala Thr Ala Ala Ala Gly Thr Thr Cys Cys Thr Ala Cys Gly Gly
385 390 395 400

Gly Thr Ala Cys Gly Thr Ala Thr Thr Cys Ala Thr Ala Thr
            405                 410                 415
Gly Ala Ala Thr Gly Ala Thr Thr Ala Thr Cys Gly Thr Gly Ala Ala
            420                 425                 430
Gly Ala Ala Cys Gly Thr Thr Gly Gly Ala Cys Ala Gly Thr Cys
            435                 440                 445
Gly Thr Thr Ala Thr Thr Ala Thr Gly Gly Gly Cys Gly Thr Thr
        450                 455                 460
Ala Cys Cys Cys Ala Thr Cys Ala Ala Thr Cys Ala Ala Thr Cys
465                 470                 475                 480
Ala Ala Ala Gly Gly Gly Ala Ala Ala Thr Cys Thr Cys Ala Ala
                485                 490                 495
Cys Thr Cys Thr Ala Thr Thr Ala Ala Gly Ala Gly Thr Gly Ala Gly
            500                 505                 510
Ala Gly Gly Ala Ala Thr Thr Thr Ala Ala
        515                 520

<210> SEQ ID NO 16
<211> LENGTH: 50
<212> TYPE: DNA
<213> ORGANISM: Artificial Sequence
<220> FEATURE:
<223> OTHER INFORMATION: Synthetic construct

<400> SEQUENCE: 16
ccgaaaatgc aaaattaata gtaaaagcta catttgactc ttatacagac          50

<210> SEQ ID NO 17
<211> LENGTH: 50
<212> TYPE: DNA
<213> ORGANISM: Artificial Sequence
<220> FEATURE:
<223> OTHER INFORMATION: Synthetic construct

<400> SEQUENCE: 17
gtctgtataa gagtcaaatg tagcttttac tattaatttt gcattttcgg          50

<210> SEQ ID NO 18
<211> LENGTH: 48
<212> TYPE: DNA
<213> ORGANISM: Artificial Sequence
<220> FEATURE:
<223> OTHER INFORMATION: Synthetic construct

<400> SEQUENCE: 18
cgaaagacgg tttagagatt gctccaggta ttgttaatgg tttaacag            48

<210> SEQ ID NO 19
<211> LENGTH: 48
<212> TYPE: DNA
<213> ORGANISM: Artificial Sequence
<220> FEATURE:
<223> OTHER INFORMATION: Synthetic construct

<400> SEQUENCE: 19
ctgttaaacc attaacaata cctggagcaa tctctaaacc gtctttcg            48

<210> SEQ ID NO 20
<211> LENGTH: 48
<212> TYPE: DNA
<213> ORGANISM: Artificial Sequence
<220> FEATURE:

<223> OTHER INFORMATION: Synthetic construct

<400> SEQUENCE: 20
cagctatact aatactgatg cacagatagt aaagttaaaa gtacagag       48

<210> SEQ ID NO 21
<211> LENGTH: 49
<212> TYPE: DNA
<213> ORGANISM: Artificial Sequence
<220> FEATURE:
<223> OTHER INFORMATION: Synthetic construct

<400> SEQUENCE: 21
ctctgtactt ttaactttac tatctggtgc atcagtatta gtatagctg       49

<210> SEQ ID NO 22
<211> LENGTH: 51
<212> TYPE: DNA
<213> ORGANISM: Artificial Sequence
<220> FEATURE:
<223> OTHER INFORMATION: Synthetic construct

<400> SEQUENCE: 22
cttttgaaaa atcaaactct gtacttgcaa ctttactatc tggtttatca g       51

<210> SEQ ID NO 23
<211> LENGTH: 51
<212> TYPE: DNA
<213> ORGANISM: Artificial Sequence
<220> FEATURE:
<223> OTHER INFORMATION: Synthetic construct

<400> SEQUENCE: 23
cttttgaaaa atcaaactct gtacttgcaa ctttactatc tggtttatca g       51

<210> SEQ ID NO 24
<211> LENGTH: 47
<212> TYPE: DNA
<213> ORGANISM: Artificial Sequence
<220> FEATURE:
<223> OTHER INFORMATION: Synthetic construct

<400> SEQUENCE: 24
ctaaggaaca aggaacagac gtcgcaaaac cagttaattt taacaac       47

<210> SEQ ID NO 25
<211> LENGTH: 47
<212> TYPE: DNA
<213> ORGANISM: Artificial Sequence
<220> FEATURE:
<223> OTHER INFORMATION: Synthetic construct

<400> SEQUENCE: 25
gttgttaaaa ttaactggtt ttcggacgtc tgttccttgt tccttag       47

<210> SEQ ID NO 26
<211> LENGTH: 45
<212> TYPE: DNA
<213> ORGANISM: Artificial Sequence
<220> FEATURE:
<223> OTHER INFORMATION: Synthetic construct

<400> SEQUENCE: 26
ctaaggaaca aggaacagac gtccgaacca gttaatttta acaac       45

```
<210> SEQ ID NO 27
<211> LENGTH: 47
<212> TYPE: DNA
<213> ORGANISM: Artificial Sequence
<220> FEATURE:
<223> OTHER INFORMATION: Synthetic construct

<400> SEQUENCE: 27
gttgttaaaa ttaactggtt ttcggacgtc tgttccttgt tccttag         47

<210> SEQ ID NO 28
<211> LENGTH: 47
<212> TYPE: DNA
<213> ORGANISM: Artificial Sequence
<220> FEATURE:
<223> OTHER INFORMATION: Synthetic construct

<400> SEQUENCE: 28
ctaaggaaca aggaacagac gtcaaagcac cagttaattt taacaac         47

<210> SEQ ID NO 29
<211> LENGTH: 47
<212> TYPE: DNA
<213> ORGANISM: Artificial Sequence
<220> FEATURE:
<223> OTHER INFORMATION: Synthetic construct

<400> SEQUENCE: 29
gttgttaaaa ttaactggtg ctttgacgtc tgttccttgt tccttag         47

<210> SEQ ID NO 30
<211> LENGTH: 47
<212> TYPE: DNA
<213> ORGANISM: Artificial Sequence
<220> FEATURE:
<223> OTHER INFORMATION: Synthetic construct

<400> SEQUENCE: 30
gcaactactt cgttaaaagt taaggcaaat gtatcgggga atactgg         47

<210> SEQ ID NO 31
<211> LENGTH: 47
<212> TYPE: DNA
<213> ORGANISM: Artificial Sequence
<220> FEATURE:
<223> OTHER INFORMATION: Synthetic construct

<400> SEQUENCE: 31
ccagtattcc ccgatacatt tgccttaact tttaacgaag tagttgc         47

<210> SEQ ID NO 32
<211> LENGTH: 47
<212> TYPE: DNA
<213> ORGANISM: Artificial Sequence
<220> FEATURE:
<223> OTHER INFORMATION: Synthetic construct

<400> SEQUENCE: 32
gaaaaccgaa aagatcttct cccatcaact ggtttgacaa cagatgg         47

<210> SEQ ID NO 33
<211> LENGTH: 47
<212> TYPE: DNA
<213> ORGANISM: Artificial Sequence
<220> FEATURE:
<223> OTHER INFORMATION: Synthetic construct
```

<400> SEQUENCE: 33
ccatctgttg tcaaaccagt tgatgggaga agatcttttc ggttttc         47

<210> SEQ ID NO 34
<211> LENGTH: 56
<212> TYPE: DNA
<213> ORGANISM: Artificial Sequence
<220> FEATURE:
<223> OTHER INFORMATION: Synthetic construct

<400> SEQUENCE: 34
gtcacaaata agcgtgacac tctaccttca actggtgttg taggcaccct tgctcc    56

<210> SEQ ID NO 35
<211> LENGTH: 56
<212> TYPE: DNA
<213> ORGANISM: Artificial Sequence
<220> FEATURE:
<223> OTHER INFORMATION: Synthetic construct

<400> SEQUENCE: 35
ggagcaaggg tgcctacaac accagttgaa ggtagagtgt cacgcttatt tgtgac    56

<210> SEQ ID NO 36
<211> LENGTH: 288
<212> TYPE: PRT
<213> ORGANISM: Streptococcus pyogenes

<400> SEQUENCE: 36

Glu Thr Ala Gly Val Ser Glu Asn Ala Lys Leu Ile Val Lys Lys Thr
1               5                   10                  15

Phe Asp Ser Tyr Thr Asp Asn Glu Val Leu Met Pro Lys Ala Asp Tyr
            20                  25                  30

Thr Phe Lys Val Glu Ala Asp Ser Thr Ala Ser Gly Lys Thr Lys Asp
        35                  40                  45

Gly Leu Glu Ile Lys Pro Gly Ile Val Asn Gly Leu Thr Glu Gln Ile
    50                  55                  60

Ile Ser Tyr Thr Asn Thr Asp Lys Pro Asp Ser Lys Val Lys Ser Thr
65                  70                  75                  80

Glu Phe Asp Phe Ser Lys Val Val Phe Pro Gly Ile Gly Val Tyr Arg
                85                  90                  95

Tyr Thr Val Ser Glu Lys Gln Gly Asp Val Glu Gly Ile Thr Tyr Asp
            100                 105                 110

Thr Lys Lys Trp Thr Val Asp Val Tyr Val Gly Asn Lys Glu Gly Gly
        115                 120                 125

Gly Phe Glu Pro Lys Phe Ile Val Ser Lys Glu Gln Gly Thr Asp Val
    130                 135                 140

Lys Lys Pro Val Asn Phe Asn Asn Ser Phe Ala Thr Thr Ser Leu Lys
145                 150                 155                 160

Val Lys Lys Asn Val Ser Gly Asn Thr Gly Glu Leu Gln Lys Glu Phe
                165                 170                 175

Asp Phe Thr Leu Thr Leu Asn Glu Ser Thr Asn Phe Lys Lys Asp Gln
            180                 185                 190

Ile Val Ser Leu Gln Lys Gly Asn Glu Lys Phe Glu Val Lys Ile Gly
        195                 200                 205

Thr Pro Tyr Lys Phe Lys Leu Lys Asn Gly Glu Ser Ile Gln Leu Asp
    210                 215                 220

Lys Leu Pro Val Gly Ile Thr Tyr Lys Val Asn Glu Met Glu Ala Asn

```
                225                 230                 235                 240
Lys Asp Gly Tyr Lys Thr Thr Ala Ser Leu Lys Glu Gly Asp Gly Gln
                245                 250                 255

Ser Lys Met Tyr Gln Leu Asp Met Glu Gln Lys Thr Asp Glu Ser Ala
                260                 265                 270

Asp Glu Ile Val Val Thr Asn Lys Arg Asp Thr Gln Val Pro Thr Gly
                275                 280                 285
```

<210> SEQ ID NO 37
<211> LENGTH: 290
<212> TYPE: PRT
<213> ORGANISM: Streptococcus pyogenes

<400> SEQUENCE: 37

```
His Gly Glu Thr Val Val Asn Gly Ala Lys Leu Thr Val Thr Lys Asn
1               5                   10                  15

Leu Asp Leu Val Asn Ser Asn Ala Leu Ile Pro Asn Thr Asp Phe Thr
                20                  25                  30

Phe Lys Ile Glu Pro Asp Thr Val Asn Glu Asp Gly Asn Lys Phe
                35                  40                  45

Lys Gly Val Leu Asn Thr Pro Met Thr Lys Val Thr Tyr Thr Asn Ser
    50                  55                  60

Asp Lys Gly Gly Ser Asn Thr Lys Thr Ala Glu Phe Asp Phe Ser Glu
65                  70                  75                  80

Val Thr Phe Glu Lys Pro Gly Val Tyr Tyr Tyr Lys Val Thr Glu Glu
                85                  90                  95

Lys Ile Asp Lys Val Pro Gly Val Ser Tyr Asp Thr Thr Ser Tyr Thr
                100                 105                 110

Val Gln Val His Val Leu Trp Asn Glu Glu Gln Lys Pro Val Ala
                115                 120                 125

Thr Tyr Ile Val Gly Tyr Lys Glu Gly Ser Lys Val Pro Ile Gln Phe
                130                 135                 140

Lys Asn Ser Leu Asp Ser Thr Thr Leu Thr Val Lys Lys Val Ser
145                 150                 155                 160

Gly Thr Gly Gly Asp Arg Ser Lys Asp Phe Asn Phe Gly Leu Thr Leu
                165                 170                 175

Lys Ala Asn Gln Tyr Tyr Lys Ala Ser Glu Lys Val Met Ile Glu Lys
                180                 185                 190

Thr Thr Lys Gly Gly Gln Ala Pro Val Gln Thr Glu Ala Ser Ile Asp
                195                 200                 205

Gln Leu Tyr His Phe Thr Leu Lys Asp Gly Glu Ser Ile Lys Val Thr
                210                 215                 220

Asn Leu Pro Val Gly Val Asp Tyr Val Val Thr Glu Asp Asp Tyr Lys
225                 230                 235                 240

Ser Glu Lys Tyr Thr Thr Asn Val Glu Val Ser Pro Gln Asp Gly Ala
                245                 250                 255

Val Lys Asn Ile Ala Gly Asn Ser Glu Gln Glu Thr Ser Thr Asp
                260                 265                 270

Lys Asp Met Thr Ile Thr Phe Thr Asn Lys Lys Asp Phe Glu Val Pro
                275                 280                 285

Thr Gly
    290
```

<210> SEQ ID NO 38
<211> LENGTH: 289

<212> TYPE: PRT
<213> ORGANISM: Streptococcus pyogenes

<400> SEQUENCE: 38

Glu Thr Ala Gly Val Ser Glu Asn Ala Lys Leu Ile Val Lys Lys Thr
1               5                   10                  15

Phe Asp Ser Tyr Thr Asp Asn Glu Val Leu Met Pro Lys Ala Asp Tyr
            20                  25                  30

Thr Phe Lys Val Glu Ala Asp Ser Ser Ala Thr Asp Lys Thr Lys Asp
        35                  40                  45

Gly Leu Glu Ile Lys Pro Gly Val Thr Glu Gly Leu Thr Thr Glu Gln
50                  55                  60

Thr Ile Ala Tyr Asp Asn Ser Val Lys Pro Ser Asp Lys Ser Lys Thr
65                  70                  75                  80

Ala Thr Phe Asp Phe Ser Thr Val Lys Phe Pro Glu Val Gly Val Tyr
                85                  90                  95

Arg Tyr Thr Val Ser Glu Ile Asp Ser Lys Val Ser Gly Ile Lys Tyr
            100                 105                 110

Asp Thr Lys Thr Trp Ile Val Asp Val Tyr Val Val Asn Asp Gly Asn
        115                 120                 125

Gly Gly Phe Lys Ala Arg Tyr Ile Val Ser Lys Glu Lys Gly Gln Asn
130                 135                 140

Asp Lys Lys Pro Val Val Phe Glu Asn Ser Phe Lys Thr Thr Ser Leu
145                 150                 155                 160

Lys Val Glu Lys Gln Val Thr Gly Asn Thr Gly Glu Leu Lys Lys Asp
                165                 170                 175

Phe Asn Phe Thr Leu Thr Ile Asn Pro Asn Asp Asn Phe Val Ala Gly
            180                 185                 190

Gln Val Ile Lys Leu Glu Lys Gly Gly Ile Lys Ala Asp Val Lys Ile
        195                 200                 205

Gly Glu Pro Tyr Lys Phe Ala Leu Lys Asn Gly Glu Lys Val Thr Leu
210                 215                 220

Ser Lys Leu Pro Val Gly Val Thr Tyr Ser Ile Ile Glu Asp Glu Ala
225                 230                 235                 240

Asp Lys Asp Gly Tyr Thr Thr Asn Ala Lys Ile Thr Asp Gly Thr Ala
                245                 250                 255

Ala Pro Val Glu Tyr Lys Leu Gly Asn Gln Gln Leu Ala Asp Glu Ser
            260                 265                 270

Ala Asp Glu Ile Val Val Thr Asn Asn Arg Asp Thr Gln Val Pro Thr
        275                 280                 285

Gly

<210> SEQ ID NO 39
<211> LENGTH: 290
<212> TYPE: PRT
<213> ORGANISM: Streptococcus pyogenes

<400> SEQUENCE: 39

Glu Thr Ala Gly Val Thr Asn Gly Thr Gln Leu Thr Ile Lys Lys Thr
1               5                   10                  15

Ile Ala Asn Tyr Asn Asp Ser Glu Val Leu Met Pro Lys Ala Thr Phe
            20                  25                  30

Thr Phe Glu Val Lys Pro Asp Asn Ser Val Thr Gly Val Glu Lys Thr
        35                  40                  45

Val Asp Gly Leu Thr Ile Lys Ala Gly Ile Ala Glu Gly Leu Val Lys

```
              50                  55                  60
Thr Gly Asn Val Glu Tyr Ser Asn Thr Asp Lys Val Glu Asn Lys Asp
 65                  70                  75                  80

Lys Thr Thr Thr Phe Asp Phe Ser Thr Val Lys Phe Pro Glu Val Gly
                 85                  90                  95

Val Tyr Arg Tyr Thr Val Ser Glu Thr Asp Ser Lys Val Ser Gly Ile
            100                 105                 110

Lys Tyr Asp Thr Lys Thr Trp Ile Val Asp Val Tyr Val Val Asn Asp
            115                 120                 125

Gly Asn Gly Gly Phe Lys Ala Gln Tyr Ile Val Ser Lys Glu Lys Gly
        130                 135                 140

Gln Asn Asp Lys Lys Pro Val Val Phe Glu Asn Ser Phe Lys Thr Thr
145                 150                 155                 160

Ser Leu Lys Val Glu Lys Gln Val Thr Gly Asn Thr Gly Glu Leu Lys
                165                 170                 175

Lys Asp Phe Asn Phe Thr Leu Thr Ile Asn Pro Asn Asp Asn Phe Val
            180                 185                 190

Ala Gly Gln Val Ile Lys Leu Glu Lys Gly Gly Ile Lys Ala Asp Val
            195                 200                 205

Lys Ile Gly Glu Pro Tyr Lys Phe Ala Leu Lys Asn Gly Glu Lys Val
210                 215                 220

Thr Leu Ser Lys Leu Pro Val Gly Ile Thr Tyr Ser Ile Ile Glu Asp
225                 230                 235                 240

Asp Ala Gly Lys Asp Gly Tyr Lys Thr Thr Ala Ile Leu Lys Asp Gly
                245                 250                 255

Glu Gln Ser Ser Thr Tyr Glu Leu Gly Lys Asn Gln Lys Thr Asp Glu
                260                 265                 270

Ser Ala Asp Glu Ile Val Val Thr Asn Lys Arg Asp Thr Gln Val Pro
            275                 280                 285

Thr Gly
    290

<210> SEQ ID NO 40
<211> LENGTH: 288
<212> TYPE: PRT
<213> ORGANISM: Streptococcus pyogenes

<400> SEQUENCE: 40

Glu Thr Ala Gly Val Ile Asp Gly Ser Thr Leu Val Val Lys Lys Thr
 1               5                  10                  15

Phe Pro Ser Tyr Thr Asp Asp Asn Val Leu Met Pro Lys Ala Asp Tyr
                20                  25                  30

Ser Phe Lys Val Glu Ala Asp Asn Ala Lys Gly Lys Thr Lys Asp
            35                  40                  45

Gly Leu Asp Ile Lys Pro Gly Val Ile Asp Gly Leu Glu Asn Thr Lys
        50                  55                  60

Thr Ile Arg Tyr Ser Asn Ser Asp Lys Ile Thr Ala Lys Glu Lys Ser
 65                  70                  75                  80

Val Asn Phe Glu Phe Ala Asn Val Lys Phe Pro Gly Val Gly Val Tyr
                85                  90                  95

Arg Tyr Thr Val Ala Glu Val Asn Gly Asn Lys Ala Gly Ile Thr Tyr
            100                 105                 110

Asp Ser Gln Gln Trp Thr Val Asp Val Tyr Val Val Asn Lys Glu Gly
            115                 120                 125
```

```
Gly Gly Phe Glu Val Lys Tyr Ile Val Ser Thr Glu Val Gly Gln Ser
            130                 135                 140

Glu Lys Lys Pro Val Leu Phe Lys Asn Ser Phe Asp Thr Thr Ser Leu
145                 150                 155                 160

Lys Ile Glu Lys Gln Val Thr Gly Asn Thr Gly Glu His Gln Arg Leu
                165                 170                 175

Phe Ser Phe Thr Leu Leu Leu Thr Pro Asn Glu Cys Phe Glu Lys Gly
                180                 185                 190

Gln Val Val Asn Ile Leu Gln Gly Gly Glu Thr Lys Lys Val Val Ile
                195                 200                 205

Gly Glu Glu Tyr Ser Phe Thr Leu Lys Asp Lys Glu Ser Val Thr Leu
        210                 215                 220

Ser Gln Leu Pro Val Gly Ile Glu Tyr Lys Leu Thr Glu Glu Asp Val
225                 230                 235                 240

Thr Lys Asp Gly Tyr Lys Thr Ser Ala Thr Leu Lys Asp Gly Glu Gln
                245                 250                 255

Ser Ser Thr Tyr Glu Leu Gly Lys Asp His Lys Thr Asp Lys Ser Ala
                260                 265                 270

Asp Glu Ile Val Val Thr Asn Lys Arg Asp Thr Gln Val Pro Thr Gly
                275                 280                 285

<210> SEQ ID NO 41
<211> LENGTH: 288
<212> TYPE: PRT
<213> ORGANISM: Streptococcus pyogenes

<400> SEQUENCE: 41

Glu Thr Ala Gly Val Ile Asp Gly Ser Thr Leu Val Val Lys Lys Thr
1               5                   10                  15

Phe Pro Ser Tyr Thr Asp Asp Lys Val Leu Met Pro Lys Ala Asp Tyr
                20                  25                  30

Thr Phe Lys Val Glu Ala Asp Asn Ala Lys Gly Lys Thr Lys Asp
            35                  40                  45

Gly Leu Asp Ile Lys Pro Gly Val Ile Asp Gly Leu Glu Asn Thr Lys
        50                  55                  60

Thr Ile His Tyr Gly Asn Ser Asp Lys Thr Thr Ala Lys Glu Lys Ser
65                  70                  75                  80

Val Asn Phe Asp Phe Ala Asn Val Lys Phe Pro Gly Val Gly Val Tyr
                85                  90                  95

Arg Tyr Thr Val Ser Glu Val Asn Gly Asn Lys Ala Gly Ile Ala Tyr
                100                 105                 110

Asp Ser Gln Gln Trp Thr Val Asp Val Tyr Val Val Asn Arg Glu Asp
            115                 120                 125

Gly Gly Phe Glu Ala Lys Tyr Ile Val Ser Thr Glu Gly Gly Gln Ser
        130                 135                 140

Asp Lys Lys Pro Val Leu Phe Lys Asn Phe Asp Thr Thr Ser Leu
145                 150                 155                 160

Lys Val Thr Lys Lys Val Thr Gly Asn Thr Gly Glu His Gln Arg Ser
                165                 170                 175

Phe Ser Phe Thr Leu Leu Leu Thr Pro Asn Glu Cys Phe Glu Lys Gly
                180                 185                 190

Gln Val Val Asn Ile Leu Gln Gly Gly Glu Thr Lys Lys Val Val Ile
                195                 200                 205

Gly Glu Glu Tyr Ser Phe Thr Leu Lys Asp Lys Glu Ser Val Thr Leu
        210                 215                 220
```

```
Ser Gln Leu Pro Val Gly Ile Glu Tyr Lys Val Thr Glu Glu Asp Val
225                 230                 235                 240

Thr Lys Asp Gly Tyr Lys Thr Ser Ala Thr Leu Lys Asp Gly Asp Val
                245                 250                 255

Thr Asp Gly Tyr Asn Leu Gly Asp Ser Lys Thr Thr Asp Lys Ser Thr
            260                 265                 270

Asp Glu Ile Val Val Thr Asn Lys Arg Asp Thr Gln Val Pro Thr Gly
        275                 280                 285

<210> SEQ ID NO 42
<211> LENGTH: 286
<212> TYPE: PRT
<213> ORGANISM: Streptococcus pyogenes

<400> SEQUENCE: 42

Glu Thr Ala Gly Val Thr Gly Lys Thr Leu Pro Ile Thr Lys Ser
1               5                   10                  15

Met Ile Tyr Thr Asp Asn Glu Ile Leu Met Pro Lys Thr Thr Phe Thr
            20                  25                  30

Phe Thr Ile Glu Pro Asp Thr Thr Ala Ser Gly Lys Thr Lys Asp Gly
        35                  40                  45

Leu Glu Ile Lys Ser Gly Glu Thr Thr Gly Leu Thr Thr Lys Ala Ile
50                  55                  60

Val Ser Tyr Asp Asn Thr Asp Lys Glu Ser Ala Lys Asn Lys Thr Ser
65                  70                  75                  80

Asn Phe Asn Phe Glu Thr Val Thr Phe Ser Gly Ile Gly Ile Tyr Arg
                85                  90                  95

Tyr Thr Val Ser Glu Gln Asn Asp Gly Ile Glu Gly Ile Gln Tyr Asp
            100                 105                 110

Gly Lys Lys Trp Thr Val Asp Val Tyr Val Gly Asn Lys Glu Gly Gly
        115                 120                 125

Gly Phe Glu Pro Lys Tyr Val Val Ser Lys Glu Val Asn Ser Asp Val
130                 135                 140

Lys Lys Pro Ile Arg Phe Glu Asn Ser Phe Lys Thr Thr Ser Leu Lys
145                 150                 155                 160

Ile Glu Lys Gln Val Thr Gly Asn Thr Gly Glu Leu Gln Lys Asp Phe
                165                 170                 175

Asn Phe Thr Leu Ile Leu Glu Ala Ser Ala Leu Tyr Glu Lys Gly Gln
            180                 185                 190

Val Val Lys Ile Ile Gln Asp Gly Gln Thr Lys Asp Val Val Ile Gly
        195                 200                 205

Gln Glu Tyr Lys Phe Thr Leu His Asp His Gln Ser Ile Met Leu Ala
210                 215                 220

Lys Leu Pro Ile Gly Ile Ser Tyr Lys Leu Thr Glu Asp Lys Ala Asp
225                 230                 235                 240

Gly Tyr Thr Thr Thr Ala Thr Leu Lys Glu Gly Glu Ile Asp Ala Lys
                245                 250                 255

Glu Tyr Val Leu Gly Asn Leu Gln Lys Thr Asp Glu Ser Ala Asp Glu
            260                 265                 270

Ile Val Val Thr Asn Lys Arg Asp Thr Gln Val Pro Thr Gly
        275                 280                 285

<210> SEQ ID NO 43
<211> LENGTH: 291
<212> TYPE: PRT
```

<213> ORGANISM: Streptococcus pyogenes

<400> SEQUENCE: 43

```
Glu Thr Ala Gly Val Val Thr Gly Lys Ser Leu Gln Val Thr Lys Thr
1               5                   10                  15
Met Thr Tyr Asp Asp Glu Glu Val Leu Met Pro Glu Thr Ala Phe Thr
            20                  25                  30
Phe Thr Ile Glu Pro Asp Met Thr Ala Ser Gly Lys Glu Gly Ser Leu
        35                  40                  45
Asp Ile Lys Asn Gly Ile Val Glu Gly Leu Asp Lys Gln Val Thr Val
    50                  55                  60
Lys Tyr Lys Asn Thr Asp Lys Ser Gln Lys Thr Lys Ile Ala Gln
65                  70                  75                  80
Phe Asp Phe Ser Lys Val Lys Phe Pro Ala Ile Gly Val Tyr Arg Tyr
                85                  90                  95
Met Val Ser Glu Lys Asn Asp Lys Asp Gly Ile Thr Tyr Asp Asp
            100                 105                 110
Lys Lys Trp Thr Val Asp Val Tyr Val Gly Asn Lys Ala Asn Asn Glu
        115                 120                 125
Glu Gly Phe Glu Val Leu Tyr Ile Val Ser Lys Glu Gly Thr Ser Ser
    130                 135                 140
Thr Lys Lys Pro Ile Glu Phe Thr Asn Ser Ile Lys Thr Thr Ser Leu
145                 150                 155                 160
Lys Ile Glu Lys Gln Ile Thr Gly Asn Ala Gly Asp Arg Ser Lys Ser
                165                 170                 175
Phe Asn Phe Thr Leu Thr Leu Gln Pro Ser Glu Tyr Tyr Lys Thr Gly
            180                 185                 190
Ser Val Val Lys Ile Glu Gln Asp Gly Ser Lys Lys Asp Val Thr Ile
        195                 200                 205
Gly Thr Pro Tyr Lys Phe Thr Leu Gly His Gly Lys Ser Val Met Leu
    210                 215                 220
Ser Lys Leu Pro Ile Gly Ile Asn Tyr Tyr Leu Ser Glu Asp Glu Ala
225                 230                 235                 240
Asn Lys Asp Gly Tyr Thr Thr Thr Ala Thr Leu Lys Glu Gln Gly Lys
                245                 250                 255
Glu Lys Ser Ser Asp Phe Thr Leu Ser Thr Gln Asn Gln Lys Thr Asp
            260                 265                 270
Glu Ser Ala Asp Glu Ile Val Val Thr Asn Lys Arg Asp Thr Gln Val
        275                 280                 285
Pro Thr Gly
    290
```

<210> SEQ ID NO 44
<211> LENGTH: 286
<212> TYPE: PRT
<213> ORGANISM: Streptococcus pyogenes

<400> SEQUENCE: 44

```
Glu Thr Ala Gly Val Val Ser Ser Gly Gln Leu Thr Ile Lys Lys Ser
1               5                   10                  15
Ile Thr Asn Phe Asn Asp Asp Thr Leu Leu Met Pro Lys Thr Asp Tyr
            20                  25                  30
Thr Phe Ser Val Asn Pro Asp Ser Ala Ala Thr Gly Thr Glu Ser Asn
        35                  40                  45
Leu Pro Ile Lys Pro Gly Ile Ala Val Asn Asn Gln Asp Ile Lys Val
```

-continued

```
             50                  55                  60
Ser Tyr Ser Asn Thr Asp Lys Thr Gly Lys Glu Lys Gln Val Val
 65                  70                  75                  80

Val Asp Phe Met Lys Val Thr Phe Pro Ser Val Gly Ile Tyr Arg Tyr
                 85                  90                  95

Val Val Thr Glu Asn Lys Gly Thr Ala Glu Gly Val Thr Tyr Asp Asp
                100                 105                 110

Thr Lys Trp Leu Val Asp Val Tyr Val Gly Asn Asn Glu Lys Gly Gly
                115                 120                 125

Leu Glu Pro Lys Tyr Ile Val Ser Lys Lys Gly Asp Ser Ala Thr Lys
130                 135                 140

Glu Pro Ile Gln Phe Asn Asn Ser Phe Glu Thr Thr Ser Leu Lys Ile
145                 150                 155                 160

Glu Lys Glu Val Thr Gly Asn Thr Gly Asp His Lys Lys Ala Phe Thr
                165                 170                 175

Phe Thr Leu Thr Leu Gln Pro Asn Glu Tyr Tyr Glu Ala Ser Ser Val
                180                 185                 190

Val Lys Ile Glu Glu Asn Gly Gln Thr Lys Asp Val Lys Ile Gly Glu
                195                 200                 205

Ala Tyr Lys Phe Thr Leu Asn Asp Ser Gln Ser Val Ile Leu Ser Lys
210                 215                 220

Leu Pro Val Gly Ile Asn Tyr Lys Val Glu Glu Ala Glu Ala Asn Gln
225                 230                 235                 240

Gly Gly Tyr Thr Thr Thr Ala Thr Leu Lys Asp Gly Glu Lys Leu Ser
                245                 250                 255

Thr Tyr Asn Leu Gly Gln Glu His Lys Thr Asp Lys Thr Ala Asp Glu
                260                 265                 270

Ile Val Val Thr Asn Asn Arg Asp Thr Gln Val Pro Thr Gly
                275                 280                 285

<210> SEQ ID NO 45
<211> LENGTH: 38
<212> TYPE: DNA
<213> ORGANISM: Artificial Sequence
<220> FEATURE:
<223> OTHER INFORMATION: Synthetic construct

<400> SEQUENCE: 45
gaaaaccgaa aagatcttgt cccattgaca acagatgg                              38

<210> SEQ ID NO 46
<211> LENGTH: 38
<212> TYPE: DNA
<213> ORGANISM: Artificial Sequence
<220> FEATURE:
<223> OTHER INFORMATION: Synthetic construct

<400> SEQUENCE: 46
ccatctgttg tcaatgggac aagatctttt cggttttc                              38

<210> SEQ ID NO 47
<211> LENGTH: 9
<212> TYPE: PRT
<213> ORGANISM: Artificial Sequence
<220> FEATURE:
<223> OTHER INFORMATION: Synthetic construct

<400> SEQUENCE: 47

Gly Tyr Pro Asp Tyr Ser Pro Leu Lys
```

```
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic construct

<400> SEQUENCE: 48

Ala Glu Glu Gln Ser Val Pro Asn Lys
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic construct

<400> SEQUENCE: 49

Val Asn Leu Asp Gly Ser Lys
1               5

<210> SEQ ID NO 50
<211> LENGTH: 11
<212> TYPE: PRT
<213> ORGANISM: Artificial Sequence
<220> FEATURE:
<223> OTHER INFORMATION: Synthetic construct

<400> SEQUENCE: 50

Lys Leu Glu Gly Thr Asn Glu Asn Phe Ile Lys
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic construct

<400> SEQUENCE: 51

Leu Glu Gly Thr Asn Glu Asn Phe Ile Lys
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic construct

<400> SEQUENCE: 52

Ile Glu Asp Gly Gln Leu Gln Gln Asn Ile Leu Arg
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic construct

<400> SEQUENCE: 53

Ile Leu Tyr Asn Gly Tyr Pro Asn Asp Arg
1               5                   10
```

```
<210> SEQ ID NO 54
<211> LENGTH: 13
<212> TYPE: PRT
<213> ORGANISM: Artificial Sequence
<220> FEATURE:
<223> OTHER INFORMATION: Synthetic construct

<400> SEQUENCE: 54

Gly Ile Asp Pro Leu Asn Ala Ile Leu Val Thr Gln Asn
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic construct

<400> SEQUENCE: 55

Ala Phe Gln Gln Glu Glu Thr Asp Leu Lys
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic construct

<400> SEQUENCE: 56

Gln Leu Ser Ile Phe Gln Ser Ser Asp Lys
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic construct

<400> SEQUENCE: 57

Tyr Pro Tyr Asp Val Pro Asp Tyr Ala Thr Glu Lys
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Synthetic construct

<400> SEQUENCE: 58

Lys Tyr Ala Glu Gly Asp Tyr Ser Lys
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic construct

<400> SEQUENCE: 59

Tyr Ala Glu Gly Asp Tyr Ser Lys
1               5
```

```
<210> SEQ ID NO 60
<211> LENGTH: 8
<212> TYPE: PRT
<213> ORGANISM: Artificial Sequence
<220> FEATURE:
<223> OTHER INFORMATION: Synthetic construct

<400> SEQUENCE: 60

Leu Leu Glu Gly Ala Thr Leu Lys
1               5

<210> SEQ ID NO 61
<211> LENGTH: 12
<212> TYPE: PRT
<213> ORGANISM: Artificial Sequence
<220> FEATURE:
<223> OTHER INFORMATION: Synthetic construct

<400> SEQUENCE: 61

Leu Ala Gln Ile Glu Gly Ser Gly Phe Gln Glu Lys
1               5                   10

<210> SEQ ID NO 62
<211> LENGTH: 6
<212> TYPE: PRT
<213> ORGANISM: Artificial Sequence
<220> FEATURE:
<223> OTHER INFORMATION: Synthetic construct

<400> SEQUENCE: 62

Ile Phe Asp Ser Asn Lys
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic construct

<400> SEQUENCE: 63

Gly Val Ala Thr Pro Ile Thr Phe Lys
1               5

<210> SEQ ID NO 64
<211> LENGTH: 12
<212> TYPE: PRT
<213> ORGANISM: Artificial Sequence
<220> FEATURE:
<223> OTHER INFORMATION: Synthetic construct

<400> SEQUENCE: 64

Asn Lys Glu Gly Gln Phe Val Glu Asn Gln Asn Lys
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic construct

<400> SEQUENCE: 65

Glu Gly Gln Phe Val Glu Asn Gln Asn Lys
1               5                   10
```

-continued

```
<210> SEQ ID NO 66
<211> LENGTH: 11
<212> TYPE: PRT
<213> ORGANISM: Artificial Sequence
<220> FEATURE:
<223> OTHER INFORMATION: Synthetic construct

<400> SEQUENCE: 66

Tyr Thr His Val Ser Gly Tyr Asp Leu Tyr Lys
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Synthetic construct

<400> SEQUENCE: 67

Asp Lys Asp Ala Asp Phe Phe Leu Lys
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic construct

<400> SEQUENCE: 68

Asp Ala Asp Phe Phe Leu Lys
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic construct

<400> SEQUENCE: 69

Thr Leu Thr Glu Ala Gln Phe Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic construct

<400> SEQUENCE: 70

Gly Tyr His Gly Phe Asp Lys
1               5

<210> SEQ ID NO 71
<211> LENGTH: 10
<212> TYPE: PRT
<213> ORGANISM: Artificial Sequence
<220> FEATURE:
<223> OTHER INFORMATION: Synthetic construct

<400> SEQUENCE: 71

Gln Ala Pro Ile Ile Pro Ile Thr His Lys
1               5                   10

<210> SEQ ID NO 72
```

```
<211> LENGTH: 10
<212> TYPE: PRT
<213> ORGANISM: Artificial Sequence
<220> FEATURE:
<223> OTHER INFORMATION: Synthetic construct

<400> SEQUENCE: 72

Thr Val Thr Gly Thr Ile Ala Asp Lys Lys
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic construct

<400> SEQUENCE: 73

Glu Thr Ala Gly Val Ser Glu Asn Ala Lys
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic construct

<400> SEQUENCE: 74

Asp Gly Leu Glu Ile Lys Pro Gly Ile Val Asn
1               5                   10

<210> SEQ ID NO 75
<211> LENGTH: 8
<212> TYPE: PRT
<213> ORGANISM: Artificial Sequence
<220> FEATURE:
<223> OTHER INFORMATION: Synthetic construct

<400> SEQUENCE: 75

Ser Thr Glu Phe Asp Phe Ser Lys
1               5

<210> SEQ ID NO 76
<211> LENGTH: 10
<212> TYPE: PRT
<213> ORGANISM: Artificial Sequence
<220> FEATURE:
<223> OTHER INFORMATION: Synthetic construct

<400> SEQUENCE: 76

Val Val Phe Pro Gly Ile Gly Val Tyr Arg
1               5                   10

<210> SEQ ID NO 77
<211> LENGTH: 6
<212> TYPE: PRT
<213> ORGANISM: Artificial Sequence
<220> FEATURE:
<223> OTHER INFORMATION: Synthetic construct

<400> SEQUENCE: 77

Tyr Thr Val Ser Glu Lys
1               5

<210> SEQ ID NO 78
<211> LENGTH: 12
```

```
<212> TYPE: PRT
<213> ORGANISM: Artificial Sequence
<220> FEATURE:
<223> OTHER INFORMATION: Synthetic construct

<400> SEQUENCE: 78

Gln Gly Asp Val Glu Gly Ile Thr Tyr Asp Thr Lys
1               5                   10

<210> SEQ ID NO 79
<211> LENGTH: 9
<212> TYPE: PRT
<213> ORGANISM: Artificial Sequence
<220> FEATURE:
<223> OTHER INFORMATION: Synthetic construct

<400> SEQUENCE: 79

Thr Val Asp Val Tyr Val Gly Asn Lys
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic construct

<400> SEQUENCE: 80

Glu Gly Gly Gly Phe Glu Pro Lys
1               5

<210> SEQ ID NO 81
<211> LENGTH: 12
<212> TYPE: PRT
<213> ORGANISM: Artificial Sequence
<220> FEATURE:
<223> OTHER INFORMATION: Synthetic construct

<400> SEQUENCE: 81

Lys Asn Val Ser Gly Asn Thr Gly Glu Leu Gln Lys
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic construct

<400> SEQUENCE: 82

Asp Glu Ser Ala Asp Glu Ile Val Val Thr Asn Lys
1               5                   10

<210> SEQ ID NO 83
<211> LENGTH: 9
<212> TYPE: PRT
<213> ORGANISM: Artificial Sequence
<220> FEATURE:
<223> OTHER INFORMATION: Synthetic construct

<400> SEQUENCE: 83

Lys Asp Gln Ile Val Ser Leu Gln Lys
1               5

<210> SEQ ID NO 84
<211> LENGTH: 8
<212> TYPE: PRT
```

<213> ORGANISM: Artificial Sequence
<220> FEATURE:
<223> OTHER INFORMATION: Synthetic construct

<400> SEQUENCE: 84

Asp Gln Ile Val Ser Leu Gln Lys
1               5

<210> SEQ ID NO 85
<211> LENGTH: 11
<212> TYPE: PRT
<213> ORGANISM: Artificial Sequence
<220> FEATURE:
<223> OTHER INFORMATION: Synthetic construct

<400> SEQUENCE: 85

Leu Lys Asn Gly Glu Ser Ile Gln Leu Asp Lys
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Synthetic construct

<400> SEQUENCE: 86

Asn Gly Glu Ser Ile Gln Leu Asp Lys
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic construct

<400> SEQUENCE: 87

Leu Pro Val Gly Ile Thr Tyr Lys
1               5

<210> SEQ ID NO 88
<211> LENGTH: 12
<212> TYPE: PRT
<213> ORGANISM: Artificial Sequence
<220> FEATURE:
<223> OTHER INFORMATION: Synthetic construct

<400> SEQUENCE: 88

Val Asn Glu Met Glu Ala Asn Lys Asp Gly Tyr Lys
1               5                   10

<210> SEQ ID NO 89
<211> LENGTH: 1092
<212> TYPE: PRT
<213> ORGANISM: Streptococcus pyogenes

<400> SEQUENCE: 89

Ala Thr Gly Ala Ala Ala Ala Gly Ala Thr Ala Thr Thr Thr Ala
1               5                   10                  15

Thr Thr Thr Thr Thr Thr Thr Gly Thr Cys Thr Ala Cys Ala Thr
                20                  25                  30

Ala Thr Thr Thr Thr Cys Thr Gly Cys Gly Gly Thr Gly Thr Cys
            35                  40                  45

Ala Gly Thr Gly Cys Cys Gly Gly Gly Cys Gly Ala Thr Ala Cys Cys

```
    50                  55                  60

Cys Gly Gly Ala Ala Ala Cys Thr Ala Cys Ala Gly Thr Ala Gly Gly
65                  70                  75                  80

Thr Ala Ala Thr Cys Thr Gly Ala Cys Gly Ala Ala Gly Ala Gly Thr
                85                  90                  95

Thr Thr Thr Cys Ala Ala Gly Cys Cys Cys Cys Thr Cys Gly Thr Cys
            100                 105                 110

Thr Gly Gly Ala Thr Ala Gly Ala Ala Gly Cys Gly Thr Ala Cys Ala
        115                 120                 125

Ala Thr Cys Ala Cys Cys Ala Ala Thr Ala Thr Ala Thr Ala Ala Cys
    130                 135                 140

Ala Thr Cys Thr Thr Thr Ala Cys Gly Ala Ala Thr Cys Ala Thr Gly
145                 150                 155                 160
Thr Gly Gly Cys Thr Gly Gly Ala Thr Ala Thr Ala Gly Thr Thr Thr
                165                 170                 175
Gly Ala Gly Thr Cys Ala Thr Ala Gly Cys Thr Thr Ala Thr Ala Thr
            180                 185                 190

Gly Ala Cys Ala Gly Gly Ala Thr Thr Gly Thr Thr Thr Thr Thr Thr
        195                 200                 205

Thr Ala Thr Gly Thr Ala Cys Ala Thr Cys Cys Thr Cys Gly Thr Cys
    210                 215                 220

Gly Ala Ala Thr Cys Cys Gly Gly Thr Thr Ala Ala Thr Gly Gly Thr
225                 230                 235                 240

Gly Cys Thr Thr Gly Cys Cys Cys Ala Ala Cys Cys Ala Thr Thr Gly
                245                 250                 255

Gly Ala Ala Cys Ala Thr Cys Thr Gly Gly Ala Gly Thr Thr Cys Ala
            260                 265                 270

Ala Thr Ala Cys Gly Gly Thr Ala Cys Thr Ala Cys Ala Ala Cys Cys
        275                 280                 285

Ala Thr Ala Ala Cys Cys Thr Thr Gly Cys Ala Gly Thr Thr Thr Ala
    290                 295                 300

Cys Ala Gly Ala Ala Ala Ala Ala Ala Gly Ala Ala Gly Thr Cys Thr
305                 310                 315                 320

Gly Ala Thr Ala Ala Ala Ala Ala Gly Ala Ala Ala Thr Ala Thr Thr
                325                 330                 335

Ala Ala Thr Cys Thr Thr Gly Cys Ala Gly Gly Thr Ala Ala Thr Ala
            340                 345                 350

Ala Gly Ala Ala Ala Cys Cys Ala Ala Thr Ala Thr Gly Gly Gly Ala
        355                 360                 365

Gly Ala Ala Thr Cys Ala Gly Ala Gly Thr Thr Gly Cys Gly Ala Cys
    370                 375                 380

Thr Thr Thr Ala Gly Cys Ala Ala Thr Cys Thr Ala Ala Thr Gly Gly
385                 390                 395                 400

Thr Gly Thr Thr Gly Ala Ala Thr Thr Cys Gly Ala Ala Gly Thr Cys
                405                 410                 415

Thr Thr Gly Gly Ala Gly Cys Thr Gly Thr Gly Gly Gly Gly Cys Thr
            420                 425                 430

Cys Ala Cys Gly Gly Ala Ala Ala Thr Gly Cys Thr Ala Ala Cys Gly
        435                 440                 445

Gly Ala Ala Cys Ala Cys Thr Thr Cys Thr Ala Ala Ala Thr Cys Thr
    450                 455                 460

Gly Thr Ala Thr Ala Thr Cys Cys Cys Thr Gly Cys Ala Gly Gly Ala
465                 470                 475                 480
```

```
Gly Ala Ala Ala Thr Cys Ala Ala Cys Ala Ala Thr Thr Gly Cys
                485                 490                 495

Cys Thr Thr Thr Thr Gly Gly Ala Gly Gly Ala Thr Ala Thr Gly
                500                 505                 510

Gly Gly Ala Gly Gly Cys Ala Ala Cys Thr Cys Thr Gly Ala Thr Cys
                515                 520                 525

Thr Thr Ala Cys Gly Cys Thr Thr Ala Thr Cys Ala Ala Gly Ala Thr
        530                 535                 540

Ala Thr Gly Gly Cys Gly Ala Ala Gly Thr Cys Ala Gly Thr Ala Gly
545                 550                 555                 560

Cys Ala Cys Cys Cys Ala Thr Thr Ala Cys Gly Gly Cys Ala Ala Thr
                565                 570                 575

Thr Ala Thr Ala Cys Cys Gly Thr Ala Ala Thr Ala Thr Thr Ala
                580                 585                 590

Cys Gly Gly Thr Thr Gly Ala Thr Thr Thr Ala Ala Cys Thr Gly Ala
        595                 600                 605

Thr Ala Ala Ala Gly Gly Thr Ala Ala Thr Ala Thr Thr Cys Ala Gly
        610                 615                 620

Gly Thr Ala Thr Gly Gly Cys Thr Thr Cys Cys Ala Gly Gly Gly Thr
625                 630                 635                 640

Thr Thr Cys Ala Cys Ala Gly Cys Ala Ala Cys Cys Cys Gly Cys Gly
                645                 650                 655

Thr Gly Thr Ala Gly Ala Cys Cys Thr Gly Ala Ala Thr Cys Thr Gly
        660                 665                 670

Cys Gly Cys Cys Cys Thr Ala Thr Cys Gly Gly Thr Ala Ala Thr Thr
        675                 680                 685

Ala Thr Ala Ala Ala Thr Ala Thr Ala Gly Thr Gly Gly Thr Ala Gly
690                 695                 700

Thr Ala Ala Thr Thr Cys Ala Cys Thr Cys Gly Ala Cys Ala Thr Gly
705                 710                 715                 720

Thr Gly Thr Thr Thr Cys Thr Ala Gly Ala Thr Gly Gly Ala Thr
                725                 730                 735

Ala Thr Ala Gly Thr Ala Cys Ala Ala Ala Cys Ala Gly Thr Gly Ala
        740                 745                 750

Thr Ala Gly Cys Ala Thr Gly Gly Thr Ala Ala Thr Ala Ala Ala Gly
        755                 760                 765

Thr Thr Cys Cys Ala Gly Gly Ala Thr Gly Ala Thr Ala Ala Thr Cys
770                 775                 780

Cys Thr Ala Cys Cys Ala Ala Thr Thr Cys Ala Thr Cys Thr Gly Ala
785                 790                 795                 800

Ala Thr Ala Thr Ala Ala Thr Cys Thr Thr Thr Ala Thr Ala Ala Gly
                805                 810                 815

Ala Thr Ala Gly Gly Gly Gly Gly Cys Ala Cys Thr Gly Ala Ala Ala
                820                 825                 830

Ala Ala Thr Thr Ala Cys Cys Ala Thr Ala Gly Cys Thr Gly Thr
                835                 840                 845

Thr Thr Cys Ala Cys Thr Gly Cys Thr Thr Ala Thr Gly Gly Gly Ala
        850                 855                 860

Gly Ala Ala Ala Ala Ala Thr Ala Thr Thr Thr Ala Thr Cys
865                 870                 875                 880

Cys Ala Gly Thr Gly Ala Ala Thr Gly Gly Thr Cys Ala Ala Thr Cys
                885                 890                 895
```

```
Ala Thr Thr Thr Ala Cys Thr Ala Thr Cys Ala Ala Thr Gly Ala Cys
                900                 905                 910

Ala Gly Thr Ala Gly Thr Gly Thr Ala Cys Thr Cys Gly Ala Ala Ala
            915                 920                 925

Cys Ala Ala Ala Cys Thr Gly Gly Ala Ala Thr Cys Gly Ala Gly Thr
        930                 935                 940

Ala Ala Cys Cys Gly Cys Ala Gly Thr Gly Cys Thr Ala Thr Gly
945                 950                 955                 960

Cys Cys Gly Gly Ala Ala Gly Thr Thr Ala Thr Gly Thr Thr Cys
                965                 970                 975

Cys Ala Gly Thr Ala Thr Ala Thr Gly Cys Thr Gly Gly Cys Cys
            980                 985                 990

Ala Gly Cys Ala Ala Gly Ala Thr Thr Gly Cys Thr Ala Thr Thr Ala
        995                1000                1005

Ala Ala Thr Gly Cys Thr Gly Ala Thr Gly Thr Ala Ala Ala Thr
    1010                1015                1020

Gly Cys Thr Cys Cys Gly Ala Thr Gly Cys Ala Gly Gly Ala
    1025                1030                1035

Cys Ala Gly Thr Ala Thr Thr Cys Ala Gly Gly Ala Cys Ala Gly
    1040                1045                1050

Ala Thr Ala Thr Ala Thr Ala Thr Ala Ala Cys Ala Thr Thr Thr
    1055                1060                1065

Ala Cys Ala Cys Cys Cys Ala Gly Thr Gly Thr Cys Gly Ala Ala
    1070                1075                1080

Ala Ala Thr Thr Thr Ala Thr Gly Ala
    1085                1090

<210> SEQ ID NO 90
<211> LENGTH: 363
<212> TYPE: PRT
<213> ORGANISM: Streptococcus pyogenes

<400> SEQUENCE: 90

Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
            20                  25                  30

Phe Gln Ala Pro Arg Leu Asp Arg Ser Val Gln Ser Pro Ile Tyr Asn
        35                  40                  45

Ile Phe Thr Asn His Val Ala Gly Tyr Ser Leu Ser His Ser Leu Tyr
    50                  55                  60

Asp Arg Ile Val Phe Leu Cys Thr Ser Ser Ser Asn Pro Val Asn Gly
65                  70                  75                  80

Ala Cys Pro Thr Ile Gly Thr Ser Gly Val Gln Tyr Gly Thr Thr Thr
                85                  90                  95

Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
        115                 120                 125

Phe Ser Asn Leu Met Val Leu Asn Ser Lys Ser Trp Ser Cys Gly Ala
    130                 135                 140

His Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175
```

```
Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
            195                 200                 205

Val Trp Leu Pro Gly Phe His Ser Asn Pro Arg Val Asp Leu Asn Leu
    210                 215                 220

Arg Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Asn Ser Ser Glu Tyr Asn Leu Tyr Lys
                260                 265                 270

Ile Gly Gly Thr Glu Lys Leu Pro Tyr Ala Val Ser Leu Leu Met Gly
            275                 280                 285

Glu Lys Ile Phe Tyr Pro Val Asn Gly Gln Ser Phe Thr Ile Asn Asp
            290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
                340                 345                 350

Tyr Ile Thr Phe Thr Pro Ser Val Glu Asn Leu
            355                 360

<210> SEQ ID NO 91
<211> LENGTH: 2295
<212> TYPE: PRT
<213> ORGANISM: Streptococcus pyogenes

<400> SEQUENCE: 91

Ala Thr Gly Ala Ala Ala Ala Cys Gly Ala Ala Ala Gly
1               5                   10                  15

Thr Gly Thr Thr Ala Ala Thr Ala Cys Cys Ala Thr Ala Ala Thr
            20                  25                  30

Gly Gly Cys Ala Thr Gly Thr Cys Thr Ala Cys Gly Ala Thr Ala
            35                  40                  45

Thr Thr Ala Gly Thr Thr Thr Cys Ala Ala Gly Cys Ala Cys Ala Gly
    50                  55                  60

Gly Thr Ala Ala Thr Thr Thr Ala Gly Ala Gly Gly Thr Gly Ala Thr
65                  70                  75                  80

Thr Cys Ala Gly Gly Cys Ala Gly Ala Ala Gly Thr Thr Ala Ala Ala
                85                  90                  95

Cys Ala Gly Gly Ala Gly Ala Ala Cys Cys Gly Gly Thr Thr Ala Thr
            100                 105                 110

Thr Ala Ala Ala Thr Gly Ala Ala Thr Cys Ala Gly Ala Ala Thr Cys
            115                 120                 125

Ala Ala Gly Thr Thr Cys Cys Cys Ala Gly Gly Gly Thr Thr Ala
            130                 135                 140

Cys Thr Ala Gly Gly Ala Thr Ala Cys Thr Ala Thr Thr Thr Ala
145                 150                 155                 160

Gly Thr Gly Ala Thr Thr Gly Ala Ala Thr Thr Thr Cys Ala
            165                 170                 175

Ala Gly Cys Ala Cys Cys Cys Ala Thr Gly Gly Thr Gly Gly Thr Thr
```

-continued

```
                180                 185                 190
Ala Cys Cys Thr Cys Thr Thr Cys Thr Ala Cys Thr Ala Cys Ala Gly
            195                 200                 205
Gly Gly Gly Ala Thr Thr Ala Thr Cys Thr Ala Thr Cys Cys
        210                 215                 220
Thr Ala Gly Thr Thr Cys Thr Gly Ala Gly Thr Ala Gly Ala Ala
225                 230                 235                 240
Ala Ala Thr Ala Thr Thr Cys Cys Ala Thr Cys Gly Gly Ala Ala Ala
                245                 250                 255
Ala Cys Cys Ala Ala Thr Ala Thr Thr Thr Cys Ala Ala Thr Cys
            260                 265                 270
Thr Gly Cys Thr Ala Thr Thr Gly Gly Thr Cys Ala Gly Gly Ala
        275                 280                 285
Thr Thr Thr Ala Thr Cys Ala Ala Ala Gly Thr Thr Ala Ala Gly Ala
        290                 295                 300
Ala Gly Ala Gly Thr Gly Ala Thr Gly Ala Ala Thr Ala Thr Ala Cys
305                 310                 315                 320
Ala Thr Thr Thr Gly Cys Thr Ala Cys Thr Thr Cys Cys Gly Cys Thr
                325                 330                 335
Gly Ala Thr Ala Ala Thr Cys Ala Thr Gly Thr Ala Ala Cys Ala Ala
                340                 345                 350
Thr Gly Thr Gly Gly Gly Thr Ala Gly Ala Thr Gly Ala Cys Cys Ala
            355                 360                 365
Ala Gly Ala Ala Gly Thr Gly Ala Thr Ala Ala Thr Ala Ala Ala
        370                 375                 380
Gly Cys Thr Thr Cys Thr Ala Ala Thr Cys Thr Ala Ala Cys Ala
385                 390                 395                 400
Ala Ala Ala Thr Cys Ala Gly Ala Thr Thr Ala Gly Ala Ala Ala Ala
                405                 410                 415
Ala Gly Gly Ala Ala Gly Ala Thr Thr Ala Thr Ala Thr Cys Ala Ala
            420                 425                 430
Ala Thr Ala Ala Ala Ala Thr Thr Cys Ala Ala Thr Ala Thr Cys
        435                 440                 445
Ala Ala Cys Gly Ala Gly Ala Ala Ala Thr Cys Cys Thr Ala Cys
        450                 455                 460
Thr Gly Ala Ala Ala Ala Ala Gly Gly Ala Thr Thr Gly Gly Ala Thr
465                 470                 475                 480
Thr Thr Cys Ala Ala Gly Thr Thr Gly Thr Ala Cys Thr Gly Gly Ala
                485                 490                 495
Cys Cys Gly Ala Thr Thr Cys Thr Cys Ala Ala Ala Thr Ala Ala
            500                 505                 510
Ala Ala Ala Ala Gly Ala Ala Gly Thr Gly Ala Thr Thr Cys Thr
            515                 520                 525
Ala Gly Thr Gly Ala Thr Ala Ala Cys Thr Ala Cys Ala Ala Thr
            530                 535                 540
Thr Gly Cys Cys Ala Gly Ala Ala Thr Ala Ala Ala Cys Ala
545                 550                 555                 560
Ala Ala Ala Ala Thr Cys Thr Cys Gly Ala Ala Cys Thr Cys Ala
                565                 570                 575
Ala Gly Ala Ala Ala Ala Ala Gly Cys Gly Ala Ala Gly Thr Ala
            580                 585                 590
Cys Ala Ala Gly Thr Gly Cys Thr Gly Gly Ala Cys Cys Thr Ala Cys
            595                 600                 605
```

Gly Gly Thr Thr Cys Cys Ala Gly Ala Cys Cys Gly Thr Gly Ala Cys
610 615 620

Ala Ala Thr Gly Ala Thr Gly Gly Ala Ala Thr Cys Cys Cys Thr Gly
625 630 635 640

Ala Thr Thr Cys Ala Thr Thr Ala Gly Ala Gly Gly Thr Ala Gly Ala
645 650 655

Ala Gly Gly Ala Thr Ala Thr Ala Cys Gly Gly Thr Thr Gly Ala Thr
660 665 670

Gly Thr Cys Ala Ala Ala Ala Ala Thr Ala Ala Ala Ala Gly Ala Ala
675 680 685

Cys Thr Thr Thr Thr Cys Thr Thr Thr Cys Ala Cys Cys Ala Thr Gly
690 695 700

Gly Ala Thr Thr Thr Cys Thr Ala Ala Thr Ala Thr Thr Cys Ala Thr
705 710 715 720

Gly Ala Ala Ala Ala Gly Ala Ala Ala Gly Gly Ala Thr Thr Ala Ala
725 730 735

Cys Cys Ala Ala Ala Thr Ala Thr Ala Ala Ala Thr Cys Ala Thr Cys
740 745 750

Thr Cys Cys Thr Gly Ala Ala Ala Ala Ala Thr Gly Gly Ala Gly Cys
755 760 765

Ala Cys Gly Gly Cys Thr Thr Cys Thr Gly Ala Thr Cys Cys Gly Thr
770 775 780

Ala Cys Ala Gly Thr Gly Ala Thr Thr Thr Cys Gly Ala Ala Ala Ala
785 790 795 800

Gly Gly Thr Thr Ala Cys Ala Gly Gly Ala Cys Gly Gly Ala Thr Thr
805 810 815

Gly Ala Thr Ala Ala Gly Ala Ala Thr Gly Thr Ala Thr Cys Ala Cys
820 825 830

Cys Ala Gly Ala Gly Gly Cys Ala Ala Gly Ala Cys Ala Cys Cys Cys
835 840 845

Cys Cys Thr Thr Gly Thr Gly Gly Cys Ala Gly Cys Thr Thr Ala Thr
850 855 860

Cys Cys Gly Ala Thr Thr Gly Thr Ala Cys Ala Thr Gly Thr Ala Gly
865 870 875 880

Ala Thr Ala Thr Gly Gly Ala Gly Ala Ala Thr Ala Thr Thr Ala Thr
885 890 895

Thr Cys Thr Cys Thr Cys Ala Ala Ala Ala Ala Ala Thr Gly Ala Gly
900 905 910

Gly Ala Thr Cys Ala Ala Thr Cys Cys Ala Cys Ala Cys Ala Gly Ala
915 920 925

Ala Thr Ala Cys Thr Gly Ala Thr Ala Gly Thr Cys Ala Ala Ala Cys
930 935 940

Gly Ala Gly Ala Ala Cys Ala Ala Thr Ala Ala Gly Thr Ala Ala Ala
945 950 955 960

Ala Ala Thr Ala Cys Thr Thr Cys Thr Ala Cys Ala Ala Gly Thr Ala
965 970 975

Gly Gly Ala Cys Ala Cys Ala Thr Ala Cys Thr Ala Gly Thr Gly Ala
980 985 990

Ala Gly Thr Ala Cys Ala Thr Gly Gly Ala Ala Ala Thr Gly Cys Ala
995 1000 1005

Gly Ala Ala Gly Thr Gly Cys Ala Thr Gly Cys Gly Thr Cys Gly
1010 1015 1020

-continued

```
Thr Thr Cys Thr Thr Thr Gly Ala Thr Ala Thr Gly Gly Thr
    1025                1030                1035

Gly Gly Gly Ala Gly Thr Gly Thr Ala Thr Cys Thr Gly Cys Ala
    1040                1045                1050

Gly Gly Ala Thr Thr Ala Gly Thr Ala Ala Thr Thr Cys Gly
    1055                1060                1065

Ala Ala Thr Thr Cys Ala Ala Gly Thr Ala Cys Gly Gly Thr Cys
    1070                1075                1080

Gly Cys Ala Ala Thr Thr Gly Ala Thr Cys Ala Thr Thr Cys Ala
    1085                1090                1095

Cys Thr Ala Thr Cys Thr Cys Thr Ala Gly Cys Ala Gly Gly Gly
    1100                1105                1110

Gly Ala Ala Ala Gly Ala Ala Cys Thr Thr Gly Gly Gly Cys Thr
    1115                1120                1125

Gly Ala Ala Ala Cys Ala Ala Thr Gly Gly Thr Thr Thr Ala
    1130                1135                1140

Ala Ala Thr Ala Cys Cys Gly Cys Thr Gly Ala Thr Ala Cys Ala
    1145                1150                1155

Gly Cys Ala Ala Gly Ala Thr Thr Ala Ala Ala Thr Gly Cys Cys
    1160                1165                1170

Ala Ala Thr Ala Thr Thr Ala Gly Ala Thr Ala Thr Gly Thr Ala
    1175                1180                1185

Ala Ala Thr Ala Cys Thr Gly Gly Gly Ala Cys Gly Gly Cys Thr
    1190                1195                1200

Cys Cys Ala Ala Thr Cys Thr Ala Cys Ala Ala Cys Gly Thr Gly
    1205                1210                1215

Thr Thr Ala Cys Cys Ala Ala Cys Gly Ala Cys Thr Thr Cys Gly
    1220                1225                1230

Thr Thr Ala Gly Thr Gly Thr Thr Ala Gly Gly Ala Ala Ala Ala
    1235                1240                1245

Ala Ala Thr Cys Ala Ala Ala Cys Ala Cys Thr Cys Gly Cys Gly
    1250                1255                1260

Ala Cys Ala Ala Thr Thr Ala Ala Ala Gly Cys Thr Ala Ala Gly
    1265                1270                1275

Gly Ala Ala Ala Ala Cys Cys Ala Ala Thr Thr Ala Ala Gly Thr
    1280                1285                1290

Cys Ala Ala Ala Thr Ala Cys Thr Thr Gly Cys Ala Cys Cys Thr
    1295                1300                1305

Ala Ala Thr Ala Ala Thr Thr Ala Thr Thr Ala Thr Cys Cys Thr
    1310                1315                1320

Thr Cys Thr Ala Ala Ala Ala Cys Thr Thr Gly Gly Cys Gly
    1325                1330                1335

Cys Cys Ala Ala Thr Cys Gly Cys Ala Thr Thr Ala Ala Ala Thr
    1340                1345                1350

Gly Cys Ala Cys Ala Ala Gly Ala Cys Gly Ala Thr Thr Thr Cys
    1355                1360                1365

Ala Gly Thr Thr Cys Thr Ala Cys Thr Cys Cys Ala Ala Thr Thr
    1370                1375                1380

Ala Cys Ala Ala Thr Gly Ala Ala Thr Thr Ala Cys Ala Ala Thr
    1385                1390                1395

Cys Ala Ala Thr Thr Thr Cys Thr Thr Gly Ala Gly Thr Thr Ala
    1400                1405                1410

Gly Ala Ala Ala Ala Ala Ala Cys Gly Ala Ala Ala Cys Ala Ala
```

```
            1415                1420                1425

Thr Thr Ala Ala Gly Ala Thr Thr Ala Gly Ala Thr Ala Cys Gly
            1430                1435                1440

Gly Ala Thr Cys Ala Ala Gly Thr Ala Thr Ala Thr Gly Gly Gly
            1445                1450                1455

Ala Ala Thr Ala Thr Ala Gly Cys Ala Ala Cys Ala Thr Ala Cys
            1460                1465                1470

Ala Ala Thr Thr Thr Thr Gly Ala Ala Ala Ala Thr Gly Gly Ala
            1475                1480                1485

Ala Gly Ala Gly Thr Gly Ala Gly Gly Gly Thr Gly Gly Ala Thr
            1490                1495                1500

Ala Cys Ala Gly Gly Cys Thr Cys Gly Ala Ala Cys Thr Gly Gly
            1505                1510                1515

Ala Gly Thr Gly Ala Ala Gly Thr Gly Thr Thr Ala Cys Cys Gly
            1520                1525                1530

Cys Ala Ala Ala Thr Thr Cys Ala Ala Gly Ala Ala Ala Cys Ala
            1535                1540                1545

Ala Cys Thr Gly Cys Ala Cys Gly Thr Ala Thr Cys Ala Thr Thr
            1550                1555                1560

Thr Thr Thr Ala Ala Thr Gly Gly Ala Ala Ala Ala Gly Ala Thr
            1565                1570                1575

Thr Thr Ala Ala Ala Thr Cys Thr Gly Gly Thr Ala Gly Ala Ala
            1580                1585                1590

Ala Gly Gly Cys Gly Gly Ala Thr Ala Gly Cys Gly Gly Cys Gly
            1595                1600                1605

Gly Thr Thr Ala Ala Thr Cys Cys Thr Ala Gly Thr Gly Ala Thr
            1610                1615                1620

Cys Cys Ala Thr Thr Ala Gly Ala Ala Ala Cys Gly Ala Cys Thr
            1625                1630                1635

Ala Ala Ala Cys Cys Gly Gly Ala Thr Ala Thr Gly Ala Cys Ala
            1640                1645                1650

Thr Thr Ala Ala Ala Ala Gly Ala Ala Gly Cys Cys Cys Thr Thr
            1655                1660                1665

Ala Ala Ala Ala Thr Ala Gly Cys Ala Thr Thr Thr Gly Gly Ala
            1670                1675                1680

Thr Thr Thr Ala Ala Cys Gly Ala Ala Cys Cys Gly Ala Ala Thr
            1685                1690                1695

Gly Gly Ala Ala Ala Cys Thr Thr Ala Cys Ala Ala Thr Ala Thr
            1700                1705                1710

Cys Ala Ala Gly Gly Gly Ala Ala Ala Gly Ala Cys Ala Thr Ala
            1715                1720                1725

Ala Cys Cys Gly Ala Ala Thr Thr Thr Gly Ala Thr Thr Thr Thr
            1730                1735                1740

Ala Ala Thr Thr Thr Cys Gly Ala Thr Cys Ala Ala Cys Ala Ala
            1745                1750                1755

Ala Cys Ala Thr Cys Thr Cys Ala Ala Ala Ala Thr Ala Thr Cys
            1760                1765                1770

Ala Ala Gly Ala Ala Thr Cys Ala Gly Thr Thr Ala Gly Cys Gly
            1775                1780                1785

Gly Ala Ala Thr Thr Ala Ala Ala Cys Gly Cys Ala Ala Cys Thr
            1790                1795                1800

Ala Ala Cys Ala Thr Ala Thr Ala Thr Ala Cys Thr Gly Thr Ala
            1805                1810                1815
```

-continued

Thr Thr Ala Gly Ala Thr Ala Ala Ala Thr Cys Ala Ala Ala
    1820            1825            1830

Thr Thr Ala Ala Ala Thr Gly Cys Ala Ala Ala Ala Thr Gly
    1835            1840            1845

Ala Ala Thr Ala Thr Thr Thr Thr Ala Ala Thr Ala Ala Gly Ala
    1850            1855            1860

Gly Ala Thr Ala Ala Ala Cys Gly Thr Thr Thr Cys Ala Thr
    1865            1870            1875

Thr Ala Thr Gly Ala Thr Ala Gly Ala Ala Thr Ala Ala Cys
    1880            1885            1890

Ala Thr Ala Gly Cys Ala Gly Thr Thr Gly Gly Gly Cys Gly
    1895            1900            1905

Gly Ala Thr Gly Ala Gly Thr Cys Ala Gly Thr Ala Gly Thr Thr
    1910            1915            1920

Ala Ala Gly Gly Ala Gly Gly Cys Thr Cys Ala Thr Ala Gly Ala
    1925            1930            1935

Gly Ala Ala Gly Thr Ala Ala Thr Thr Ala Ala Thr Thr Cys Gly
    1940            1945            1950

Thr Cys Ala Ala Cys Ala Gly Ala Gly Gly Gly Ala Thr Thr Ala
    1955            1960            1965

Thr Thr Gly Thr Thr Ala Ala Ala Thr Ala Thr Thr Gly Ala Thr
    1970            1975            1980

Ala Ala Gly Gly Ala Thr Ala Thr Ala Ala Gly Ala Ala Ala Ala
    1985            1990            1995

Ala Thr Ala Thr Thr Ala Thr Cys Ala Gly Gly Thr Thr Ala Thr
    2000            2005            2010

Ala Thr Thr Gly Thr Ala Gly Ala Ala Ala Thr Thr Gly Ala Ala
    2015            2020            2025

Gly Ala Thr Ala Cys Thr Gly Ala Ala Gly Gly Gly Cys Thr Thr
    2030            2035            2040

Ala Ala Ala Gly Ala Ala Gly Thr Thr Ala Thr Ala Ala Ala Thr
    2045            2050            2055

Gly Ala Cys Ala Gly Ala Thr Ala Thr Gly Ala Thr Ala Thr Gly
    2060            2065            2070

Thr Thr Gly Ala Ala Thr Ala Thr Thr Thr Cys Thr Ala Gly Thr
    2075            2080            2085

Thr Thr Ala Cys Gly Gly Cys Ala Ala Gly Ala Thr Gly Gly Ala
    2090            2095            2100

Ala Ala Ala Ala Cys Ala Thr Thr Thr Ala Thr Ala Gly Ala Thr
    2105            2110            2115

Thr Thr Thr Ala Ala Ala Ala Ala Ala Thr Ala Thr Ala Ala Thr
    2120            2125            2130

Gly Ala Thr Ala Ala Ala Thr Ala Cys Cys Gly Thr Thr Ala
    2135            2140            2145

Thr Ala Thr Ala Thr Ala Ala Gly Thr Ala Ala Thr Cys Cys Cys
    2150            2155            2160

Ala Ala Thr Thr Ala Thr Ala Ala Gly Gly Thr Ala Ala Ala Thr
    2165            2170            2175

Gly Thr Ala Thr Ala Thr Gly Cys Thr Gly Thr Thr Ala Cys Thr
    2180            2185            2190

Ala Ala Ala Gly Ala Ala Ala Ala Cys Ala Cys Thr Ala Thr Thr
    2195            2200            2205

```
Ala Thr Thr Ala Ala Thr Cys Cys Thr Ala Gly Thr Gly Ala Gly
    2210                2215                2220

Ala Ala Thr Gly Gly Gly Gly Ala Thr Ala Cys Thr Ala Gly Thr
    2225                2230                2235

Ala Cys Cys Ala Ala Cys Gly Gly Ala Thr Cys Ala Ala Gly
    2240                2245                2250

Ala Ala Ala Ala Thr Thr Thr Thr Ala Ala Thr Cys Thr Thr Thr
    2255                2260                2265

Thr Cys Thr Ala Ala Ala Ala Ala Gly Gly Cys Thr Ala Thr
    2270                2275                2280

Gly Ala Gly Ala Thr Ala Gly Gly Ala Thr Ala Ala
    2285                2290                2295

<210> SEQ ID NO 92
<211> LENGTH: 762
<212> TYPE: PRT
<213> ORGANISM: Streptococcus pyogenes

<400> SEQUENCE: 92

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Ser Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285
```

```
Pro Ile Val His Val Asp Met Glu Asn Ile Ile Leu Ser Lys Asn Glu
    290                 295                 300
Asp Gln Ser Thr Gln Asn Thr Asp Ser Gln Thr Arg Thr Ile Ser Lys
305                 310                 315                 320
Asn Thr Ser Thr Ser Arg Thr His Thr Ser Glu Val His Gly Asn Ala
                325                 330                 335
Glu Val His Ala Ser Phe Phe Asp Ile Gly Gly Ser Val Ser Ala Gly
            340                 345                 350
Phe Ser Asn Ser Asn Ser Ser Thr Val Ala Ile Asp His Ser Leu Ser
        355                 360                 365
Leu Ala Gly Glu Arg Thr Trp Ala Glu Thr Met Gln Thr Ala Asp Thr
370                 375                 380
Ala Arg Leu Asn Ala Asn Ile Arg Tyr Val Asn Thr Gly Thr Ala Pro
385                 390                 395                 400
Ile Tyr Asn Val Leu Pro Thr Thr Ser Leu Val Leu Gly Lys Asn Gln
                405                 410                 415
Thr Leu Ala Thr Ile Lys Ala Lys Glu Asn Gln Leu Ser Gln Ile Leu
            420                 425                 430
Ala Pro Asn Asn Tyr Tyr Pro Ser Lys Asn Leu Ala Pro Ile Ala Leu
        435                 440                 445
Asn Ala Gln Asp Asp Phe Ser Ser Thr Pro Ile Thr Met Asn Tyr Asn
450                 455                 460
Gln Phe Leu Glu Leu Glu Lys Thr Lys Gln Leu Arg Leu Asp Thr Asp
465                 470                 475                 480
Gln Val Tyr Gly Asn Ile Ala Thr Tyr Asn Phe Glu Asn Gly Arg Val
                485                 490                 495
Arg Val Asp Thr Gly Ser Asn Trp Ser Glu Val Leu Pro Gln Ile Gln
            500                 505                 510
Glu Thr Thr Ala Arg Ile Ile Phe Asn Gly Lys Asp Leu Asn Leu Val
        515                 520                 525
Glu Arg Arg Ile Ala Ala Val Asn Pro Ser Asp Pro Leu Glu Thr Thr
530                 535                 540
Lys Pro Asp Met Thr Leu Lys Glu Ala Leu Lys Ile Ala Phe Gly Phe
545                 550                 555                 560
Asn Glu Pro Asn Gly Asn Leu Gln Tyr Gln Gly Lys Asp Ile Thr Glu
                565                 570                 575
Phe Asp Phe Asn Phe Asp Gln Gln Thr Ser Gln Asn Ile Lys Asn Gln
            580                 585                 590
Leu Ala Glu Leu Asn Ala Thr Asn Ile Tyr Thr Val Leu Asp Lys Ile
        595                 600                 605
Lys Leu Asn Ala Lys Met Asn Ile Leu Ile Arg Asp Lys Arg Phe His
610                 615                 620
Tyr Asp Arg Asn Asn Ile Ala Val Gly Ala Asp Glu Ser Val Val Lys
625                 630                 635                 640
Glu Ala His Arg Glu Val Ile Asn Ser Ser Thr Glu Gly Leu Leu Leu
                645                 650                 655
Asn Ile Asp Lys Asp Ile Arg Ser Ile Leu Ser Gly Tyr Ile Val Glu
            660                 665                 670
Ile Glu Asp Thr Glu Gly Leu Lys Glu Val Ile Asn Asp Arg Tyr Asp
        675                 680                 685
Met Leu Asn Ile Ser Ser Leu Arg Gln Asp Gly Lys Thr Phe Ile Asp
690                 695                 700
```

```
Phe Lys Lys Tyr Asn Asp Lys Leu Pro Leu Tyr Ile Ser Asn Pro Asn
705                 710                 715                 720

Tyr Lys Val Asn Val Tyr Ala Val Thr Lys Glu Asn Thr Ile Ile Asn
            725                 730                 735

Pro Ser Glu Asn Gly Asp Thr Ser Thr Asn Gly Ile Lys Lys Ile Leu
        740                 745                 750

Ile Phe Ser Lys Lys Gly Tyr Glu Ile Gly
        755                 760

<210> SEQ ID NO 93
<211> LENGTH: 375
<212> TYPE: PRT
<213> ORGANISM: Streptococcus pyogenes

<400> SEQUENCE: 93

Ala Thr Gly Ala Ala Thr Ala Ala Gly Thr Ala Ala Ala Thr
1               5                   10                  15

Thr Thr Thr Ala Thr Gly Thr Thr Thr Ala Thr Thr Thr Ala Cys
            20                  25                  30

Gly Gly Cys Gly Thr Thr Ala Cys Thr Ala Thr Cys Cys Thr Cys Thr
            35                  40                  45

Cys Thr Ala Thr Gly Thr Gly Cys Ala Cys Ala Cys Gly Gly Ala Gly
            50                  55                  60

Cys Thr Cys Cys Thr Cys Ala Gly Thr Cys Thr Ala Thr Thr Ala Cys
65                  70                  75                  80

Ala Gly Ala Ala Cys Thr Ala Thr Gly Thr Thr Cys Gly Gly Ala Ala
                85                  90                  95

Thr Ala Thr Cys Ala Cys Ala Cys Ala Cys Ala Cys Ala Ala Ala
                100                 105                 110

Thr Ala Thr Ala Thr Ala Cys Gly Ala Thr Ala Ala Thr Gly Ala
                115                 120                 125

Cys Ala Ala Gly Ala Thr Ala Cys Thr Ala Thr Cys Ala Thr Ala Thr
                130                 135                 140

Ala Cys Gly Gly Ala Ala Thr Cys Gly Ala Thr Gly Gly Cys Ala Gly
145                 150                 155                 160

Gly Cys Ala Ala Ala Ala Gly Ala Gly Ala Ala Thr Gly Gly Thr
                165                 170                 175

Thr Ala Thr Cys Ala Thr Thr Ala Cys Ala Thr Thr Ala Ala Gly
                180                 185                 190

Ala Gly Cys Gly Gly Cys Gly Cys Ala Ala Cys Ala Thr Thr Cys
                195                 200                 205

Ala Gly Gly Thr Cys Gly Ala Ala Gly Thr Cys Cys Cys Gly Gly Gly
                210                 215                 220

Cys Ala Gly Thr Cys Ala Ala Cys Ala Thr Ala Thr Gly Ala Cys
225                 230                 235                 240

Thr Cys Cys Cys Ala Ala Ala Ala Ala Ala Gly Cys Cys Ala
                245                 250                 255

Thr Thr Gly Ala Ala Gly Gly Ala Thr Gly Ala Gly Gly Ala
                260                 265                 270

Cys Ala Cys Ala Thr Thr Ala Gly Ala Ala Thr Cys Ala Cys Ala
                275                 280                 285

Thr Ala Thr Cys Thr Gly Ala Cys Cys Gly Ala Gly Ala Cys Cys Ala
                290                 295                 300

Ala Ala Ala Thr Thr Gly Ala Thr Ala Ala Ala Thr Thr Ala Thr Gly
305                 310                 315                 320
```

Thr Gly Thr Ala Thr Gly Gly Ala Ala Thr Ala Ala Ala
            325                 330                 335

Ala Cys Cys Cys Cys Ala Ala Thr Thr Cys Ala Ala Thr Thr Gly
            340                 345                 350

Cys Gly Gly Cys Ala Ala Thr Cys Ala Gly Cys Ala Thr Gly Gly Ala
            355                 360                 365

Ala Ala Ala Cys Thr Ala Gly
            370                 375

<210> SEQ ID NO 94
<211> LENGTH: 124
<212> TYPE: PRT
<213> ORGANISM: Streptococcus pyogenes

<400> SEQUENCE: 94

Met Asn Lys Val Lys Phe Tyr Val Leu Phe Thr Ala Leu Leu Ser Ser
1               5                   10                  15

Leu Cys Ala His Gly Ala Pro Gln Ser Ile Thr Glu Leu Cys Ser Glu
            20                  25                  30

Tyr His Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
    50                  55                  60

Ser Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn
        115                 120

<210> SEQ ID NO 95
<211> LENGTH: 868
<212> TYPE: PRT
<213> ORGANISM: Streptococcus pyogenes

<400> SEQUENCE: 95

Ala Thr Gly Ala Thr Thr Gly Ala Cys Ala Thr Cys Ala Thr Gly Thr
1               5                   10                  15

Thr Gly Cys Ala Thr Ala Thr Ala Gly Gly Thr Thr Ala Gly Ala Thr
            20                  25                  30

Ala Ala Ala Cys Ala Ala Gly Thr Gly Gly Thr Thr Ala Thr Cys
        35                  40                  45

Thr Thr Thr Cys Cys Gly Gly Ala Thr Thr Gly Thr Cys Thr Thr Cys
    50                  55                  60

Thr Thr Gly Thr Ala Thr Gly Ala Thr Ala Thr Ala Thr Ala Ala Gly
65                  70                  75                  80

Thr Thr Thr Thr Cys Cys Thr Cys Gly Ala Thr Gly Ala Ala Ala Ala
                85                  90                  95

Ala Thr Ala Thr Ala Ala Cys Thr Thr Thr Cys Ala Thr Thr Thr Thr
            100                 105                 110

Thr Thr Thr Thr Ala Thr Thr Thr Ala Thr Ala Gly Cys Ala
        115                 120                 125

Thr Cys Gly Cys Cys Ala Thr Ala Thr Ala Thr Gly Cys Ala Ala
        130                 135                 140

```
Ala Thr Gly Gly Cys Gly Ala Cys Ala Gly Ala Thr Ala Thr Ala
145                 150                 155                 160

Cys Cys Gly Thr Gly Cys Thr Gly Ala Cys Thr Cys Ala Gly Ala
                165                 170                 175

Cys Cys Cys Cys Cys Ala Gly Ala Thr Gly Ala Ala Thr Ala Ala
                180                 185                 190

Ala Ala Cys Gly Thr Thr Thr Cys Cys Gly Ala Gly Thr Cys Thr
            195                 200                 205

Thr Ala Thr Gly Cys Cys Cys Ala Gly Ala Gly Gly Thr Ala Ala Thr
        210                 215                 220

Gly Ala Gly Thr Ala Cys Thr Thr Cys Gly Ala Thr Ala Gly Ala Gly
225                 230                 235                 240

Gly Ala Ala Cys Thr Cys Ala Ala Ala Thr Gly Ala Ala Thr Ala Thr
                245                 250                 255

Thr Ala Ala Thr Cys Thr Thr Thr Ala Thr Gly Ala Thr Cys Ala Cys
            260                 265                 270

Gly Cys Gly Ala Gly Ala Gly Gly Ala Ala Cys Ala Cys Ala Ala Ala
        275                 280                 285

Cys Cys Gly Gly Cys Thr Thr Gly Thr Cys Ala Gly Ala Thr Ala
290                 295                 300

Thr Gly Ala Thr Gly Ala Cys Gly Gly Ala Thr Ala Thr Gly Thr Thr
305                 310                 315                 320

Thr Cys Cys Ala Cys Thr Thr Cys Thr Cys Thr Thr Ala Gly Thr Thr
                325                 330                 335

Thr Gly Ala Gly Ala Ala Gly Thr Gly Thr Cys Thr Cys Ala Cys Thr Thr
            340                 345                 350

Ala Gly Cys Ala Gly Gly Ala Cys Ala Gly Thr Ala Thr Ala Thr Ala
        355                 360                 365

Thr Thr Ala Thr Cys Ala Gly Gly Ala Thr Ala Thr Thr Cys Ala Cys
        370                 375                 380

Thr Thr Ala Cys Thr Ala Thr Ala Thr Ala Thr Cys Gly Thr
385                 390                 395                 400

Thr Ala Thr Ala Gly Cys Ala Ala Ala Thr Ala Thr Gly Thr Thr Thr
            405                 410                 415

Ala Ala Thr Gly Thr Thr Ala Ala Thr Gly Ala Thr Gly Thr Ala Ala
            420                 425                 430

Thr Thr Ala Gly Cys Gly Thr Ala Thr Ala Cys Ala Gly Cys Cys Cys
        435                 440                 445

Thr Cys Ala Cys Cys Cys Ala Thr Ala Thr Gly Ala Ala Cys Ala Gly
        450                 455                 460

Gly Ala Gly Gly Thr Thr Thr Cys Thr Gly Cys Gly Thr Thr Ala Gly
465                 470                 475                 480

Gly Thr Gly Gly Ala Ala Thr Ala Cys Cys Ala Thr Ala Thr Cys
            485                 490                 495

Thr Cys Ala Gly Ala Thr Ala Thr Ala Gly Gly Ala Thr Gly Gly
        500                 505                 510

Thr Ala Thr Cys Gly Thr Gly Thr Thr Ala Ala Thr Thr Thr Gly
        515                 520                 525

Gly Thr Gly Thr Gly Ala Thr Thr Gly Ala Thr Gly Ala Ala Cys Gly
        530                 535                 540

Ala Thr Thr Ala Cys Ala Thr Cys Gly Thr Ala Ala Cys Ala Gly Gly
545                 550                 555                 560
```

Gly Ala Ala Thr Ala Thr Ala Gly Ala Gly Ala Cys Cys Gly Gly Thr
                565                 570                 575

Ala Thr Thr Ala Cys Ala Gly Ala Ala Thr Cys Thr Gly Ala Ala
                580                 585                 590

Thr Ala Thr Ala Gly Cys Thr Cys Gly Gly Cys Ala Gly Ala Gly
                595                 600                 605

Gly Ala Thr Gly Gly Thr Thr Ala Cys Ala Gly Ala Thr Ala Gly
            610                 615                 620

Cys Ala Gly Gly Thr Thr Cys Cys Ala Cys Cys Gly Gly Ala
625                 630                 635                 640

Thr Cys Ala Cys Ala Ala Gly Cys Thr Gly Gly Ala Gly Ala
                645                 650                 655

Gly Ala Ala Gly Ala Ala Cys Cys Thr Gly Gly Ala Thr Thr Cys
                660                 665                 670

Ala Thr Cys Ala Thr Gly Cys Ala Cys Ala Cys Ala Ala Gly Gly
                675                 680                 685

Thr Thr Gly Thr Gly Gly Ala Gly Ala Thr Thr Cys Ala Thr Cys Ala
                690                 695                 700

Ala Gly Ala Ala Cys Ala Ala Thr Cys Ala Cys Ala Gly Gly Thr Gly
705                 710                 715                 720

Ala Thr Ala Cys Thr Thr Gly Thr Ala Ala Thr Gly Ala Gly Gly Ala
                725                 730                 735

Gly Ala Cys Cys Cys Ala Gly Ala Thr Cys Thr Gly Ala Gly Cys
                740                 745                 750

Ala Cys Ala Ala Thr Ala Thr Ala Thr Cys Thr Cys Ala Gly Gly Gly
                755                 760                 765

Ala Ala Thr Ala Thr Cys Ala Ala Thr Cys Ala Ala Ala Gly Thr
                770                 775                 780

Thr Ala Ala Gly Ala Gly Gly Cys Ala Gly Ala Thr Ala Thr Thr Thr
785                 790                 795                 800

Thr Cys Ala Gly Ala Cys Thr Ala Thr Cys Ala Gly Thr Cys Ala Gly
                805                 810                 815

Ala Gly Gly Thr Thr Gly Ala Cys Ala Thr Ala Thr Ala Ala
                820                 825                 830

Cys Ala Gly Ala Ala Thr Thr Cys Gly Gly Gly Ala Thr Gly Ala Ala
                835                 840                 845

Thr Thr Ala Thr Gly Ala Ala Thr Ala Ala Gly Thr Ala Ala Ala
                850                 855                 860

Ala Thr Gly Thr
865

<210> SEQ ID NO 96
<211> LENGTH: 252
<212> TYPE: PRT
<213> ORGANISM: Streptococcus pyogenes

<400> SEQUENCE: 96

Met Lys Asn Ile Thr Phe Ile Phe Phe Ile Leu Leu Asp Leu Tyr Ala
1               5                   10                  15

Asn Gly Asp Arg Leu Tyr Arg Ala Asp Ser Arg Pro Pro Asp Glu Ile
            20                  25                  30

Lys Arg Phe Arg Ser Leu Met Pro Arg Gly Asn Glu Tyr Phe Asp Arg
        35                  40                  45

Gly Thr Gln Met Asn Ile Asn Leu Tyr Asp His Ala Arg Gly Thr Gln
    50                  55                  60

Thr Gly Phe Val Arg Tyr Asp Asp Gly Tyr Val Ser Thr Ser Leu Ser
65                  70                  75                  80

Leu Arg Ser Ala His Leu Ala Gly Gln Tyr Ile Leu Ser Gly Tyr Ser
                85                  90                  95

Leu Thr Ile Tyr Ile Val Ile Ala Asn Met Phe Asn Val Asn Asp Val
            100                 105                 110

Ile Ser Val Tyr Ser Pro His Pro Tyr Glu Gln Glu Val Ser Ala Leu
        115                 120                 125

Gly Gly Ile Pro Tyr Ser Gln Ile Tyr Gly Trp Tyr Arg Val Asn Phe
    130                 135                 140

Gly Val Ile Asp Glu Arg Leu His Arg Asn Arg Glu Tyr Arg Asp Arg
145                 150                 155                 160

Tyr Tyr Arg Asn Leu Asn Ile Ala Pro Ala Glu Asp Gly Tyr Arg Leu
                165                 170                 175

Ala Gly Phe Pro Pro Asp His Gln Ala Trp Arg Glu Glu Pro Trp Ile
            180                 185                 190

His His Ala Pro Gln Gly Cys Gly Asp Ser Ser Arg Thr Ile Thr Gly
        195                 200                 205

Asp Thr Cys Asn Glu Glu Thr Gln Asn Leu Ser Thr Ile Tyr Leu Arg
210                 215                 220

Glu Tyr Gln Ser Lys Val Lys Arg Gln Ile Phe Ser Asp Tyr Gln Ser
225                 230                 235                 240

Glu Val Asp Ile Tyr Asn Arg Ile Arg Asp Glu Leu
                245                 250

<210> SEQ ID NO 97
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(4)
<223> OTHER INFORMATION: Where X is any aminio acid
<220> FEATURE:
<221> NAME/KEY: MISC_FEATURE
<222> LOCATION: (6)..(6)
<223> OTHER INFORMATION: Where X is any aminio acid

<400> SEQUENCE: 97

Trp Xaa Xaa Xaa Val Xaa Val Tyr Pro Lys
1               5                   10

<210> SEQ ID NO 98
<211> LENGTH: 1749
<212> TYPE: PRT
<213> ORGANISM: Streptococcus pyogenes

<400> SEQUENCE: 98

Ala Cys Thr Thr Thr Ala Gly Thr Thr Ala Gly Ala Ala Gly Gly
1               5                   10                  15

Ala Gly Gly Gly Ala Gly Ala Gly Gly Ala Thr Ala Thr Ala Thr
                20                  25                  30

Gly Cys Ala Ala Ala Gly Ala Gly Gly Ala Thr Ala Ala Ala
            35                  40                  45

Ala Cys Cys Ala Ala Thr Thr Ala Thr Gly Gly Ala Ala Gly Cys Gly
50                  55                  60

Cys Thr Ala Ala Cys Ala Ala Cys Ala Ala Ala Cys Gly Ala Cys Gly

-continued 65 70 75 80

Ala Cys Ala Ala Ala Cys Gly Ala Cys Gly Ala Thr Cys Gly Gly Ala
85 90 95

Thr Thr Ala Cys Thr Gly Ala Ala Ala Gly Thr Ala Thr Thr Thr Thr
100 105 110

Thr Gly Ala Cys Gly Thr Thr Thr Gly Thr Ala Gly Cys Thr Cys Thr
115 120 125

Gly Ala Thr Ala Gly Gly Ala Ala Thr Ala Gly Thr Ala Gly Gly Gly
130 135 140

Thr Thr Thr Thr Cys Thr Ala Thr Cys Ala Gly Ala Gly Cys Gly Thr
145 150 155 160

Thr Cys Gly Gly Ala Gly Cys Thr Gly Ala Ala Gly Ala Ala Cys Ala
165 170 175

Ala Thr Cys Ala Gly Thr Gly Cys Cys Ala Ala Ala Thr Ala Ala Ala
180 185 190

Cys Ala Ala Ala Gly Cys Gly Gly Thr Ala Ala Ala Cys Thr Gly Gly
195 200 205

Thr Ala Ala Thr Cys Thr Gly Gly Ala Thr Thr Ala Ala Cys Gly Gly
210 215 220

Cys Gly Ala Thr Ala Ala Ala Gly Gly Cys Thr Ala Thr Ala Ala Cys
225 230 235 240

Gly Gly Thr Cys Thr Cys Gly Cys Thr Gly Ala Ala Gly Thr Cys Gly
245 250 255

Gly Thr Ala Ala Gly Ala Ala Ala Thr Thr Cys Gly Ala Gly Ala Ala
260 265 270

Ala Gly Ala Thr Ala Cys Cys Gly Gly Ala Ala Thr Thr Ala Ala Ala
275 280 285

Gly Thr Cys Ala Cys Cys Gly Thr Thr Gly Ala Gly Cys Ala Thr Cys
290 295 300

Cys Gly Gly Ala Thr Ala Ala Ala Cys Thr Gly Gly Ala Ala Gly Ala
305 310 315 320

Gly Ala Ala Ala Thr Thr Cys Cys Cys Ala Cys Ala Gly Gly Thr Thr
325 330 335

Gly Cys Gly Gly Cys Ala Ala Cys Thr Gly Gly Cys Gly Ala Thr Gly
340 345 350

Gly Cys Cys Cys Thr Gly Ala Cys Ala Thr Thr Ala Thr Cys Thr Thr
355 360 365

Cys Thr Gly Gly Gly Cys Ala Cys Ala Cys Gly Ala Cys Cys Gly Cys
370 375 380

Thr Thr Thr Gly Gly Thr Gly Gly Cys Thr Ala Cys Gly Cys Thr Cys
385 390 395 400

Ala Ala Thr Cys Thr Gly Gly Cys Cys Thr Gly Thr Thr Gly Gly Cys
405 410 415

Thr Gly Ala Ala Ala Thr Cys Ala Cys Cys Cys Cys Gly Gly Ala Cys
420 425 430

Ala Ala Ala Gly Cys Gly Thr Thr Cys Cys Ala Gly Gly Ala Cys Ala
435 440 445

Ala Gly Cys Thr Gly Thr Ala Thr Cys Cys Gly Thr Thr Thr Ala Cys
450 455 460

Cys Thr Gly Gly Gly Ala Thr Gly Cys Cys Gly Thr Ala Cys Gly Thr
465 470 475 480

Thr Ala Cys Ala Ala Cys Gly Gly Cys Ala Ala Gly Cys Thr Gly Ala
485 490 495

```
Thr Thr Gly Cys Thr Thr Ala Cys Cys Cys Gly Ala Thr Cys Gly Cys
            500                 505                 510
Thr Gly Thr Thr Gly Ala Ala Gly Cys Gly Thr Thr Ala Thr Cys Gly
        515                 520                 525

Cys Thr Gly Ala Thr Thr Thr Ala Thr Ala Ala Cys Ala Ala Ala Gly
    530                 535                 540

Ala Thr Cys Thr Gly Cys Thr Gly Cys Cys Gly Ala Ala Cys Cys Cys
545                 550                 555                 560

Gly Cys Cys Ala Ala Ala Ala Ala Cys Cys Thr Gly Gly Gly Ala Ala
                565                 570                 575

Gly Ala Gly Ala Thr Cys Cys Cys Gly Gly Cys Gly Cys Thr Gly Gly
            580                 585                 590
Ala Thr Ala Ala Ala Gly Ala Ala Cys Thr Gly Ala Ala Ala Gly Cys
        595                 600                 605

Gly Ala Ala Ala Gly Gly Thr Ala Ala Gly Ala Gly Cys Gly Cys Gly
    610                 615                 620

Cys Thr Gly Ala Thr Gly Thr Thr Cys Ala Ala Cys Cys Thr Gly Cys
625                 630                 635                 640
Ala Ala Gly Ala Ala Cys Cys Gly Thr Ala Cys Thr Thr Cys Ala Cys
                645                 650                 655
Cys Thr Gly Gly Cys Cys Gly Cys Thr Gly Ala Thr Thr Gly Cys Thr
            660                 665                 670

Gly Cys Thr Gly Ala Cys Gly Gly Gly Gly Gly Thr Thr Ala Thr Gly
        675                 680                 685
Cys Gly Thr Thr Cys Ala Ala Gly Thr Ala Thr Gly Ala Ala Ala Ala
    690                 695                 700

Cys Gly Gly Cys Ala Ala Gly Thr Ala Cys Gly Ala Cys Ala Thr Thr
705                 710                 715                 720

Ala Ala Ala Gly Ala Cys Gly Thr Gly Gly Gly Cys Gly Thr Gly Gly
                725                 730                 735

Ala Thr Ala Ala Cys Gly Cys Thr Gly Gly Cys Gly Cys Gly Ala Ala
            740                 745                 750
Ala Gly Cys Gly Gly Gly Thr Cys Thr Gly Ala Cys Cys Thr Thr Cys
        755                 760                 765

Cys Thr Gly Gly Thr Thr Gly Ala Cys Cys Thr Gly Ala Thr Thr Ala
    770                 775                 780

Ala Ala Ala Ala Cys Ala Ala Ala Cys Ala Cys Ala Thr Gly Ala Ala
785                 790                 795                 800

Thr Gly Cys Ala Gly Ala Cys Ala Cys Cys Gly Ala Thr Thr Ala Cys
                805                 810                 815

Thr Cys Cys Ala Thr Cys Gly Cys Ala Gly Ala Ala Gly Cys Thr Gly
            820                 825                 830

Cys Cys Thr Thr Thr Ala Ala Thr Ala Ala Ala Gly Gly Cys Gly Ala
        835                 840                 845

Ala Ala Cys Ala Gly Cys Gly Ala Thr Gly Ala Cys Cys Ala Thr Cys
    850                 855                 860

Ala Ala Cys Gly Gly Cys Cys Cys Gly Thr Gly Gly Gly Cys Ala Thr
865                 870                 875                 880

Gly Gly Thr Cys Cys Ala Ala Cys Ala Thr Cys Gly Ala Cys Ala Cys
                885                 890                 895

Cys Ala Gly Cys Ala Ala Ala Gly Thr Gly Ala Ala Thr Thr Ala Thr
            900                 905                 910
```

```
Gly Gly Thr Gly Thr Ala Ala Cys Gly Gly Thr Ala Thr Gly Cys
            915                 920                 925

Cys Gly Ala Cys Cys Thr Thr Cys Ala Ala Gly Gly Thr Cys Ala
930                 935                 940

Ala Cys Cys Ala Thr Cys Cys Ala Ala Cys Cys Gly Thr Thr Cys
945                 950                 955                 960

Gly Thr Thr Gly Gly Cys Gly Thr Gly Cys Thr Gly Ala Cys Gly
                965                 970                 975

Cys Ala Gly Gly Thr Ala Thr Thr Ala Ala Cys Gly Cys Gly Cys
            980                 985                 990

Cys Ala Gly Thr Cys Cys Gly Ala Ala Cys Ala Ala Ala Gly Ala Gly
            995                 1000                1005

Cys Thr Gly Gly Cys Ala Ala Ala Ala Gly Ala Gly Thr Thr Cys
    1010                1015                    1020

Cys Thr Cys Gly Ala Ala Ala Cys Thr Ala Thr Cys Thr Gly
    1025                1030                    1035

Cys Thr Gly Ala Cys Thr Gly Ala Thr Gly Ala Ala Gly Gly Thr
    1040                1045                    1050

Cys Thr Gly Gly Ala Ala Gly Cys Gly Gly Thr Thr Ala Ala Thr
    1055                1060                    1065

Ala Ala Ala Gly Ala Cys Ala Ala Cys Cys Gly Cys Thr Gly
    1070                1075                    1080

Gly Gly Thr Gly Cys Cys Gly Thr Ala Gly Cys Gly Cys Thr Gly
    1085                1090                    1095

Ala Ala Gly Thr Cys Thr Thr Ala Cys Gly Ala Gly Gly Ala Ala
    1100                1105                    1110

Gly Ala Gly Thr Thr Gly Gly Thr Gly Ala Ala Ala Gly Ala Thr
    1115                1120                    1125

Cys Cys Gly Cys Gly Gly Ala Thr Thr Gly Cys Cys Gly Cys Cys
    1130                1135                    1140

Ala Cys Thr Ala Thr Gly Gly Ala Ala Ala Ala Cys Gly Cys Cys
    1145                1150                    1155

Cys Ala Gly Ala Ala Ala Gly Gly Thr Gly Ala Ala Ala Thr Cys
    1160                1165                    1170

Ala Thr Gly Cys Cys Gly Ala Ala Cys Ala Thr Cys Cys Cys Gly
    1175                1180                    1185

Cys Ala Gly Ala Thr Gly Thr Cys Cys Gly Cys Thr Thr Thr Cys
    1190                1195                    1200

Thr Gly Gly Thr Ala Thr Gly Cys Cys Gly Thr Gly Cys Gly Thr
    1205                1210                    1215

Ala Cys Thr Gly Cys Gly Gly Thr Gly Ala Thr Cys Ala Ala Cys
    1220                1225                    1230

Gly Cys Cys Gly Cys Cys Ala Gly Cys Gly Gly Thr Cys Gly Thr
    1235                1240                    1245

Cys Ala Gly Ala Cys Thr Gly Thr Cys Gly Ala Thr Gly Ala Ala
    1250                1255                    1260

Gly Cys Cys Cys Thr Gly Ala Ala Gly Ala Cys Gly Cys Gly
    1265                1270                    1275

Cys Ala Gly Ala Cys Thr Ala Ala Thr Thr Cys Gly Ala Gly Cys
    1280                1285                    1290

Ala Ala Gly Thr Thr Ala Ala Cys Thr Ala Thr Thr Cys Thr
    1295                1300                    1305

Ala Ala Ala Ala Cys Thr Gly Thr Thr Ala Cys Thr Gly Gly Ala
```

-continued

```
            1310                1315                1320

Ala Cys Thr Ala Thr Thr Gly Cys Ala Gly Ala Thr Ala Ala Gly
    1325                1330                1335

Ala Ala Ala Ala Ala Ala Gly Ala Ala Thr Thr Ala Ala Cys
    1340                1345                1350

Thr Thr Thr Gly Ala Ala Ala Thr Ala Cys Ala Thr Thr Thr Ala
    1355                1360                1365

Ala Ala Ala Thr Cys Thr Thr Cys Thr Gly Ala Thr Gly Gly Ala
    1370                1375                1380

Cys Ala Ala Gly Cys Thr Ala Thr Ala Ala Gly Thr Gly Gly Ala
    1385                1390                1395

Ala Cys Ala Thr Ala Thr Cys Cys Gly Ala Cys Ala Ala Ala Cys
    1400                1405                1410

Thr Cys Thr Gly Gly Ala Gly Ala Ala Cys Thr Cys Ala Cys Ala
    1415                1420                1425

Gly Thr Thr Ala Cys Ala Gly Ala Thr Gly Gly Ala Ala Ala Ala
    1430                1435                1440

Gly Cys Thr Ala Cys Cys Thr Thr Cys Ala Cys Ala Thr Thr Ala
    1445                1450                1455

Ala Ala Gly Gly Ala Thr Gly Gly Ala Gly Ala Ala Thr Cys Ala
    1460                1465                1470

Thr Thr Gly Ala Thr Thr Gly Thr Thr Gly Ala Gly Gly Gly Gly
    1475                1480                1485

Cys Thr Ala Cys Cys Thr Thr Cys Ala Gly Gly Thr Thr Ala Cys
    1490                1495                1500

Thr Cys Thr Thr Ala Thr Gly Ala Ala Ala Thr Thr Ala Cys Ala
    1505                1510                1515

Gly Ala Ala Ala Cys Gly Gly Gly Thr Gly Cys Thr Thr Cys Ala
    1520                1525                1530

Gly Ala Thr Thr Ala Thr Gly Ala Gly Gly Thr Ala Ala Gly Thr
    1535                1540                1545

Gly Thr Thr Ala Ala Thr Gly Ala Ala Ala Ala Ala Ala Ala Thr
    1550                1555                1560

Gly Cys Ala Cys Cys Ala Gly Ala Thr Gly Gly Ala Ala Ala Ala
    1565                1570                1575

Gly Cys Gly Ala Cys Gly Ala Ala Ala Gly Cys Cys Thr Cys Ala
    1580                1585                1590

Gly Thr Thr Ala Ala Gly Gly Ala Ala Gly Ala Thr Gly Ala Gly
    1595                1600                1605

Ala Cys Thr Gly Thr Ala Gly Cys Thr Thr Thr Gly Ala Ala
    1610                1615                1620

Ala Ala Cys Cys Gly Ala Ala Ala Ala Gly Ala Thr Cys Thr Thr
    1625                1630                1635

Gly Thr Cys Cys Cys Ala Cys Cys Ala Ala Cys Thr Gly Gly Thr
    1640                1645                1650

Thr Thr Gly Ala Cys Ala Ala Cys Ala Gly Ala Thr Gly Gly Gly
    1655                1660                1665

Gly Cys Thr Ala Thr Cys Thr Ala Thr Cys Thr Thr Thr Gly Gly
    1670                1675                1680

Thr Thr Gly Thr Thr Ala Thr Thr Ala Cys Thr Thr Gly Thr Thr
    1685                1690                1695

Cys Cys Ala Thr Thr Thr Gly Gly Gly Thr Thr Ala Thr Thr Gly
    1700                1705                1710
```

Gly Thr Thr Thr Gly Gly Cys Thr Ala Thr Thr Gly Gly Thr
    1715                1720               1725

Cys Gly Thr Ala Ala Gly Gly Gly Ala Cys Thr Ala Ala Ala
    1730            1735               1740

Ala Ala Ala Thr Gly Ala
    1745

<210> SEQ ID NO 99
<211> LENGTH: 568
<212> TYPE: PRT
<213> ORGANISM: Streptococcus pyogenes

<400> SEQUENCE: 99

Leu Gln Lys Arg Asp Lys Thr Asn Tyr Gly Ser Ala Asn Asn Lys Arg
1               5                   10                  15

Arg Gln Thr Thr Ile Gly Leu Leu Lys Val Phe Leu Thr Phe Val Leu
            20                  25                  30

Ile Gly Ile Val Gly Phe Ser Ile Arg Ala Phe Gly Ala Glu Glu Gln
        35                  40                  45

Ser Val Pro Asn Lys Gln Ser Gly Lys Leu Val Ile Trp Ile Asn Gly
    50                  55                  60

Asp Lys Gly Tyr Asn Gly Leu Ala Glu Val Gly Lys Lys Phe Glu Lys
65                  70                  75                  80

Asp Thr Gly Ile Lys Val Thr Val Glu His Pro Asp Lys Leu Glu Glu
                85                  90                  95

Lys Phe Pro Gln Val Ala Ala Thr Gly Asp Gly Pro Asp Ile Ile Phe
            100                 105                 110

Trp Ala His Asp Arg Phe Gly Gly Tyr Ala Gln Ser Gly Leu Leu Ala
        115                 120                 125

Glu Ile Thr Pro Asp Lys Ala Phe Gln Asp Lys Leu Tyr Pro Phe Thr
    130                 135                 140

Trp Asp Ala Val Arg Tyr Asn Gly Lys Leu Ile Ala Tyr Pro Ile Ala
145                 150                 155                 160

Val Glu Ala Leu Ser Leu Ile Tyr Asn Lys Asp Leu Leu Pro Asn Pro
                165                 170                 175

Pro Lys Thr Trp Glu Glu Ile Pro Ala Leu Asp Lys Glu Leu Lys Ala
            180                 185                 190

Lys Gly Lys Ser Ala Leu Met Phe Asn Leu Gln Glu Pro Tyr Phe Thr
        195                 200                 205

Trp Pro Leu Ile Ala Ala Asp Gly Gly Tyr Ala Phe Lys Tyr Glu Asn
    210                 215                 220

Gly Lys Tyr Asp Ile Lys Asp Val Gly Val Asp Asn Ala Gly Ala Lys
225                 230                 235                 240

Ala Gly Leu Thr Phe Leu Val Asp Leu Ile Lys Asn Lys His Met Asn
                245                 250                 255

Ala Asp Thr Asp Tyr Ser Ile Ala Glu Ala Ala Phe Asn Lys Gly Glu
            260                 265                 270

Thr Ala Met Thr Ile Asn Gly Pro Trp Ala Trp Ser Asn Ile Asp Thr
        275                 280                 285

Ser Lys Val Asn Tyr Gly Val Thr Val Leu Pro Thr Phe Lys Gly Gln
    290                 295                 300

Pro Ser Lys Pro Phe Val Gly Val Leu Ser Ala Gly Ile Asn Ala Asp
305                 310                 315                 320

Asn Lys Glu Leu Ala Lys Glu Phe Leu Glu Asn Tyr Leu Leu Thr Asp

```
                    325                 330                 335
Glu Gly Leu Glu Ala Val Asn Lys Asp Lys Pro Leu Gly Ala Val Leu
                340                 345                 350
Lys Ser Tyr Glu Glu Leu Val Lys Asp Pro Arg Ile Ala Ala Thr
            355                 360                 365
Met Glu Asn Ala Gln Lys Gly Glu Ile Met Pro Asn Ile Pro Gln Met
        370                 375                 380
Ser Ala Phe Trp Tyr Ala Val Arg Thr Ala Val Ile Asn Ala Ala Ser
385                 390                 395                 400
Gly Arg Gln Thr Val Asp Glu Ala Leu Lys Asp Ala Gln Thr Asn Ser
                405                 410                 415
Ser Lys Leu Thr Ile Ser Lys Thr Val Thr Gly Thr Ile Ala Asp Lys
            420                 425                 430
Lys Lys Glu Phe Asn Phe Glu Ile His Leu Lys Ser Ser Asp Gly Gln
        435                 440                 445
Ala Ile Ser Gly Thr Tyr Pro Thr Asn Ser Gly Glu Leu Thr Val Thr
    450                 455                 460
Asp Gly Lys Ala Thr Phe Thr Leu Lys Asp Gly Glu Ser Leu Ile Val
465                 470                 475                 480
Glu Gly Leu Pro Ser Gly Tyr Ser Tyr Glu Ile Thr Glu Thr Gly Ala
                485                 490                 495
Ser Asp Tyr Glu Val Ser Val Asn Gly Lys Asn Ala Pro Asp Gly Lys
            500                 505                 510
Ala Thr Lys Ala Ser Val Lys Glu Asp Glu Thr Val Ala Phe Glu Asn
        515                 520                 525
Arg Ser Asp Leu Val Pro Pro Thr Gly Leu Thr Thr Asp Gly Ala Ile
    530                 535                 540
Tyr Leu Trp Leu Leu Leu Val Pro Phe Gly Leu Leu Val Trp Leu
545                 550                 555                 560
Phe Gly Arg Lys Gly Thr Lys Lys
                565

<210> SEQ ID NO 100
<211> LENGTH: 44
<212> TYPE: PRT
<213> ORGANISM: Streptococcus pyogenes

<400> SEQUENCE: 100

Leu Gln Lys Arg Asp Lys Thr Asn Tyr Gly Ser Ala Asn Asn Lys Arg
1               5                   10                  15
Arg Gln Thr Thr Ile Gly Leu Leu Lys Val Phe Leu Thr Phe Val Leu
                20                  25                  30
Ile Gly Ile Val Gly Phe Ser Ile Arg Ala Phe Gly
            35                  40

<210> SEQ ID NO 101
<211> LENGTH: 119
<212> TYPE: PRT
<213> ORGANISM: Streptococcus pyogenes

<400> SEQUENCE: 101

Lys Leu Thr Ile Ser Lys Thr Val Thr Gly Thr Ile Ala Asp Lys Lys
1               5                   10                  15
Lys Glu Phe Asn Phe Glu Ile His Leu Lys Ser Ser Asp Gly Gln Ala
                20                  25                  30
Ile Ser Gly Thr Tyr Pro Thr Asn Ser Gly Glu Leu Thr Val Thr Asp
```

```
                   35                  40                  45
Gly Lys Ala Thr Phe Thr Leu Lys Asp Gly Glu Ser Leu Ile Val Glu
 50                  55                  60

Gly Leu Pro Ser Gly Tyr Ser Tyr Glu Ile Thr Glu Thr Gly Ala Ser
 65                  70                  75                  80

Asp Tyr Glu Val Ser Val Asn Gly Lys Asn Ala Pro Asp Gly Lys Ala
                 85                  90                  95

Thr Lys Ala Ser Val Lys Glu Asp Glu Thr Val Ala Phe Glu Asn Arg
            100                 105                 110

Lys Asp Leu Val Pro Pro Thr
            115

<210> SEQ ID NO 102
<211> LENGTH: 524
<212> TYPE: PRT
<213> ORGANISM: Streptococcus pyogenes

<400> SEQUENCE: 102

Ala Glu Glu Gln Ser Val Pro Asn Lys Gln Ser Gly Lys Leu Val Ile
 1               5                  10                  15

Trp Ile Asn Gly Asp Lys Gly Tyr Asn Gly Leu Ala Glu Val Gly Lys
                20                  25                  30

Lys Phe Glu Lys Asp Thr Gly Ile Lys Val Thr Val Glu His Pro Asp
            35                  40                  45

Lys Leu Glu Glu Lys Phe Pro Gln Val Ala Ala Thr Gly Asp Gly Pro
 50                  55                  60

Asp Ile Ile Phe Trp Ala His Asp Arg Phe Gly Gly Tyr Ala Gln Ser
 65                  70                  75                  80

Gly Leu Leu Ala Glu Ile Thr Pro Asp Lys Ala Phe Gln Asp Lys Leu
                 85                  90                  95

Tyr Pro Phe Thr Trp Asp Ala Val Arg Tyr Asn Gly Lys Leu Ile Ala
            100                 105                 110

Tyr Pro Ile Ala Val Glu Ala Leu Ser Leu Ile Tyr Asn Lys Asp Leu
            115                 120                 125

Leu Pro Asn Pro Pro Lys Thr Trp Glu Glu Ile Pro Ala Leu Asp Lys
            130                 135                 140

Glu Leu Lys Ala Lys Gly Lys Ser Ala Leu Met Phe Asn Leu Gln Glu
145                 150                 155                 160

Pro Tyr Phe Thr Trp Pro Leu Ile Ala Ala Asp Gly Gly Tyr Ala Phe
                165                 170                 175

Lys Tyr Glu Asn Gly Lys Tyr Asp Ile Lys Asp Val Gly Val Asp Asn
            180                 185                 190

Ala Gly Ala Lys Ala Gly Leu Thr Phe Leu Val Asp Leu Ile Lys Asn
            195                 200                 205

Lys His Met Asn Ala Asp Thr Asp Tyr Ser Ile Ala Glu Ala Ala Phe
            210                 215                 220

Asn Lys Gly Glu Thr Ala Met Thr Ile Asn Gly Pro Trp Ala Trp Ser
225                 230                 235                 240

Asn Ile Asp Thr Ser Lys Val Asn Tyr Gly Val Thr Val Leu Pro Thr
                245                 250                 255

Phe Lys Gly Gln Pro Ser Lys Pro Phe Val Gly Val Leu Ser Ala Gly
            260                 265                 270

Ile Asn Ala Asp Asn Lys Glu Leu Ala Lys Glu Phe Leu Glu Asn Tyr
            275                 280                 285
```

```
Leu Leu Thr Asp Glu Gly Leu Glu Ala Val Asn Lys Asp Lys Pro Leu
            290                 295                 300

Gly Ala Val Leu Lys Ser Tyr Glu Glu Leu Val Lys Asp Pro Arg
305                 310                 315                 320

Ile Ala Ala Thr Met Glu Asn Ala Gln Lys Gly Glu Ile Met Pro Asn
                    325                 330                 335

Ile Pro Gln Met Ser Ala Phe Trp Tyr Ala Val Arg Thr Ala Val Ile
                340                 345                 350

Asn Ala Ala Ser Gly Arg Gln Thr Val Asp Glu Ala Leu Lys Asp Ala
                355                 360                 365

Gln Thr Asn Ser Ser Lys Leu Thr Ile Ser Lys Thr Val Thr Gly Thr
    370                 375                 380

Ile Ala Asp Lys Lys Lys Glu Phe Asn Phe Glu Ile His Leu Lys Ser
385                 390                 395                 400

Ser Asp Gly Gln Ala Ile Ser Gly Thr Tyr Pro Thr Asn Ser Gly Glu
                    405                 410                 415

Leu Thr Val Thr Asp Gly Lys Ala Thr Phe Thr Leu Lys Asp Gly Glu
                420                 425                 430

Ser Leu Ile Val Glu Gly Leu Pro Ser Gly Tyr Ser Tyr Glu Ile Thr
                435                 440                 445

Glu Thr Gly Ala Ser Asp Tyr Glu Val Ser Val Asn Gly Lys Asn Ala
    450                 455                 460

Pro Asp Gly Lys Ala Thr Lys Ala Ser Val Lys Glu Asp Glu Thr Val
465                 470                 475                 480

Ala Phe Glu Asn Arg Ser Asp Leu Val Pro Pro Thr Gly Leu Thr Thr
                    485                 490                 495

Asp Gly Ala Ile Tyr Leu Trp Leu Leu Leu Val Pro Phe Gly Leu
                500                 505                 510

Leu Val Trp Leu Phe Gly Arg Lys Gly Thr Lys Lys
            515                 520

<210> SEQ ID NO 103
<211> LENGTH: 711
<212> TYPE: PRT
<213> ORGANISM: Streptococcus pyogenes

<400> SEQUENCE: 103

Met Gln Lys Arg Asp Lys Thr Asn Tyr Gly Ser Ala Asn Asn Lys Arg
1               5                   10                  15

Arg Gln Thr Thr Ile Gly Leu Leu Lys Val Phe Leu Thr Phe Val Leu
                20                  25                  30

Ile Gly Ile Val Gly Phe Ser Ile Arg Ala Phe Gly Ala Glu Glu Gln
            35                  40                  45

Ser Val Pro Asn Lys Gln Ser Ser Val Gln Asp Tyr Pro Trp Tyr Gly
    50                  55                  60

Tyr Asp Ser Tyr Ser Lys Gly Tyr Pro Asp Tyr Ser Pro Leu Lys Thr
65                  70                  75                  80

Tyr His Asn Leu Lys Val Asn Leu Asp Gly Ser Lys Glu Tyr Gln Ala
                85                  90                  95

Tyr Cys Phe Asn Leu Thr Lys His Phe Pro Ser Lys Ser Asp Ser Val
                    100                 105                 110

Arg Ser Gln Trp Tyr Lys Lys Leu Glu Gly Thr Asn Glu Asn Phe Ile
                115                 120                 125

Lys Leu Ala Asp Lys Pro Arg Ile Glu Asp Gly Gln Leu Gln Gln Asn
            130                 135                 140
```

```
Ile Leu Arg Ile Leu Tyr Asn Gly Tyr Pro Asn Asp Arg Asn Gly Ile
145                 150                 155                 160

Met Lys Gly Ile Asp Pro Leu Asn Ala Ile Leu Val Thr Gln Asn Ala
            165                 170                 175

Ile Trp Tyr Tyr Thr Asp Ser Ser Tyr Ile Ser Asp Thr Ser Lys Ala
                180                 185                 190

Phe Gln Gln Glu Glu Thr Asp Leu Lys Leu Asp Ser Gln Gln Leu Gln
                195                 200                 205

Leu Met Arg Asn Ala Leu Lys Arg Leu Ile Asn Pro Lys Glu Val Glu
210                 215                 220

Ser Leu Pro Asn Gln Val Pro Ala Asn Tyr Gln Leu Ser Ile Phe Gln
225                 230                 235                 240

Ser Ser Asp Lys Thr Phe Gln Asn Leu Leu Ser Ala Glu Tyr Val Pro
            245                 250                 255

Asp Thr Pro Pro Lys Pro Gly Glu Glu Pro Ala Lys Thr Glu Lys
            260                 265                 270

Thr Ser Val Ile Ile Arg Lys Tyr Ala Glu Gly Asp Tyr Ser Lys Leu
        275                 280                 285

Leu Glu Gly Ala Thr Leu Lys Leu Ala Gln Ile Glu Gly Ser Gly Phe
290                 295                 300

Gln Glu Lys Ile Phe Asp Ser Asn Lys Ser Gly Glu Lys Val Glu Leu
305                 310                 315                 320

Pro Asn Gly Thr Tyr Val Leu Ser Glu Leu Lys Pro Pro Gln Gly Tyr
            325                 330                 335

Gly Val Ala Thr Pro Ile Thr Phe Lys Val Ala Ala Glu Lys Val Leu
            340                 345                 350

Ile Lys Asn Lys Glu Gly Gln Phe Val Glu Asn Gln Asn Lys Glu Ile
        355                 360                 365

Ala Glu Pro Tyr Ser Val Thr Ala Phe Asn Asp Phe Glu Glu Ile Gly
        370                 375                 380

Tyr Leu Ser Asp Phe Asn Asn Tyr Gly Lys Phe Tyr Tyr Ala Lys Asn
385                 390                 395                 400

Thr Asn Gly Thr Asn Gln Val Val Tyr Cys Phe Asn Ala Asp Leu His
            405                 410                 415

Ser Pro Pro Asp Ser Tyr Asp His Gly Ala Asn Ile Asp Pro Asp Val
            420                 425                 430

Ser Glu Ser Lys Glu Ile Lys Tyr Thr His Val Ser Gly Tyr Asp Leu
        435                 440                 445

Tyr Lys Tyr Ala Ala Thr Pro Arg Asp Lys Asp Ala Asp Phe Phe Leu
450                 455                 460

Lys His Ile Lys Lys Ile Leu Asp Lys Gly Tyr Lys Lys Gly Asp
465                 470                 475                 480

Thr Tyr Lys Thr Leu Thr Glu Ala Gln Phe Arg Ala Ala Thr Gln Leu
            485                 490                 495

Ala Ile Tyr Tyr Tyr Thr Asp Ser Ala Asp Leu Thr Thr Leu Lys Thr
            500                 505                 510

Tyr Asn Asp Asn Lys Gly Tyr His Gly Phe Asp Lys Leu Asp Asp Ala
        515                 520                 525

Thr Leu Ala Val Val His Glu Leu Ile Thr Tyr Ala Glu Asp Val Thr
    530                 535                 540

Leu Pro Met Thr Gln Asn Leu Asp Phe Phe Val Pro Asn Ser Ser Arg
545                 550                 555                 560
```

-continued

```
Tyr Gln Ala Leu Ile Gly Thr Gln Tyr His Pro Asn Glu Leu Ile Asp
            565             570                 575

Val Ile Ser Met Glu Asp Lys Gln Ala Pro Ile Ile Pro Ile Thr His
        580             585             590

Lys Leu Thr Ile Ser Lys Thr Val Thr Gly Thr Ile Ala Asp Lys Lys
        595             600             605

Lys Glu Phe Asn Phe Glu Ile His Leu Lys Ser Ser Asp Gly Gln Ala
    610             615             620

Ile Ser Gly Thr Tyr Pro Thr Asn Ser Gly Glu Leu Thr Val Thr Asp
625             630             635                 640

Gly Lys Ala Thr Phe Thr Leu Lys Asp Gly Glu Ser Leu Ile Val Glu
            645             650             655

Gly Leu Pro Ser Gly Tyr Ser Tyr Glu Ile Thr Glu Thr Gly Ala Ser
            660             665             670

Asp Tyr Glu Val Ser Val Asn Gly Lys Asn Ala Pro Asp Gly Lys Ala
        675             680             685

Thr Lys Ala Ser Val Lys Glu Asp Glu Thr Val Ala Phe Glu Asn Arg
    690             695             700

Lys Asp Leu Val Pro Pro Thr
705             710
```

METHODS AND COMPOSITIONS FOR THE DISPLAY OF POLYPEPTIDES ON THE PILI OF GRAM-POSITIVE BACTERIA

CROSS-REFERENCE TO RELATED APPLICATIONS

This Application is a continuation of U.S. application Ser. No. 12/990,264 filed Mar. 8, 2011, which is the National Stage of International Application Number PCT/US2009/043286 filed May 8, 2009, which claims the benefit of priority to U.S. Provisional Application Nos. 61/126,883 filed May 8, 2008 and 61/088,250 filed Aug. 12, 2008, all hereby incorporated by reference in their entireties.

STATEMENT REGARDING FEDERALLY FUNDED RESEARCH

This invention was made with Government support under Grant No. R01 A1055605 awarded by the National Institutes of Health. The Government has certain rights in the invention.

FIELD OF THE INVENTION

The present invention relates to the field of microbial polypeptide display.

BACKGROUND OF THE INVENTION

Heterologous surface display of proteins on recombinant microorganisms involves the targeting and anchoring of heterologous proteins to the outer surface of host-cells such as yeast, fungi, mammalian and plant cells. Display of heterologous proteins at these cells' surfaces can take many forms, varying from the expression of reactive groups such as antigenic determinants, heterologous enzymes, (single-chain) antibodies, polyhistidyl tags, peptides, and other compounds. Heterologous surface display has been applied as a tool for research in microbiology, molecular biology, vaccinology, and biotechnology.

BRIEF SUMMARY OF THE INVENTION

The present invention provides methods and compositions for the display of at least one polypeptide of interest on the tip of pili of Gram-positive bacteria. Methods comprise introducing into a Gram-positive bacterium a polynucleotide that encodes a chimeric polypeptide to produce a transformed Gram-positive bacterium expressing the chimeric polypeptide. The chimeric polypeptide comprises the polypeptide of interest and a Gram-positive bacterial pilus tip protein or an active variant or fragment thereof. The pilus tip protein, active variant or fragment thereof comprises a cell wall sorting signal (CWSS) and is carboxyl to the polypeptide of interest. The Gram-positive bacterium expressing the chimeric polypeptide also expresses a tip sortase and a pilus shaft polypeptide. The transformed Gram-positive bacterium is then grown under conditions wherein the pili are formed. The pili produced by the transformed bacteria display the polypeptide of interest.

Compositions comprise Gram-positive bacterium comprising a polypeptide of interest covalently attached to the tip of a pilus, wherein the polypeptide of interest is amino terminal to a Gram-positive bacterial pilus tip protein or an active variant or fragment thereof, wherein the active variant or fragment comprises a cleaved cell wall sorting signal (CWSS) motif. The Gram-positive bacterium displaying a polypeptide of interest on the tip of pili that are disclosed herein are useful in methods for immunizing a subject with an antigen, methods for removing contaminants from a composition (e.g., soil, water), and methods for improving food products.

BRIEF DESCRIPTION OF THE FIGURES

FIGS. 2A-2C show the identification of the Cpa(HA)-T3 dimer in *E. coli*. Cell lysates of *E. coli* TOP10 containing plasmid pCR2.1 (lane 1), pJRS1325 (lane 2), and pJRS1326 (lane 3) analyzed:

FIG. 2A presents a Western blot reacted of whole cell lysates with anti-HA antiserum (reproduced from Zähner and Scott (2008) *J Bacteriol* 190:527-535);

FIG. 2B shows the results of immunoprecipitation of a crude extract with "EZview Red Anti-HA Affinity Gel", followed by boiling in SDS and SDS PAGE stained with SYPRORuby. Monomeric Cpa(HA) (Cpa), the putative Cpa-(HA)-T3 dimer (Cpa-T3), and the light chain (lc) and heavy chain (hc) of IgG are indicated on the right; and FIG. 2C presents the protein sequence of T3 (SEQ ID NO: 7) with regions covered by tryptic peptides identified by mass spectrometry indicated in bold. The N-terminal signal peptide (SP) and the C-terminal cell wall sorting signal (CWSS) are underlined.

FIGS. 3A and 3B show a Western immunoblot analysis of hot SDS-treated cell lysates of *E. coli* TOP10 containing plasmids pJRS1325 (lane 1), pEU7646 (lane 2), and pEU7904 (lane 3) reacted with (FIG. 3A) monoclonal anti-HA antibody or (FIG. 3B) polyclonal anti-T3 antiserum. The anti-T3 antiserum also reacts weakly with Cpa(HA). The locations of the Cpa(HA) monomer (Cpa), the Cpa(HA)-T3 heterodimer (Cpa-T3), and the T3 monomer (T3) and dimer (T3-T3) are indicated on the right; and FIGS. 3C and 3D show a Western immunoblot analysis of cell lysates of *E. coli* TOP10 containing plasmids pJRS1325 (lane 1), pEU7646 (lane 2), and pEU7905 (lane 3) reacted with (FIG. 3C) anti-T3 antiserum or (FIG. 3D) anti-HA antibody. The locations of the Cpa(HA) monomer (Cpa), the Cpa(HA)-T3 heterodimer (Cpa-T3), and the T3 monomer (T3) and dimer (T3-T3) are indicated. The sizes of molecular mass standards (in kilodaltons) are indicated to the left.

FIG. 4A shows a Western immunoblot analysis of cell wall extracts (lanes 1-4) and 10-fold concentrated supernatants (lanes 5-8) from GAS strains JRS4/pJRS9545 (lanes 1 and 5), JRS4/pJRS9550 (lanes 2 and 6), JRS4/pJRS9554

(lanes 3 and 7), and JRS4/pJRS9597 (lanes 4 and 8) analyzed with a monoclonal anti-HA antibody.

Figure 4A:
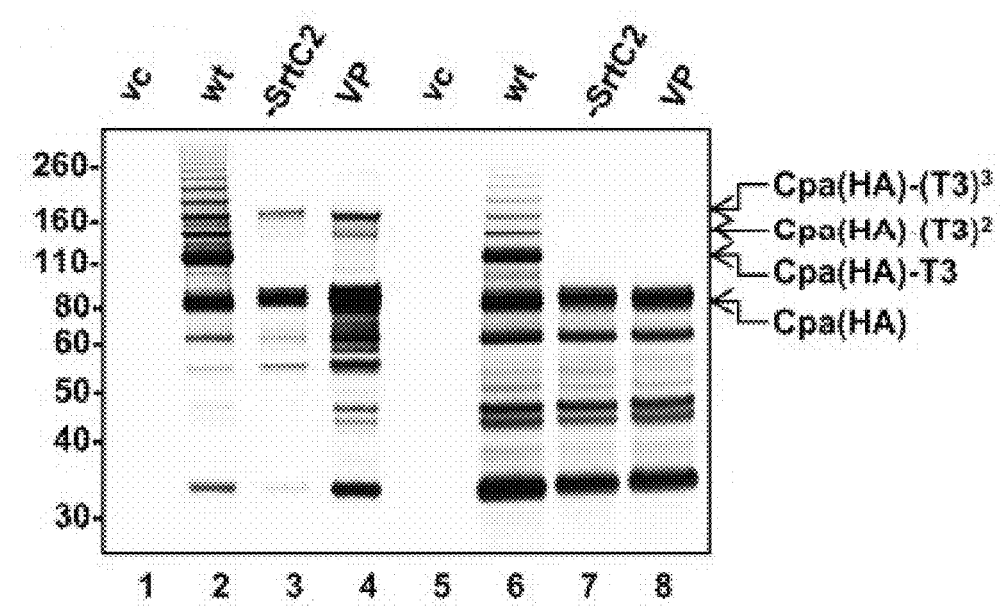
FIGS. 4A and 4B shows that the mutation of the Cpa CWSS motif from VPPTG to VP prevents the formation of the Cpa(HA)-T3 heterodimer and incorporation of Cpa into HMW pilus polymers in GAS.
Figure 4B:
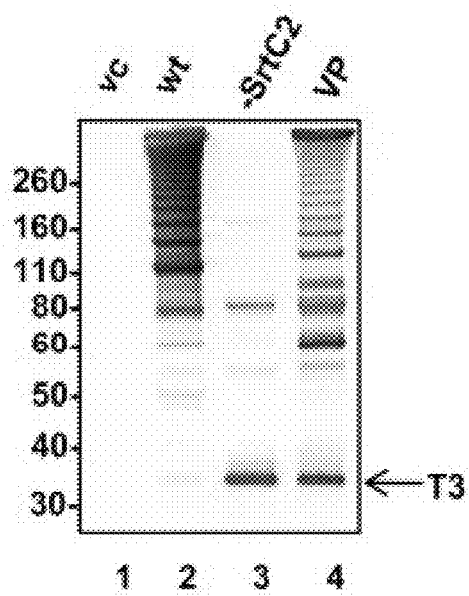

FIG. 4B shows a Western immunoblot analysis of the same cell wall extracts from JRS4/pJRS9545 (lane 1), JRS4/pJRS9550 (lane 2), JRS4/pJRS9554 (lane 3), and JRS4/pJRS9597 (lane 4) analyzed with polyclonal anti-T3 antiserum. Molecular masses are indicated to the left of the figures. The locations of the Cpa monomer (CPa(HA)), the Cpa-T3 heterodimer (Cpa(HA)-T3), Cpa linked to a T3 homodimer (Cpa(HA)-(T3)$^2$), Cpa linked to a T3 homotrimer (Cpa(HA)-(T3)$^3$), and the T3 monomer (T3) are indicated on the right of FIGS. 4A and 4B. pJRS9545 is derived from pJRS9508, and consists of the pReg696 backbone and the P23 promoter. (wt): wild type; (vc): vector control FIG. 5 shows a sequence alignment of the amino acid sequences of Group A Streptococcus major pilin proteins. Strains shown represent the different serotypes containing: FCT-2 (M1), FCT4 (M12, M28), or FCT-3 (all others) regions. The M type is indicated followed by the strain name. Invariant lysine residues are indicated in red (K43, K81, K100, K106, K173, and K191). Residues predicted to be involved in intramolecular bond formation are indicated in blue (aspartic acid; N180 and N307) and brown (glutamic acid; E129 and E264). The positions indicated for K, N, E are deduced from homology to the T3 sequence. The amino acid sequence of the major pilin protein for M3_MGAS315 strain is set forth in SEQ ID NO: 36; M1_SF370 is SEQ ID NO: 37; M28_MGAS6180 is SEQ ID NO: 38; emmstD33_D633 is SEQ ID NO: 39; M49_591 is SEQ ID NO: 40; M18_MGAS8232 is SEQ ID NO: 41; emm33_29487 is SEQ ID NO: 42; M5_Manfredo is SEQ ID NO: 43; and M12_A735 is SEQ ID NO: 44.

FIGS. 6A-C show the effect of replacement of lysine with alanine or arginine in T3 on T3 polymerization in E. coli. Western immunoblots reacted with polyclonal anti-T3 antiserum.

FIG. 6A shows cell lysates of E. coli TOP10 strains containing plasmid: pEU7655 (lane 1), pEU7657 (lane 2), pEU7678 (lane 3), pEU7679 (lane 4), pEU7680 (lane 5), pEU7681 (lane 6), pEU7682 (lane 7);

FIG. 6B shows E. coli TOP10 strains containing plasmid: pEU7655 (lane 1), pEU7657 (lane 2), pEU7678 (lane 3), pEU7682 (lane 4), and pEU7909 (lane 5); and FIG. 6C shows E. coli TOP10 strains containing plasmid: pEU7655 (lane 1), pEU7657 (lane 2), pEU7907 (lane 3), pEU7692 (lane 4), and pEU7908 (lane 5). The position of the T3 monomer (T3), dimer (T3-T3), and trimer (T3)$^3$ are indicated on the right. The sizes of molecular mass standards (in kilodaltons) are indicated on the left.

Figure 7:
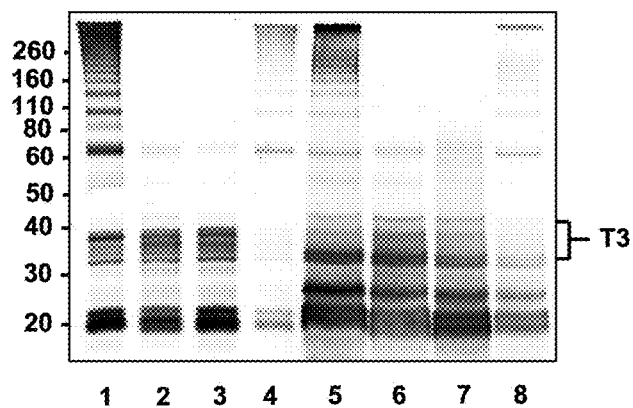

FIG. 7 shows the effect of replacement of lysine with alanine or arginine in T3 on T3 polymerization in GAS. A Western immunoblot analysis of cell wall extracts (lanes 1-4) and supernatants (lanes 5-8) of JRS4/pJRS9536 (lane 1, lane 5), pJRS9541 (lane 2, lane 6), pJRS9543 (lane 3, lane 7), pJRS9538 (lane 4, lane 8) reacted with monoclonal anti-HA antibody is shown. The position of the T3 monomer (T3) is indicated on the right. The sizes of molecular mass standards (in kilodaltons) are indicated on the left.

Figure 8A:
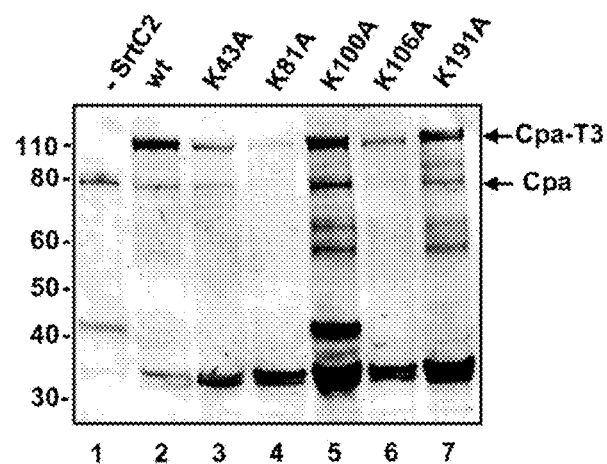

FIG. 8A shows the effect of replacement of lysine with alanine in T3 on Cpa(HA)-T3 heterodimer formation in E. coli. Western immunoblots are shown that were reacted with monoclonal anti-HA antibody: cell lysates of BL21(DE3) CodonPlus-RIL with pJRS1325 (lane 1), pEU7646 (lane 2), pEU7652 (lane 3), pEU7651 (lane 4), pEU7653 (lane 5), pEU7654 (lane 6), pEU7661 (lane 7). The Cpa(HA) monomer is labeled Cpa, and the Cpa(HA)-T3 heterodimer is labeled Cpa-T3. The sizes of molecular mass standards (in kilodaltons) are indicated on the left. wt, wild type.

Figure 8B:
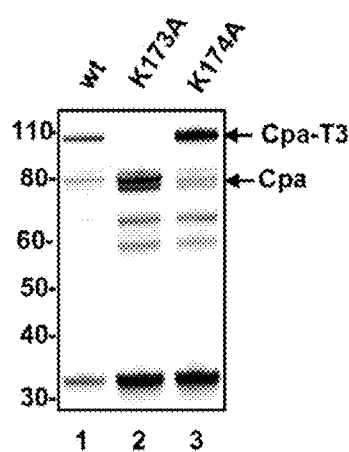

FIG. 8B shows E. coli TOP10 containing plasmid pEU7646 (lane 1), pEU7687 (lane 2), pEU7688 (lane 3). The Cpa(HA) monomer is labeled Cpa, and the Cpa(HA)-T3 heterodimer is labeled Cpa-T3. The sizes of molecular mass standards (in kilodaltons) are indicated on the left. wt, wild type.

Figure 9A:
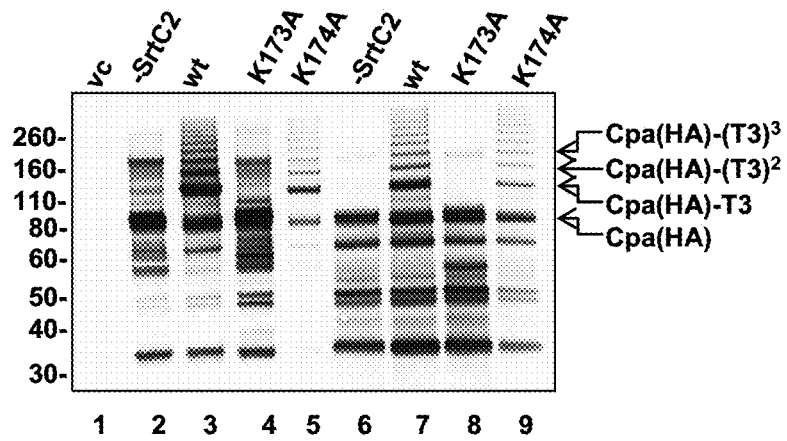
Figure 9B:
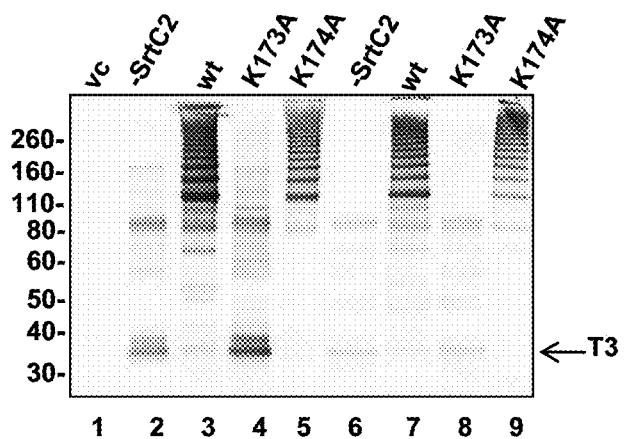

FIGS. 9A and 9B show the effect of replacement of lysine with alanine in T3 on incorporation of Cpa(HA) and T3 polymerization in GAS. Western immunoblots are shown with cell wall extracts (lanes 1-5) and supernatants (lanes 6-9) of JRS4/pJRS9545 (lane 1), JRS4/pJRS9554 (lanes 2 and 6), JRS4/pJRS9550 (lanes 3 and 7), JRS4/pJRS9557 (lanes 4 and 8), and JRS4/pJRS9558 (lanes 5 and 9) reacted with monoclonal anti-HA antibody (FIG. 9A) or polyclonal anti-T3 antiserum (FIG. 9B). (vc)=vector control.

Figure 10:
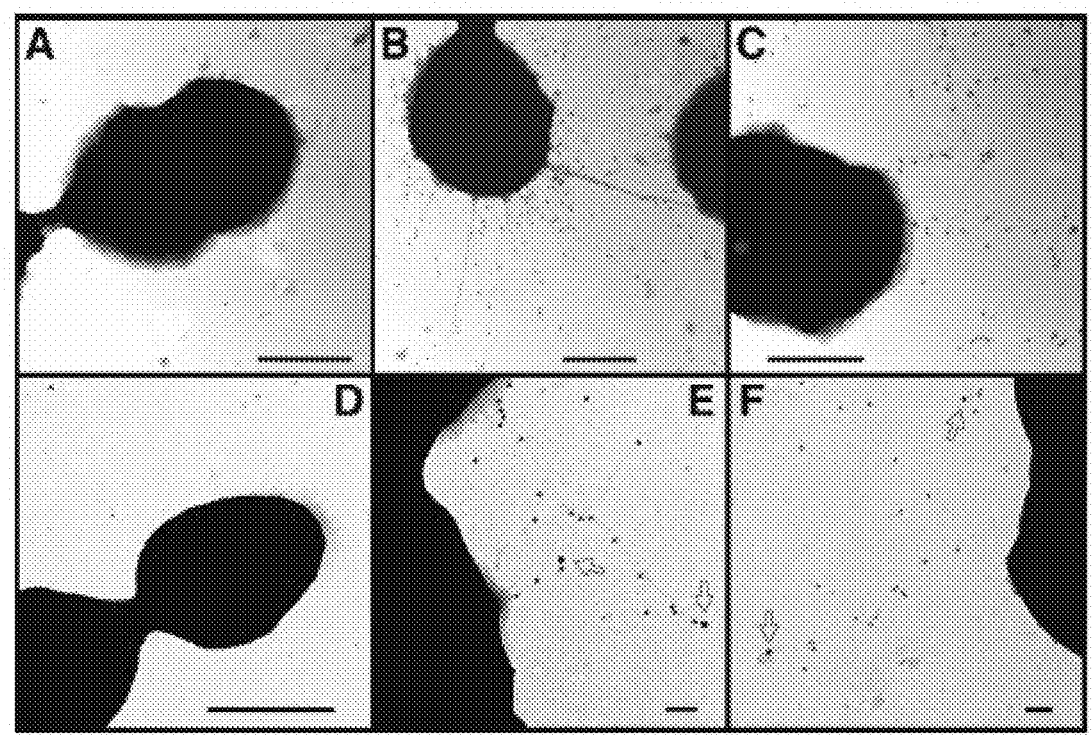

FIG. 10 provides photographs of whole-bacteria, negative-stain transmission electron microscopic images of JRS4/pJRS9545 (vector control; panels A and D) or JRS4/pJRS9550 (Cpa(HA), SipA2, T3, and SrtC2; panels B, C, E, and F). In panels A-C, the bacteria were incubated with anti-T3 antiserum, followed by an anti-rabbit secondary antibody conjugated to 12-nm diameter gold particles. In panels D-F, the bacteria were labeled with the anti-T3 antiserum as above, together with anti-HA antibody and an anti-mouse secondary antibody conjugated to 18-nm diameter gold particles. The larger gold particles, specific for Cpa(HA), could be seen at the tips of the pilus fibers (arrows in panels E and F). Scale bars=500 nm (panels A-D) or 100 nm (panels E and F).

Figure 11:
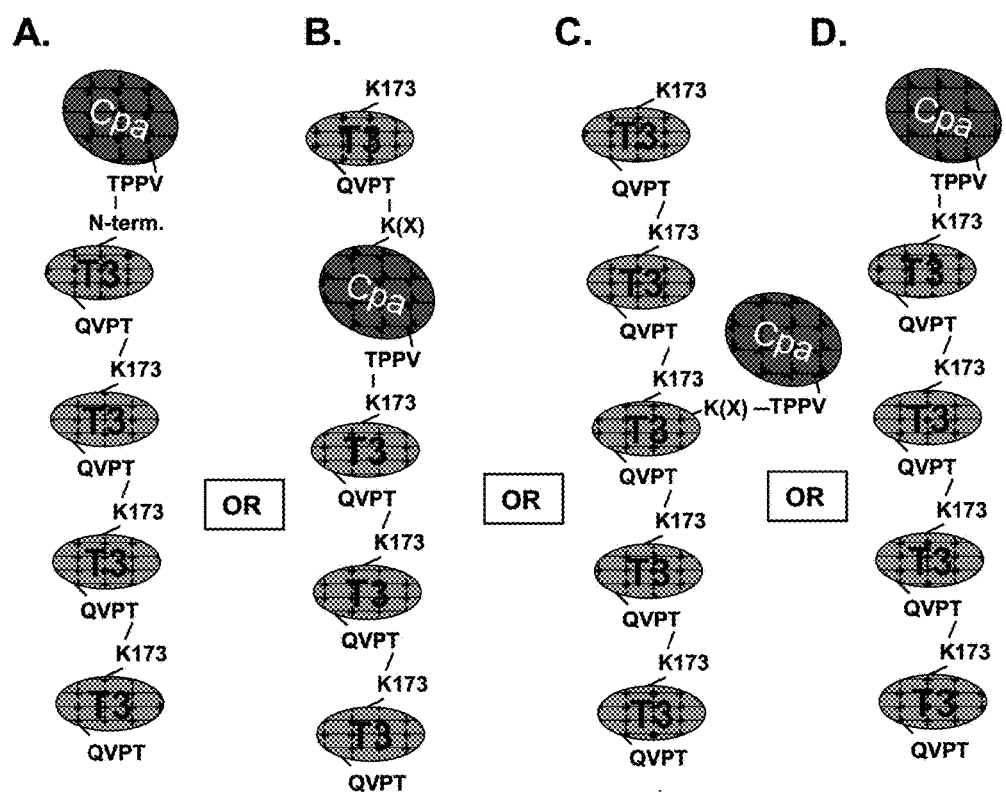

FIG. 11 illustrates alternative models of Cpa incorporation into the T3 pilus structure. In the first model (A), the minor pilin, Cpa, is attached by the VPPTG motif in its CWSS to the α-amino group at the N-terminus of the major pilin, T3. In the second model (B), the VPPTG motif (SEQ ID NO: 10) in the CWSS of Cpa is attached to K173 of T3 in place of a T3 subunit. An unknown K residue of Cpa is then used to bond to the QVPTG motif (SEQ ID NO: 9) of the CWSS of T3. This leads to a structure with Cpa interspersed among T3 subunits. In the third model (C), Cpa is linked to a K in T3 other than K173. In the fourth model (D), Cpa can only attach to K173 of T3, and therefore Cpa constitutes the tip of the pilus.

Figure 12:
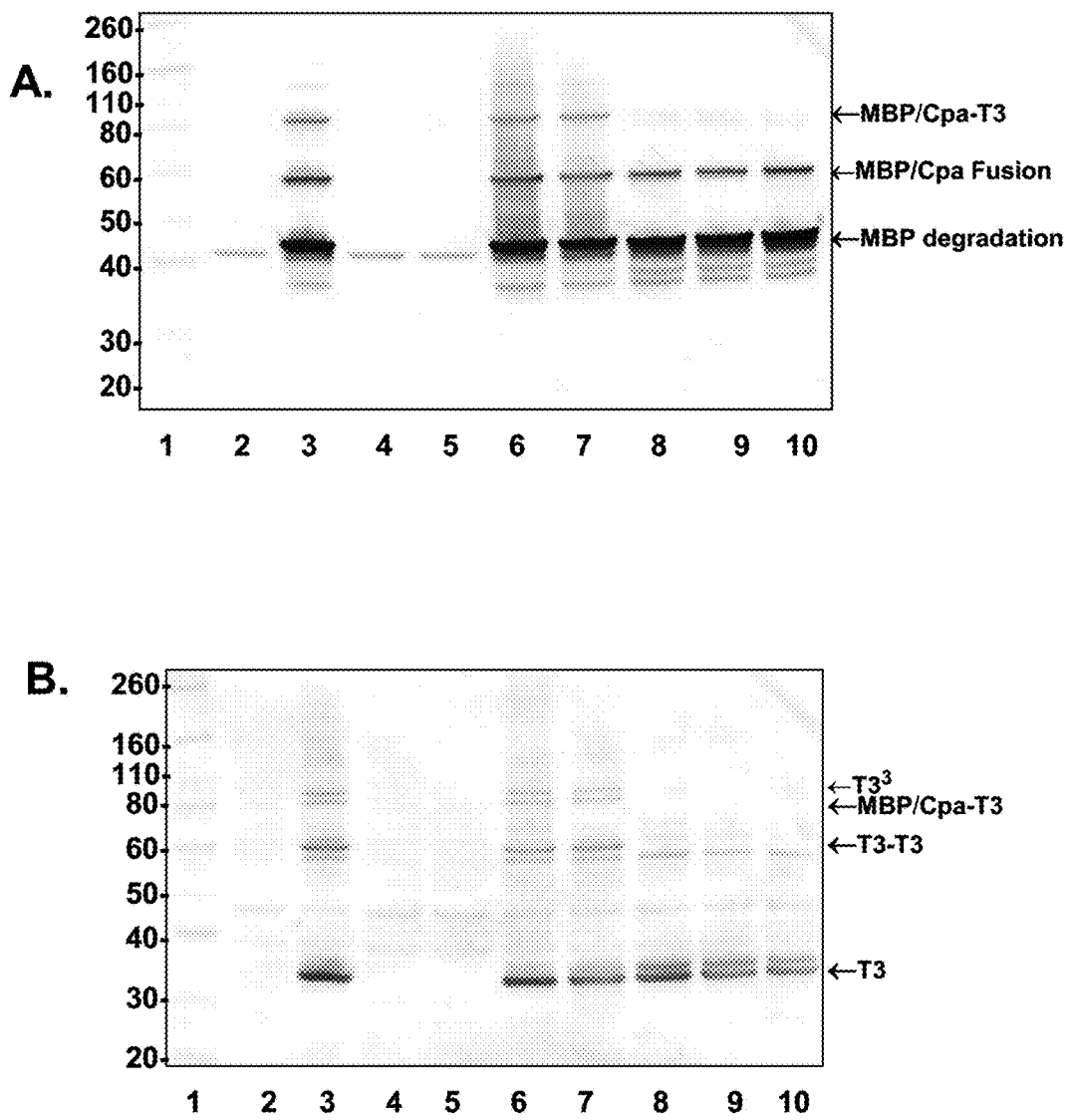

FIG. 12 shows the expression of MalE/Cpa fusion constructs in E. coli strain XL10. Constructs contain maltose binding protein (MBP)/Cpa through SrtC2 (pJRS9555) or MBP/Cpa through T3 (pJRS9556). The Western immunoblot in panel A was probed with an anti-MBP antibody, while the blot in panel B was probed with an anti-T3 antibody. Lanes 3, 6, 7 were confirmed by PCR to have the desired insert, lanes 2, 4, 5 lack this insert and lanes 8-10 lack srtC2. Lanes: (1) molecular mass standard, (2) pJRS9555.3, (3) pJRS9555.4, (4) pJRS9555.5, (5) pJRS9555.6, (6) pJRS9555.7, (7) pJRS9555.8, (8) pJRS9556.1, (9) pJRS9556.2, (10) pJRS9556.3.

Figure 13:
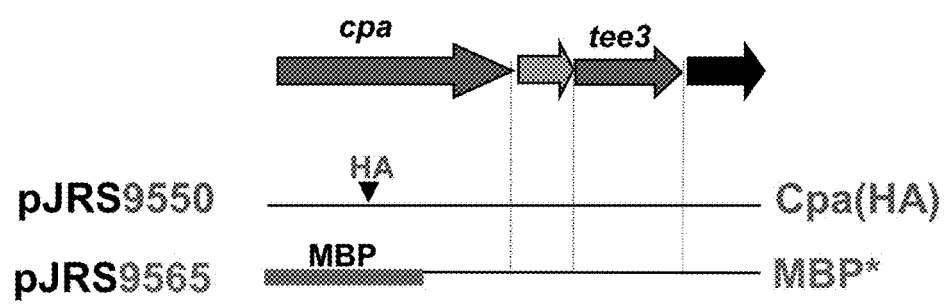

FIG. 13 provides a depiction of the regions encoded by the pJRS9550 and pJRS9565 plasmids.

Figure 14A:
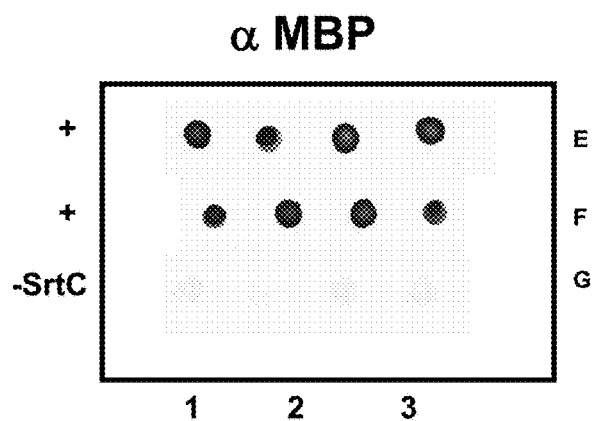
Figure 14B:
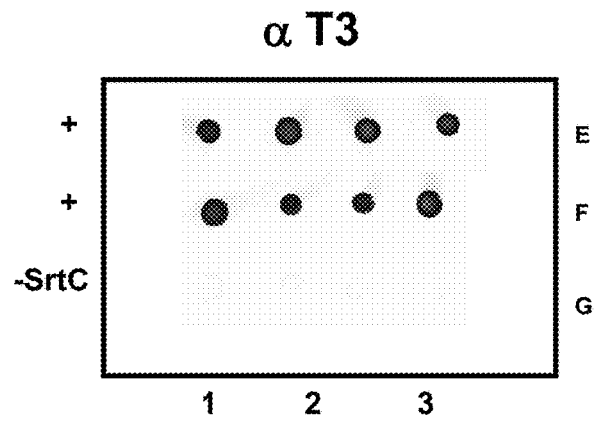

FIGS. 14A and 14B show the MBP/Cpa fusion protein (MBP*) is surface exposed in L. lactis. Whole cell dot blots of L. lactis MG1363 containing the plasmid pJRS9565 (lanes 1-4, rows E, F, (+)) or the pJRS9566 plasmid (lanes 1-4, row G, (−SrtC2)) were analyzed with a monoclonal anti-MBP antibody (FIG. 14A) or a polyclonal anti-T3 antibody (FIG. 14B).

Figure 15A:
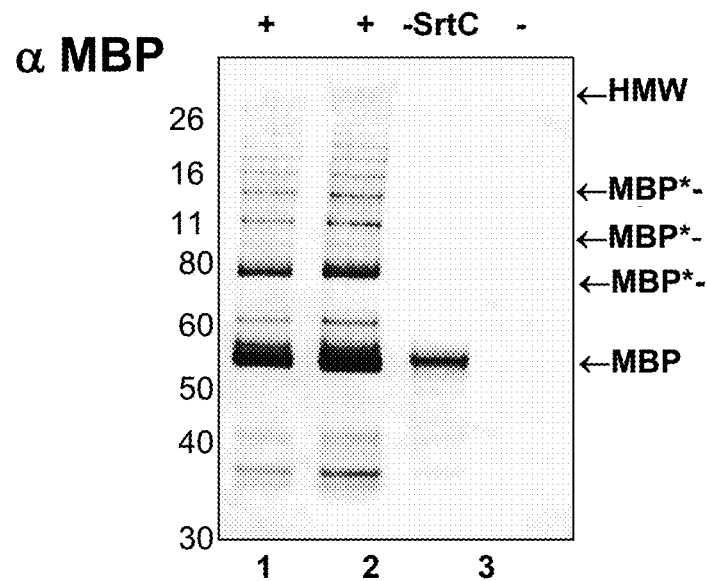
Figure 15B:
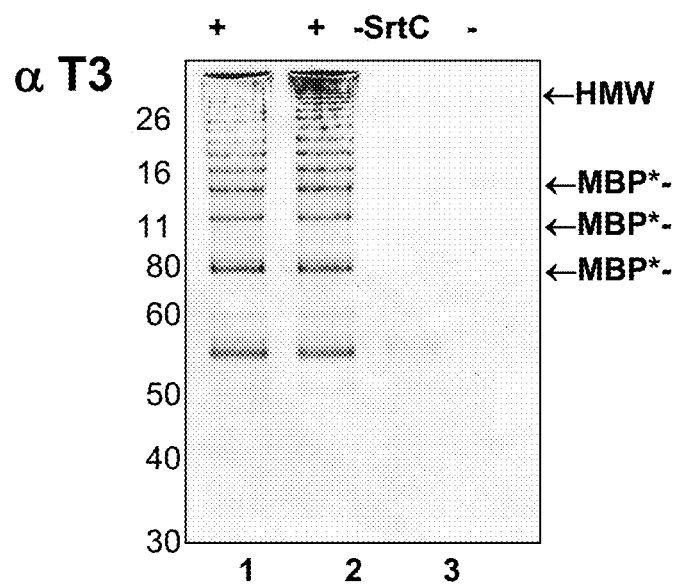

FIGS. 15A and 15B shows that the MBP/Cpa fusion protein (MBP*) is incorporated into T3 pili in L. lactis.

Figure 16A:
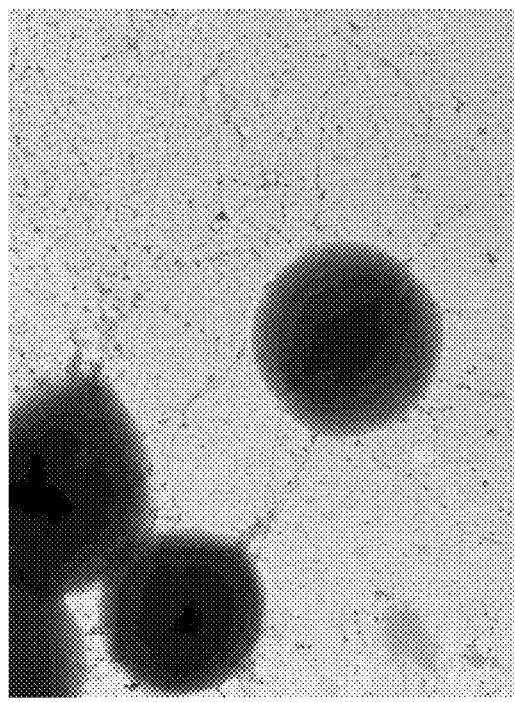
Figure 16B:
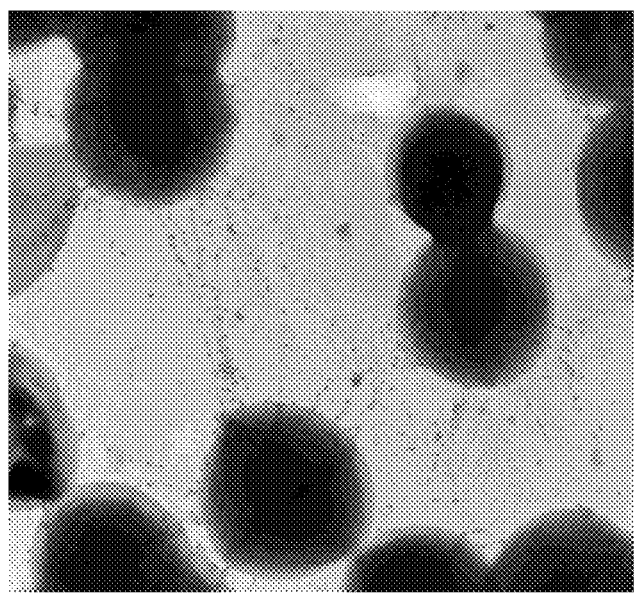
Figure 16C:
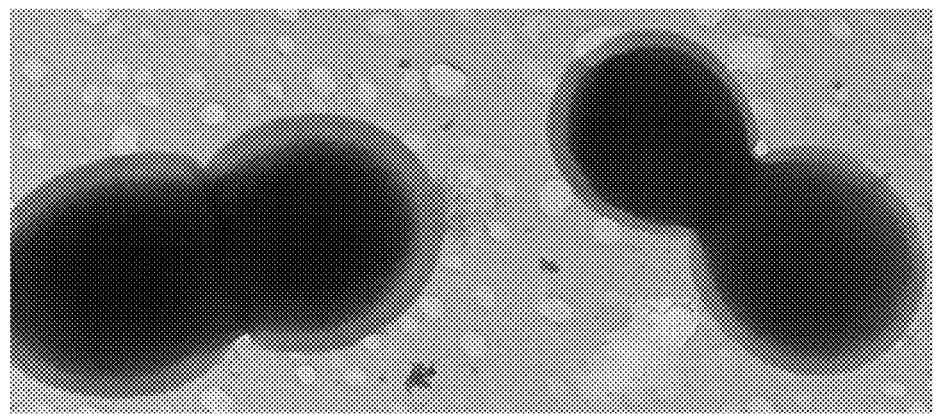

Western blot analyses are provided of *L. lactis* cell wall extracts of MG1363/pJRS9566 (lane 3, (−SrtC2)) and MG1363/pJRS9545 (lane 4, (−)) analyzed with a monoclonal anti-MBP antibody (FIG. 15A) or a polyclonal anti-T3 antibody (FIG. 15B). Molecular masses are indicated to the left of the figure. The locations of the MBP/Cpa fusion protein (MBP*), the MBP-Cpa-T3 heterotetramer (MBP*-(T3)$^3$) are shown to the right of the figure. HMW=high molecular mass species FIGS. 16A-16C provide photographs of immunogold electron microscopy (EM) of MBP*-T3 pili in *L. lactis* MG1363/pJRS9565. Whole-bacteria, negative-stain transmission EM of MG1363/pJRS9565 (FIGS. 16A and 16B) and MG1363/pJRS9545 (FIG. 16C, vector control) incubated with anti-T3 antiserum, followed by an anti-rabbit gold conjugate secondary antibody.

Figure 17A:
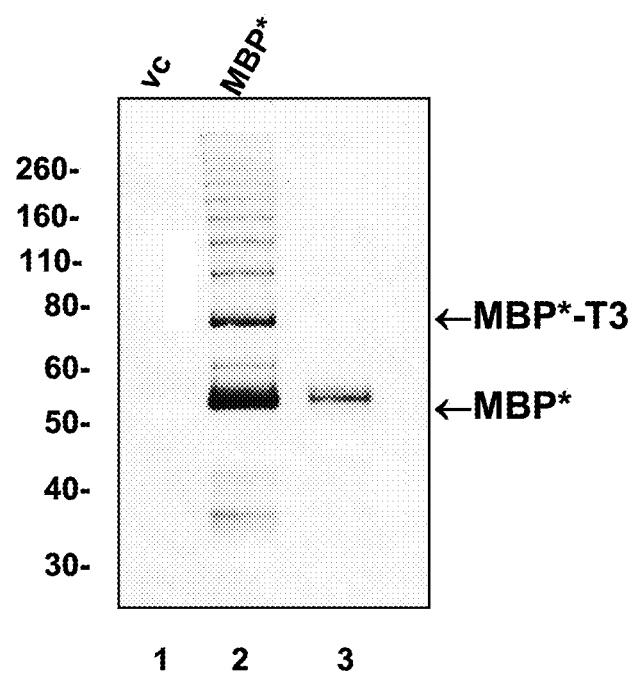
Figure 17B:
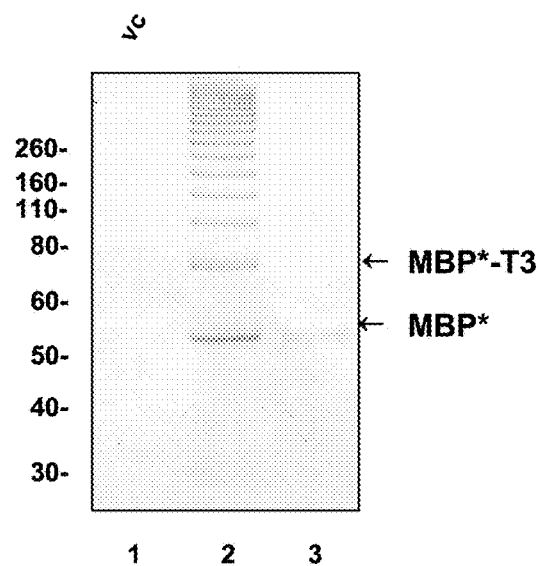

FIGS. 17A and 17B show that the MBP/Cpa fusion protein (MBP*) is synthesized in an active form in *L. lactis*. Lysates of MG1363/pJRS9545 (lane 1, (vc)), MG1363/pJRS9565 (lane 2, (MBP*)) and MG1363/pJRS9566 (lane 3, (−SrtC2)) were purified with amylose resin and analyzed with a monoclonal anti-MBP antibody (FIG. 17A) or polyclonal anti-T3 antiserum (FIG. 17B). Molecular masses are indicated to the left of the figure. The locations of the MBP/Cpa fusion protein (MBP*), and the MBP-Cpa-T3 heterodimer (MBP*-T3) are shown to the right of the figure.

Figure 18:
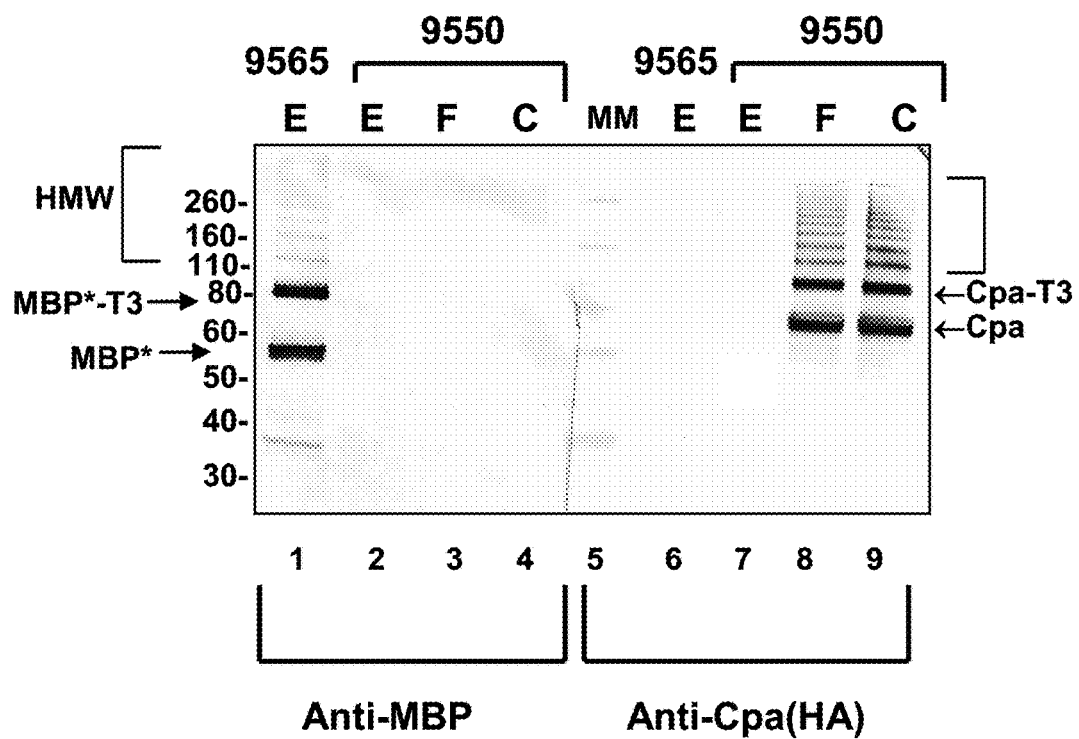

FIG. 18 shows that T3 pili containing the MBP/Cpa fusion protein (MBP*), but not wild type T3 pili bind to amylose resin. A Western blot analysis is provided of lysates of MG1363/pJRS9565 and MG1363/pJRS9550 that were purified using amylose resin. Samples corresponding to the eluate fraction of MG1363/pJRS9565 (lanes 1 and 6, (E)), and the eluate (lanes 2 and 7, (E)), flow through (lanes 3 and 8, (F)) and crude extract (lanes 4 and 9, (C)) fractions of MG1363/pJRS9550 were analyzed using monoclonal anti-MBP (lanes 1-4) or monoclonal anti-HA (lanes 6-9) antibodies. The locations of the MBP/Cpa fusion protein (MBP*), the MBP-Cpa-T3 heterodimer (MBP*-T3), the Cpa(HA) monomer (Cpa), and the Cpa(HA)-T3 heterodimer (Cpa-T3) are shown. Molecular masses are indicated to the left of the figure. HMW=high molecular mass species. MM=molecular mass standard.

Figure 19:
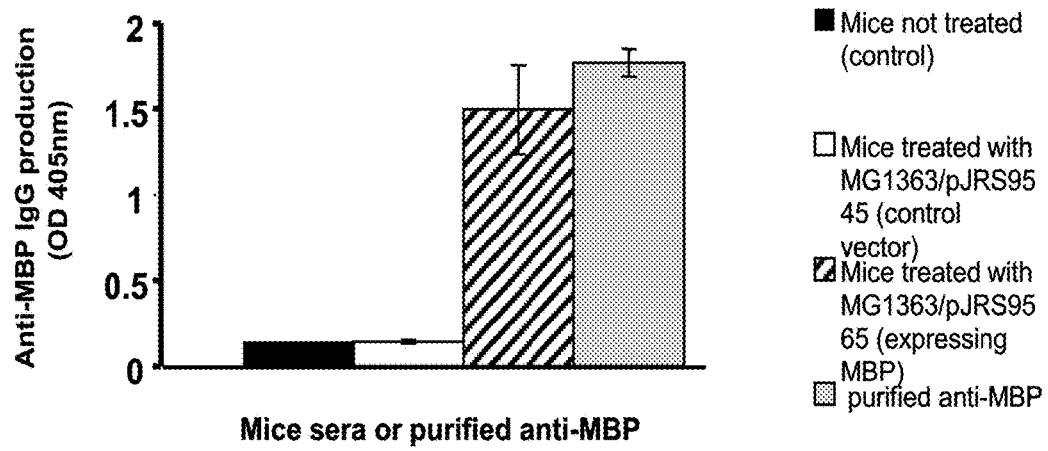

FIG. 19 provides a graph depicting the levels of anti-MBP IgG in sera of mice that were intranasally vaccinated with *L. lactis* MG1363/pJRS9545 (control vector) or with MG1363/pJRS9565 (expressing MBP). The bars represent an average of ten mice for the experimental groups and two mice for the control group.

Figure 20:
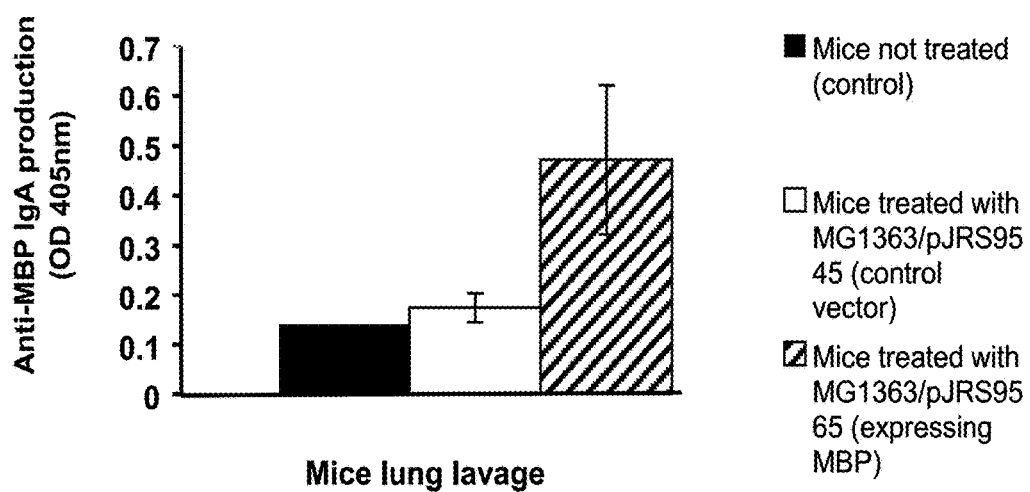

FIG. 20 provides a graph depicting the levels of anti-MBP IgA in lung lavage fluid of mice subjected that were intranasally vaccinated with *L. lactis* MG1363/pJRS9545 (control vector) or with MG1363/pJRS9565 (expressing MBP). The bars represent an average of ten mice for the experimental groups and two mice for the control group.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended embodiments. Although specific terms are employed herein, they are used in a generic and descriptive sense only and not for purposes of limitation.

It is to be noted that the term "a" or "an" entity refers to one or more of that entity; for example, "a bacterium" is understood to represent one or more bacteria. As such, the terms "a" (or "an"), "one or more," and "at least one" can be used interchangeably herein.

Throughout this specification and the embodiments, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The presently disclosed subject matter provides methods for producing Gram-positive bacteria having at least one polypeptide of interest attached to the tip of at least one pilus, wherein the method comprises introducing into a Gram-positive bacterium a polynucleotide comprising a nucleotide sequence that encodes a chimeric polypeptide. The chimeric polypeptide comprises the polypeptide of interest and a Gram-positive bacterial pilus tip protein, or an active variant or fragment thereof, wherein the pilus tip protein or active variant or fragment thereof comprises a cell wall sorting signal (CWSS). The chimeric polypeptide is expressed such that the pilus tip protein, variant, or fragment thereof is carboxyl to the heterologous polypeptide. The transformed Gram-positive bacterium additionally expresses a tip sortase and a pilus shaft polypeptide. The transformed Gram-positive bacterium is then grown under conditions that allow formation of the pilus.

Also disclosed herein are compositions comprising Gram-positive bacteria having at least one polypeptide of interest attached to the tip of at least one pilus. These Gram-positive bacteria find use in methods for inducing an immunological response in a subject through the administration of a Gram-positive bacterium where the polypeptide of interest comprises an antigen. The transformed Gram-positive bacteria of the invention also can be used in bioremediation methods, wherein a contaminant is removed from a composition (e.g., soil, water) via the introduction of a Gram-positive bacterium displaying a biosorbent that is capable of adsorbing the contaminant or an enzyme that is capable of degrading the contaminant. Other uses involve biocatalysis, screening for polypeptide expression, the production of biofuels, diagnostics, and use in probiotics.

Without being bound by any theory or mechanism of action, it is believed that the presence of the polypeptide of interest on the tip of the pili will remove the polypeptide further away from the bacterial capsule, enhancing the odds that the polypeptide will fold and function properly. Further, in those embodiments wherein the polypeptide of interest comprises an antigen, it is believed that displaying the polypeptide on the tip of the pili will maximize the exposure of the polypeptide to the cells of the immune system, enhancing the immunological response generated against the antigen.

There are two predominant types of bacteria that are categorized based on the composition and structure of the bacterial cell wall. Whether a given species of bacteria has one or the other type of cell wall can generally be determined by the cell's reaction to certain dyes. Perhaps the most widely-used dye for staining bacteria is the Gram stain. When stained with this crystal violet and iodine stain, bacteria which retain the stain are called Gram-positive, and those that do not are called Gram negative.

As used herein, by "Gram-positive bacteria" is meant a strain, type, species, or genera of bacteria that, when exposed to Gram stain, retains the dye and is, thus, stained blue-purple. The Gram-positive bacterial cell wall contains a relatively thick coat of peptidoglycan.

By contrast, a "Gram-negative bacteria" is meant a strain, type, species, or genera of bacteria that, when exposed to Gram stain does not retain the dye and thus, is not stained blue-purple.

Gram-positive bacteria useful for the presently disclosed methods and compositions include, but are not limited to, bacteria in the following genera: *Actinomyces, Bacillus, Bifidobacterium, Cellulomonas, Clostridium, Corynebacterium, Enterococcus, Lactococcus, Lactobacillus, Micrococcus, Mycobactenum, Nocardia, Staphylococcus, Streptococcus*, and *Streptomyces*. In some embodiments, the Gram-positive bacterium is selected from the group consisting of *Streptococcus pyogenes, Streptococcus gordinii, Lactococcus lactis, Staphylococcus xylosus*, and *Staphylococcus carnosus*. In particular embodiments, the Gram-positive bacterium comprises *Lactococcus lactis*.

The present invention takes advantage of the pili present on the surface of many different species of Gram positive bacteria, including Group A *Streptococcus* (GAS), such as *Streptococcus pyogenes* (Mora, M., G. et al. (2005) *Proc. Natl. Acad. Sci.* 102:15641-6.). As used herein, a "pilus" is a hair-like appendage found on the surface of a bacterium.

GAS pili have been shown to mediate attachment to primary human keratinocytes and to human tonsillar tissue, as well as to several tissue culture cell lines (Abbot, E. L. et al. (2007) *Cell Microbiol.* 9:1822-1833; Manetti, A. G. et al. (2007). *Mol. Microbiol.* 64:968-83). They have also been implicated in the formation of biofilms, which may be important for disease development (Manetti, A. G. et al. (2007) *Mol. Microbiol.* 64:968-83).

Pili on Gram-positive bacteria are composed of multiple subunits of a major backbone protein (referred to herein as the pilus shaft polypeptide) and may also have one or two minor pilin proteins attached thereto (Mandlik, A. et al. (2008) *Trends Microbiol.* 16:33-40; Scott, J. R. et al. (2006) *Mol. Microbiol.* 62:320-30; Telford, J. L. et al. (2006) *Nat. Rev. Microbiol.* 4:509-19). Gram-positive pilin subunits are covalently attached to each other and the polymerized pilus is covalently attached to the peptidoglycan of the cell wall (Swaminathan, A. et al. (2007) *Mol. Microbiol.* 66:961-974). The minor pilin proteins are not required for assembly of the pilus, although their presence may be important for physiological function and specificity of the pili. Prior to the present disclosure, the location of the minor pilins in the pilus structure was unknown and the method by which they are attached to the shaft was not yet understood.

Pilin proteins have the features typical of Gram-positive surface proteins, including an N-terminal signal sequence and a C-terminal cell wall sorting signal (CWSS), which is composed of a hydrophobic domain, beginning with LPXTG (SEQ ID NO: 1) or a similar motif, followed by a charged tail (Schneewind, O. et al. (1993). *Embo J.* 12:4803-11).

Proteins linked covalently to the Gram-positive cell wall are translocated across the cytoplasmic membrane in a Sec-dependent process, which is accompanied by cleavage of the N-terminal signal peptide. In the next step, a membrane-associated transpeptidase, referred to as the "housekeeping" sortase, cleaves the CWSS between the threonine (T) and glycine (G) residues of the LPXTG motif, producing an acyl-enzyme intermediate in which the carboxyl group of the threonine of the CWSS is linked to a cysteine residue of the transpeptidase. Subsequently, the threonine is transferred to an amino group of a constituent of the growing cell wall (the peptide crossbridge or diaminopimelic acid), thereby incorporating the protein into the cell wall (for reviews, see, for example, Marraffini et al. (2006) *Microbiol Mol Biol Rev* 70:192-221 and Scott and Barnett (2006) *Annu Rev Microbiol* 60:397-423), each of which are herein incorporated by reference in its entirety.

The genetic locus in which GAS pili are encoded varies between strains and has been named the FCT region for the proteins it encodes (Fibronectin-binding, Collagen-binding, T antigen (Bessen, D. E. et al. (2002) *Infect. Immun.* 70:1159-67). The FCT loci of the GAS strains whose sequence is currently available have been grouped into 6 classes (FCT1-6) based on gene content and gene order (Kratovac, Z. et al. (2007) *J Bacteriol.* 189:1299-310, which is herein incorporated by reference in its entirety). A given strain of GAS encodes only a single FCT locus, and therefore produces only a single type of pilus. GAS strains of the serotypes most common in the western world, M1, M3, M5, M18, and M49, contain either an FCT-2 region (M1) or an FCT-3 region (the others). The genes in these two FCT regions are highly homologous and they occur in the same order in each strain. The presently disclosed methods and compositions can utilize polypeptides (e.g., pilus tip proteins, pilus shaft polypeptides, tip sortases) from any strain of *S. pyogenes* bacteria. For example, the polypeptides used in the present invention can be a polypeptide encoded by a gene present on a FCT1, FCT2, FCT3, FCT4, FCT5, or FCT6 chromosomal region of a *S. pyogenes* bacterium. One or more of the polypeptides used in the present invention can be a polypeptide encoded by a strain of the serotype M1, M3, M5, M18, or M49 of *S. pyogenes* bacteria. In particular embodiments, one or more of the polypeptides are polypeptides encoded by a strain of serotype M3 of *S. pyogenes* bacteria. In certain embodiments, one or more of the polypeptides used in the invention (e.g., pilus shaft polypeptide, tip sortase, pilus tip polypeptide, pilin chaperone polypeptide) are encoded by the genes found in the FCT-3 region of the AM3 strain of *S. pyogenes*.

The protein encoded by the first gene in the FCT-3 operon (FIG. 1), cpa, is a minor pilin protein that has been shown to bind collagen (Podbielski, A. et al. (1999) *Mol. Microbiol.* 31:1051-64). For the M3 strain used in studies presented herein (the AM3 strain), the second gene (sipA2) is essential for pilus polymerization and probably acts as a chaperone (Zähner, D. et al. (2008) *J Bacteriol.* 190:527-35, which is herein incorporated by reference in its entirety). This gene is followed by tee3, which encodes the shaft protein T3, and by srtC2, encoding the pilin polymerase (Barnett, T. C. et al. (2004) *J Bacteriol.* 186:5865-75, which is herein incorporated by reference in its entirety). Recently Mora et al. elegantly demonstrated that the shaft protein of GAS pili corresponds to the trypsin-resistant (T) antigen long used for serological typing in GAS (Mora, M. et al. (2005) *Proc. Natl. Acad. Sci.* 102:15641-6). The last gene in the cluster, referred to as orfB, also encodes a minor pilin whose homologue was found by immunogold electron microscopy to be associated with the pilus structure of a serotype M1 strain (Mora, M. et al. (2005) *Proc. Natl. Acad. Sci.* 102: 15641-6). OrfB and Cpa can each be added to the pilus structure in the absence of the other, but, prior to the present disclosure, the residues linking these minor pilins to the major pilin were not defined.

The pilin proteins in the FCT-2, FCT-3, and FCT-4 regions of GAS strains contain CWSSs with motifs that differ from the canonical LPXTG (SEQ ID NO: 1) CWSS motif (Barnett, T. C. et al. (2004) *J. Bacteriol.* 186:5865-75). This may indicate that their polymerization requires a transpeptidase different from the housekeeping sortase. This has been demonstrated for the T3 protein, whose anchoring to the cell wall requires SrtC2, encoded in the FCT region, and not the housekeeping SrtA (Barnett, T. C. et al. (2004) *J. Bacteriol.* 186:5865-75). Previous results indicate that the noncanonical CWSS motif is needed for polymerization of the T3 protein, as the replacement of this noncanonical CWSS motif with the canonical LPSTG (SEQ ID NO: 2) motif prevents formation of T3 polymers (Zähner and Scott (2008) *J Bacteriol* 190:527-535).

The present invention provides Gram-positive bacterium having a polypeptide of interest covalently attached to the tip of a pilus through the introduction of a polynucleotide encoding a chimeric polypeptide into the bacterium. The chimeric polypeptide includes the polypeptide of interest linked in the proper reading frame to a pilus tip protein such that the polypeptide of interest is expressed as part of the pili on the transformed bacteria.

The terms "nucleic acid," "polynucleotide," or "oligonucleotide" generally are used herein in their art-accepted manners to refer to a polymer of nucleotides. As used herein, an oligonucleotide is typically less than 100 nucleotides in length. Polynucleotides can be single-stranded (with or without a secondary structure, e.g., hairpin) or double-stranded. Naturally occurring nucleic acids include deoxyribonucleic acid (DNA) and ribonucleic acid (RNA). The polynucleotide or oligonucleotide may include natural nucleosides (e.g., adenosine, thymidine, guanosine, cytidine, uridine, deoxyadenosine, deoxythymidine, deoxyguanosine, and deoxycytidine), or synthetic nucleosides, such as, nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), and/or nucleosides comprising chemically or biologically modified bases, such as those ribonucleosides that are substituted at the 2' position, for example, with an alkyl or alkyloxy group (e.g., methylated bases, such as those that are 2'-O-methylated, and 2'-O-methoxyethylated) or a fluoro group, intercalated bases, and/or modified sugars (e.g., 2'-fluororibose, ribose, 2'-deoxyribose, arabinose, and hexose). The phosphate groups in a polynucleotide or oligonucleotide are typically considered to form the internucleoside backbone of the polymer. In naturally occurring nucleic acids (e.g., DNA or RNA), the backbone linkage is via a 3' to 5' phosphodiester bond. Polynucleotides and oligonucletides containing modified backbones or non-naturally occurring internucleoside linkages, however, also can be used in the presently disclosed subject matter. Such modified backbones include backbones that have a phosphorus atom in the backbone and others that do not have a phosphorus atom in the backbone. Examples of modified linkages include, but are not limited to, phosphorothioate and 5'-N-phosphoramidite linkages. Polynucleotides and oligonucleotides need not be uniformly modified along the entire length of the molecule. For example, different nucleotide modifications, different backbone structures, and the like, may exist at various positions in the polynucleotide or oligonucleotide. Any of the polynucleotides described herein may utilize these modifications.

According to the presently disclosed methods, a polynucleotide comprising a nucleotide sequence that encodes a chimeric polypeptide is introduced into a Gram-positive bacterium. As used herein, the terms "polypeptide" or "peptide" or "protein" can be used interchangeably throughout, and refer to any monomeric or multimeric protein or peptide comprised of a polymer of amino acid residues. The term applies to amino acid polymers in which one or more amino acid residue is an artificial chemical analogue of a corresponding naturally occurring amino acid, as well as to naturally occurring amino acid polymers.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA). A "coding sequence" refers to a nucleotide sequence (e.g., DNA) that encodes a specific RNA or polypeptide.

The term "expression" has its meaning as understood in the art and refers to the process of converting genetic information encoded in a DNA sequence (coding sequence) into RNA (e.g., mRNA, rRNA, tRNA, or snRNA) through "transcription" of a polynucleotide (e.g., via the enzymatic action of an RNA polymerase), and for polypeptide-encoding polynucleotides, into a polypeptide through "translation" of mRNA. Thus, an "expression product" is, in general, an RNA transcribed from the coding sequence (e.g., either pre- or post-processing) or a polypeptide encoded by an RNA transcribed from the DNA coding sequence (e.g., either pre- or post-modification).

The use of fragments and variants of the disclosed polynucleotides and polypeptides are also encompassed by the present invention. By "fragment" is intended a portion of the polynucleotide or polypeptide and include active fragments that retain the biological activity of the polypeptide or the ability to encode an active polypeptide fragment. Alternatively, fragments of a polynucleotide that are useful as hybridization probes or PCR primers need not retain this biological activity. Thus, fragments of a nucleotide sequence may range from at least about 20 nucleotides, about 50 nucleotides, about 100 nucleotides, about 500 nucleotides, about 1000 nucleotides, and up to the full-length polynucleotide.

Thus, a fragment of the polynucleotide may encode a polypeptide that is biologically active or it may be a fragment that can be used as a hybridization probe or PCR primer using methods disclosed below. A polynucleotide that encodes an active polypeptide can be prepared by isolating a portion of the polynucleotide (e.g., by recombinant expression in vitro) or chemically synthesizing the polynucleotide and assessing the activity of the encoded polypeptide. Polynucleotides that encode active fragments of the polypeptides of the invention have a nucleotide sequence comprising at least 10, 20, 30, 50, 100, 200, 500, or 1000 contiguous nucleotides of the sequences of the invention, or up to the number of nucleotides present in a polynucleotide that encodes a full-length polypeptide.

"Variants" is intended to mean substantially similar sequences. A variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide comprises a naturally occurring nucleotide sequence. Naturally occurring allelic variants such as these can be identified with the use of well-known molecular biology techniques, for example, with polymerase chain reaction (PCR) and hybridization techniques as outlined below. Variant polynucleotides also include synthetically derived polynucleotides, such as those generated, for example, by using site-directed mutagenesis (but which still retain the activity of the polynucleotides of the invention). Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

"Variant" polypeptide is intended to mean a polypeptide derived from the native polylpeptide by deletion (so-called truncation) of one or more amino acids at the N-terminal and/or C-terminal end of the native polypeptide; deletion and/or addition of one or more amino acids at one or more internal sites in the native polypeptide; or substitution of one or more amino acids at one or more sites in the native polypeptide. Variant polypeptides encompassed by the present invention are biologically active, that is they continue to possess the desired biological activity of the native polypeptide. Such variants may result from, for example, genetic polymorphism or from human manipulation. In general, biologically active variants of a native polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native polypeptide as determined by sequence alignment programs and parameters described elsewhere herein. A biologically active variant of a polypeptide of the invention may differ from that polypeptide by as few as 1-15 amino acid residues, as few as 1-10, such as 6-10, as few as 5, as few as 4, 3, 2, or even 1 amino acid residue.

The polynucleotides that encode the polypeptides useful in this invention can be used to isolate variants of the polynucleotide sequences from any organism. In this manner, methods such as PCR, hybridization, and the like can be used to identify such sequences based on their sequence homology to the sequences set forth herein. Sequences isolated based on their sequence identity to the entire polynucleotides sequences set forth herein or to variants and fragments thereof are useful for the present invention. In a PCR approach, oligonucleotide primers can be designed for use in PCR reactions to amplify corresponding polynucleotide sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire T3 polynucleotide disclosed herein, or one or more portions thereof, may be used as a probe capable of specifically hybridizing to corresponding pilus shaft-encoding polynucleotides and messenger RNAs. To achieve specific hybridization under a variety of conditions, such probes include sequences that are unique among pilus shaft-encoding polynucleotide sequences and are optimally at least about 10 nucleotides in length, and most optimally at least about 20 nucleotides in length. Such probes may be used to amplify corresponding pilus shaft-encoding polynucleotides from a chosen bacterium by PCR. This technique may be used to isolate additional coding sequences from a desired bacterium. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions, wherein a probe will hybridize to its target sequence to a detectably greater degree than to other sequences (e.g., at least 2-fold over background). Stringent conditions are sequence-dependent and will be different in different circumstances. Stringency conditions can be adjusted to allow the identification of 100% complementary sequences or sequences with lower degrees of similarity. Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The percent sequence identity between two sequences can be determined using alignment methods that are well known in the art, such as mathematical algorithms. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity, including, but not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10, which uses the algorithm of Needleman and Wunsch (1970) *J. Mol. Biol.* 48:443-453, using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. The default gap creation and extension penalty values can be used for sequence alignments.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The polynucleotides that are introduced into a Gram-positive bacterium can further comprise one or more regulatory sequences that are operably linked to the polynucleotide encoding the chimeric polypeptide that facilitate expression of the polynucleotide. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. See, for example, Goeddel (1990) in *Gene Expression Technology: Methods in Enzymology* 185 (Academic Press, San Diego, Calif.). Regulatory sequences may include promoters, translation leader sequences, introns, and polyadenylation recognition sequences. A polynucleotide comprising regulatory sequences operably linked to coding sequences can be referred to as expression cassettes.

Regulatory sequences are operably linked with a coding sequence to allow for expression of the polypeptide encoded by the coding sequence. "Operably linked" is intended to mean a functional linkage between two or more elements. For example, an operable linkage between a polynucleotide that encodes a polypeptide and a regulatory sequence (i.e., a promoter) is a functional link that allows for expression of the polypeptide. Operably linked elements may be contiguous or non-contiguous. Polynucleotides may be operably linked to regulatory sequences in sense or antisense orientation. When used to refer to the joining of two protein coding regions, by operably linked is intended that the coding regions are in the same reading frame.

The regulatory regions (i.e., promoters, transcriptional regulatory regions, and translational termination regions) and/or the coding polynucleotides may be native/analogous to the host cell or to each other. Alternatively, the regulatory regions and/or the coding polynucleotides may be heterologous to the host cell or to each other. As used herein, "heterologous" in reference to a sequence or a polypeptide is a sequence or polypeptide that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

In particular embodiments wherein the polynucleotide encoding the chimeric polypeptide comprises regulatory sequences, the polynucleotide can further comprise additional coding sequences. In some of these embodiments, the regulatory sequences can be operably linked to more than one coding sequence. For example, a single promoter can be operably linked to more than one coding sequence, wherein the coding sequences are co-transcribed from the single promoter into a single polycistronic transcript, which is separately translated into more than one polypeptide.

It will be appreciated by those skilled in the art that the design of the expression cassette can depend on such factors as the choice of the host cell to be transformed, the level of expression of the presently disclosed polynucleotides, and the like. Such expression cassettes typically include one or more appropriately positioned sites for restriction enzymes, to facilitate introduction of the nucleic acid into a vector.

It will further be appreciated that appropriate promoter and/or regulatory elements can readily be selected to allow expression of the presently disclosed polynucleotides in the cell of interest.

"Promoter" refers to a polynucleotide capable of controlling the expression of a polynucleotide. In general, the polynucleotide to be transcribed is located 3' to a promoter sequence. The promoter sequence may comprise proximal and more distal upstream elements; the latter elements often referred to as enhancers. Accordingly, an "enhancer" is a polynucleotide, which can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is recognized that since in most cases the exact boundaries of regulatory sequences have not been completely defined, polynucleotide fragments of different lengths may have identical promoter activity.

The promoters used in accordance with the present invention may be constitutive promoters or regulated promoters. Common examples of useful regulated promoters include those of the family derived from the nisin promoter (see, for example, U.S. Pat. No. 5,914,248 and Kleerebezem et al. (1997) *Appl Environ Microbiol* 63:4581-4584, each of which are herein incorporated by reference in its entirety); and the tetracycline-inducible and tetracycline-repressible promoters (see, for example, Gatz et al. (1991) *Mol. Gen. Genet.* 227:229-237, and U.S. Pat. Nos. 5,814,618 and 5,789,156, which are herein incorporated by reference). Regulated promoters utilize promoter regulatory proteins in order to control transcription of the gene of which the promoter is a part. Where a regulated promoter is used herein, corresponding promoter regulatory protein(s) will also be part of an expression system according to the present invention. Examples of promoter regulatory proteins include the NisR and NisK proteins for use with the nisA promoter. Many regulated-promoter/promoter-regulatory protein pairs are known in the art.

Promoter regulatory proteins interact with or are activated or repressed by an effector compound, i.e. a compound that reversibly or irreversibly associates with or activates or represses the regulatory protein so as to enable the protein to either release or bind to at least one DNA transcription regulatory region of the gene that is under the control of the promoter, thereby permitting or blocking the action of a transcriptase enzyme in initiating transcription of the gene. A non-limiting example of an effector compound is tetracycline or nisin for use with tetracycline-regulated promoter systems or nisin-regulated systems, respectively. Effector compounds are classified as either inducers or co-repressors, and these compounds include native effector compounds and gratuitous inducer compounds. Many regulated-promoter/ promoter-regulatory-protein/effector-compound systems are known in the art. Although an effector compound can be used throughout the cell culture or fermentation, in some embodiments in which a regulated promoter is used, after growth of a desired quantity or density of host cell biomass, an appropriate effector compound is added to the culture to directly or indirectly result in expression of the desired gene(s) encoding the protein or polypeptide of interest.

Other non-limiting examples of useful promoters for expression in Gram positive cells are the $P_{ami}$, $P_{spac}$, $P_{veg}$, and P23 promoters (see, for example Biswas et al. (2008) *Microbiology* 154:2275-2282, which is herein incorporated by reference in its entirety).

Other regulatory elements may be included in an expression cassette, including but not limited to, transcriptional enhancer sequences, translational enhancer sequenes, other promoters, activators, translational start and stop signals, transcription terminators, cistronic regulators, polycistronic regulators, signal sequences (e.g., Sec dependent signal sequences), or tag sequences, such as nucleotide sequence "tags" and "tag" polypeptide coding sequences, which facilitates identification of the polypeptide or cell expressing the polypeptide. A non-limiting example of a tag polypeptide is the hemagglutinin (HA) peptide.

Regulatory sequences found within expression cassettes can include a 3' non-coding region. The "3' non-coding region" or "terminator region" refers to DNA or RNA sequences located downstream of a coding sequence and may include polyadenylation recognition sequences and other sequences encoding regulatory signals capable of affecting mRNA processing or gene expression. The polyadenylation signal is usually characterized by effecting the addition of polyadenylic acid tracts to the 3' end of the mRNA precursor.

Proteins linked covalently to the Gram-positive cell wall are translocated across the membrane in a Sec-dependent process accompanied by cleavage of the signal peptide by a signal peptidase. Thus, in some embodiments, the expression cassette comprises a nucleotide sequence that encodes for an appropriate signal peptide that is inserted into the expression cassette in such a manner that it encodes a polypeptide of interest with the signal peptide fused to the amino terminal end of the polypeptide of interest. Sec-dependent signal sequences are known in the art and generally consist of a short (about 30 amino acids), mainly hydrophobic sequence comprising the following three domains: (i) a positively charged n-region with at least one arginine or lysine residue, (ii) a hydrophobic h-region and (iii) an uncharged but polar c-region. The cleavage site for the signal peptidase is located in the c-region. However, the degree of signal sequence conservation and length, as well as the cleavage site position, can vary between different proteins. The signal sequence aids protein export and is cleaved off by a periplasmic signal peptidase when the exported protein reaches the periplasm. In some embodiments, the signal peptide encoded by the expression cassette comprises the signal peptide derived from the *S. pyogenes* pilus tip polypeptide that is fused to the polypeptide of interest to be displayed on the pili tip (such as the signal peptide set forth in SEQ ID NO: 100 from the Cpa protein). In other embodiments, the signal peptide is derived from the polypeptide of interest. The signal peptide can also be heterologous to both the polypeptide of interest and the *S. pyogenes* pilus tip polypeptide (such as a consensus Sec-dependen signal sequence).

For suitable expression systems for prokaryotic cells, see Chapters 16 and 17 of Sambrook et al. (1989) *Molecular Cloning: A Laboratory Manual* (2d ed., Cold Spring Harbor Laboratory Press, Plainview, N.Y.), which are herein incorporated by reference. See also Goeddel (1990) in *Gene Expression Technology: Methods in Enzymology* 185 (Academic Press, San Diego, Calif.), which is herein incorporated by reference in its entirety.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (for example, PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); and Gill et al. (1988) *Nature* 334:721-724. Such disclosures are herein incorporated by reference.

The above list of selectable marker genes is not meant to be limiting as any selectable marker gene can be used in the present invention.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Such expression cassettes can be contained in a vector which allow for the introduction of the expression cassette into a cell. In specific embodiments, the vector allows for autonomous replication of the expression cassette in a cell or may be integrated into the genome of a cell. Such vectors are replicated along with the host genome. In general, expression vectors of utility in recombinant DNA techniques are often in the form of plasmids (vectors). However, the invention is intended to include such other forms of expression vectors, such as viral vectors.

According to the present invention, polynucleotides encoding the chimeric polypeptides are introduced into a cell. "Introducing" is intended to mean presenting to the cell the polynucleotide in such a manner that the sequence gains access to the interior of the cell. The methods of the invention do not depend on a particular method for introducing a sequence into a cell, only that the polynucleotide gains access to the interior of the cell. Methods for introducing polynucleotides into cells are known in the art including, but not limited to, stable transformation methods, transient transformation methods, and virus-mediated methods.

"Stable transformation" is intended to mean that the polynucleotide introduced into a cell integrates into the genome of the cell and is capable of being inherited by the progeny thereof "Transient transformation" is intended to mean that a polynucleotide is introduced into the cell and does not integrate into the genome of the cell.

Exemplary art-recognized techniques for introducing foreign polynucleotides into a host cell include calcium phosphate or calcium chloride co-precipitation, DEAE-dextran-mediated transfection, lipofection, particle gun, or electroporation and viral vectors. Suitable methods for transforming or transfecting host cells can be found in U.S. Pat. Nos. 5,049,386, 4,946,787; and U.S. Pat. No. 4,897,355, Sambrook et al. (1989) *Molecular Cloning: A Laboratory Manual* (2d ed., Cold Spring Harbor Laboratory Press, Plainview, N.Y.) and other standard molecular biology laboratory manuals. One of skill will recognize that depending on the method by which a polynucleotide is introduced into a cell, the polynucleotide can be stably incorporated into the genome of the cell, replicated on an autonomous vector or plasmid, or present transiently in the cell. In some embodiments, transient expression may be desired. In those cases, standard transient transformation techniques may be used. Such methods include, but are not limited to viral transformation methods, and microinjection of DNA or RNA, as well other methods well known in the art.

Host organisms containing the introduced polynucleotide are referred to as "transgenic" or "transformed" organisms. By "host cell" is meant a cell that contains an introduced polynucleotide construct and supports the replication and/or expression of the construct. The host cells of the present invention are Gram-positive bacteria.

The skilled artisan will recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events may have to be screened in order to obtain cells displaying the desired expression level and pattern. Such screening may be accomplished by PCR or Southern analysis of DNA to determine if the introduced polynucleotide is present in complete form, and then northern analysis or RT-PCR to determine if the expected RNA is indeed expressed.

According to the present invention, a polypeptide of interest is displayed on the surface of a bacterium as a chimeric polypeptide, wherein the polypeptide of interest is covalently attached directly or indirectly to a pilus tip protein. As used herein, a "chimeric polypeptide" or "fusion polypeptide" refers to a polypeptide comprising two polypeptides operably linked to one another, wherein the two polypeptides are not covalently bound to one another through peptide bonds in nature (without any human intervention). As described elsewhere herein, "operably linked" is intended to mean a functional linkage between two or more elements. For example, two polypeptides within a chimeric polypeptide are operably linked if the two polypeptides are fused to each other directly or indirectly through a peptide bond so that both polypeptides fulfill the proposed function attributed to each polypeptide. The chimeric polypeptides of the invention are created through the joining of the coding sequences for each polypeptide, wherein the two coding sequences are operably linked within the same reading frame to allow for the expression of the chimeric polypeptide. The polypeptide of interest could be fused indirectly to the pilus tip protein or active fragment or variant thereof, wherein additional amino acid residues can serve as a linker between the two polypeptides. The use of a linker sequence can increase the likelihood that the two polypeptides (polypeptide of interest and pilus tip protein) fold properly. The linker sequence can consist of 1 amino acid to about 100 amino acid residues or more.

The chimeric polypeptides of the invention comprise a heterologous polypeptide and a Gram-positive bacterial pilus tip polypeptide (or an active variant or fragment thereof). As used herein, a "pilus tip polypeptide" or "pilus tip protein" is a polypeptide that is present at the end of a bacterial pilus that extends out from the surface of the bacteria. The pilus tip polypeptide is distinct from the major pilin polypeptide that forms the shaft of the pilus (the pilus shaft polypeptide). While pilus shaft polypeptides can be localized at the tip of some pili, they are not considered pilus tip polypeptides, as they also comprise the major proteins found within the pilus shaft. In general, the pilus shaft polypeptide is the major pilin polypeptide and the pilus tip polypeptide is a minor pilin polypeptide within a given Gram-positive bacterium. In general, the major pilin protein is the T antigen that is often used for serological typing of *S. pyogenes* (Mora et al. (2005) *Proc Natl Acad Sci USA* 102:15641-15646; Schneewind et al. (1990) *J Bacteriol* 172:3310-3317).

In some embodiments, the pilus tip polypeptide comprises a pilus tip polypeptide from a *Streptococcus* bacterium. In some of these embodiments, the pilus tip polypeptide comprises a *Streptococcus pyogenes* pilus tip polypeptide. Data presented elsewhere herein demonstrate that the minor pilin protein Cpa from the M3 strain of *Streptococcus pyogenes* is present on the tip of pili. Cpa is a putative adhesin protein that is capable of binding to collagen. Thus, in some embodiments, the pilus tip polypeptide is an adhesin. An "adhesin" is a polypeptide that binds to an extracellular matrix protein, host cell surface protein, or other host cell-associated protein that facilitates bacterial-host cell interactions. An additional, non-limiting example of a *Streptococcus pyogenes* adhesin protein is the fibronectin-binding protein F1.

In general, the pilus tip protein of any given *Streptococcus pyogenes* strain is the protein encoded by the first non-regulatory gene present in the FTC region of the bacterial chromosome. In some embodiments, the *S. pyogenes* pilus tip polypeptide can be selected from the group consisting of Cpa, protein F1, OrfB, Spy0128, Spy0130, FctA, FctX, and FctB. In particular embodiments, the pilus tip polypeptide comprises a Cpa polypeptide (also known as Cpa49). In some of these embodiments, the pilus tip polypeptide comprises the Cpa polypeptide from the AM3 strain of *S. pyogenes* (sequence set forth in SEQ ID NO: 3), which is encoded by the nucleotide sequence set forth in SEQ ID NO: 4.

To determine if a given polypeptide functions as a pilus tip protein, one can use assays that are known in the art to localize a polypeptide to the tip of a pilus, including but not limited to assays presented elsewhere herein (see Experimental Example 1). Assays used to determine if a polypeptide is polymerized into a pilus structure, in general, involve extracting the cell wall fraction of bacteria (with mutanolysin with or without lysozyme), boiling the extract in SDS and separating the proteins using SDS-PAGE. Pilus proteins appear as high molecular weight ladders in immunoblots. The E. coli expression system and the mutational analysis of the pilus shaft polypeptide and pilus tip polypeptide used elsewhere herein can be used to determine if the polypeptide is indeed localized to the pilus tip. Other methods known in the art can be used to localize the pilus tip protein to the leading edge of pili, including but not limited to, visualization by fluorescence microscopy or negative staining (e.g., immunogold electron microscopy).

The chimeric polypeptide displayed on the tip of the Gram-positive pili can comprise an active variant or fragment of a pilus tip polypeptide. An active variant or fragment of a pilus tip polypeptide is a polypeptide that retains the ability to be localized to the tip of a bacterial pilus. In some embodiments, the active variant or fragment of the pilus tip polypeptide comprises the cell wall sorting signal (CWSS). In particular embodiments, the active fragment of the pilus tip polypeptide comprises at least one amino acid residue amino terminal to (i.e., preceding) the CWSS and the CWSS itself. In certain embodiments, the polypeptide fragment of the S. pyogenes pilus tip polypeptide comprises at least 2, at least 3, at least 5, at least 10, at least 20, at least 30, at least 40, at least 50, at least 100, at least 200, at least 300, at least 400, at least 500, at least 1000 amino acid residues amino terminal to the CWSS up to the full length pilus tip polypeptide sequence. In some embodiments, an active fragment comprises amino acids 594-744 of SEQ ID NO: 3 (this region is set forth in SEQ ID NO: 6). In some embodiments, the polypeptide of interest is fused (directly or indirectly) to an amino acid sequence that has at least 50%, at least 60%, at least 70%, at least 80%, at least 90%, at least 95%, at least 96%, at least 97%, at least 98%, at least 99%, or higher sequence identity to the amino acid sequence set forth in SEQ ID NO: 6.

In some embodiments, active variants of the pilus tip polypeptide have an amino acid sequence having at least 50%, at least 60%, at least 70%, at least 80%, at least 90%, at least 95%, at least 96%, at least 97%, at least 98%, at least 99%, or higher sequence identity to the amino acid sequence set forth in SEQ ID NO: 3. In certain embodiments, active variants of the pilus tip polypeptide are encoded by a nucleotide sequence having at least 50%, at least 60%, at least 70%, at least 80%, at least 90%, at least 95%, at least 96%, at least 97%, at least 98%, at least 99%, or higher sequence identity to the nucleotide sequence set forth in SEQ ID NO: 4.

The cell wall sorting signal is present in all Gram-positive bacterial surface displayed proteins and is comprised of the cell wall sorting signal (CWSS) motif, which is generally a five amino acid residue motif, a hydrophobic domain carboxyl to the CWSS motif, and a charged tail region carboxyl to the substantially hydrophobic domain. The CWSS motif is recognized and cleaved by the "housekeeping" sortase A, which is a membrane-associated transpeptidase. Canonical CWSS motifs generally comprise a LPXTG (SEQ ID NO: 1) amino acid sequence. The motif is generally cleaved at the threonine by the sortase to form an acyl-enzyme intermediate, wherein the carboxyl group of the threonine (T) of the CWSS is linked to a cysteine (C) residue of the transpeptidase. Subsequently, the threonine is transferred to an amino group of the peptidoglycan molecule within the peptide crossbridge of the growing cell wall, thereby incorporating the protein into the cell wall (for reviews see Marraffini, L. A. et al. (2006) Microbiol. Mol. Biol. Rev. 70:192-221; Scott, J. R. et al. (2006) Annu. Rev. Microbiol. 60:397-423). As used herein, a "cleaved CWSS motif" comprises the remains of a CWSS motif sequence following the cleavage of the motif by a sortase transpeptidase enzyme. A cleaved canonical CWSS motif, thus, has the sequence of LPXT.

The S. pyogenes pilus tip protein or variant or fragment thereof that is carboxy terminal to a polypeptide of interest displayed on the tip of a pilus on a Gram-positive bacterium comprises a cleaved cell wall sorting signal (CWSS) motif. In some embodiments, variants of the pilus tip protein have an amino acid sequence having at least 50%, at least 60%, at least 70%, at least 80%, at least 90%, at least 95%, at least 96%, at least 97%, at least 98%, at least 99%, or higher sequence identity to the amino acid sequence set forth in SEQ ID NO: 101. In other embodiments, the variant of the pilus tip protein comprising a cleaved CWSS motif has an amino acid sequence having at least 50%, at least 60%, at least 70%, at least 80%, at least 90%, at least 95%, at least 96%, at least 97%, at least 98%, at least 99%, or higher sequence identity to the amino acid sequence set forth in SEQ ID NO: 103. In certain embodiments, the pilus tip protein comprising a cleaved cell wall sorting signal motif has the sequence set forth in SEQ ID NO: 101. In other embodiments, the pilus tip protein comprising a cleaved cell wall sorting signal motif has the sequence set forth in SEQ ID NO: 103.

Polymerization of pilin proteins in Gram-positive bacteria requires a sortase family transpeptidase (pilin polymerase) and therefore is generally assumed to proceed by a process similar to that demonstrated for the Staphylococcus aureus housekeeping sortase (Ton-That, H. et al. (1999) Proc. Natl. Acad. Sci. 96:12424-9; Ton-That, H. (2004) Trends Microbiol. 12:228-34; for a review of sortases, see Marrafifini et al. (2006) Microbiol Mol Biol Rev 70:192-221, both of which are herein incorporated in their entireties). It is believed that the pilin polymerase catalyzes formation of a peptide bond between the threonine in the CWSS motif of one subunit and an ε-amino group of a lysine in the next subunit of the growing pilus chain.

Along with the five amino acid residue CWSS motif, the CWSS also comprises a carboxyl terminal substantially hydrophobic domain and a charged tail region. By "substantially hydrophobic" is intended a region of a polypeptide, wherein at least about 50%, at least 60%, at least 70%, at least 80%, at least 90%, at least 95%, at least 96%, at least 97%, at least 98%, at least 99%, or more of the amino acid residues making up the region are hydrophobic. In some embodiments, the hydrophobic region is at least about 20, at least 25, at least 30, at least 35, at least 40, at least 45, at least 50, at least 55, or at least 60 amino acid residues in length. In particular embodiments, the hydrophobic region is at least about 25 amino acid residues in length. In certain embodiments, the hydrophobic region comprises the sequence set forth in amino acids 714-738 of SEQ ID NO: 3.

The hydrophobic region of the CWSS is followed by a charged tail region. At least about 50%, at least 60%, at least 70%, at least 80%, at least 90%, at least 95%, at least 96%, at least 97%, at least 98%, at least 99%, or more of the amino acid residues making up the charged tail region have a positive or negative charge at physiological pH. In some embodiments, the charged tail region comprises about 5 to about 20 amino acid residues, including, but not limited to, 5, 6, 7, 8, 9, 10, 11, 12, 13, 14, 15, 16, 17, 18, 19, and 20. In certain embodiments, the charged tail region comprises the sequence RKGTKK (SEQ ID NO: 5), which corresponds to the extreme carboxy terminus of Cpa (set forth in SEQ ID NO: 3).

It was demonstrated elsewhere herein that the sortase C2 polypeptide is capable of polymerizing the major pilin T3 polypeptide and is required for the covalent attachment of the minor pilin Cpa to T3 polypeptides at the tip of pili. Thus, according to the presently disclosed methods and compositions, the Gram-positive bacteria useful for the display of polypeptides of interest express a tip sortase as well as a pilus shaft polypeptide. As used herein, a "tip sortase" is a sortase enzyme capable of covalently attaching a pilus tip polypeptide to the pilus shaft. The tip sortase can be from any organism. In some embodiments, a tip sortase comprises a sortase C enzyme. In particular embodiments, the tip sortase comprises a sortase C1 or sortase C2 enzyme. In some embodiments, the sortase C enzyme comprises a SrtC1 polypeptide, which is found in the M1 strains of *S. pyogenes* (see Barnett et al. (2004) *J Bacteriol* 186:5865-5875).

In other embodiments, the tip sortase comprises a sortase C2 enzyme, such as the sortase C2 enzyme encoded within the FCT-3 and FCT-4 chromosomal regions of *S. pyogenes* bacteria (including, but not limited to the FCT-3 or FCT-4 regions from M3, M5, M12, M18, and M49 strains of *S. pyogenes*; see Barnett et al. (2004) *J Bacteriol* 186:5865-5875).

In particular embodiments, the sortase C2 enzyme comprises the srtC2 from the AM3 strain of *S. pyogenes* (with the amino acid sequence set forth in SEQ ID NO: 7). In some embodiments, the tip sortase has an amino acid sequence having at least 50%, at least 60%, at least 70%, at least 80%, at least 90%, at least 95%, at least 96%, at least 96%, at least 97%, at least 98%, at least 99%, or more sequence identity to the sequence set forth in SEQ ID NO: 7. The AM3 sortase C2 polypeptide is encoded by the nucleotide sequence set forth in SEQ ID NO: 8. In some embodiments, the tip sortase is encoded by a nucleotide sequence having at least about 50%, at least 60%, at least 70%, at least 80%, at least 90%, at least 95%, at least 96%, at least 96%, at least 97%, at least 98%, at least 99%, or more sequence identity to the sequence set forth in SEQ ID NO: 8. Active variants of SEQ ID NO: 7 retain the ability to attach a pilus tip polypeptide to a pilus shaft. Suitable assays for determining if a given polypeptide exhibits this activity include any method known in the art or described elsewhere herein (see Experimental Example 1).

Previous results have demonstrated that the sortase C2 enzyme is capable of attaching the T3 shaft polypeptide of the pilus from the M3 strain of *S. pyogenes* to the cell wall through a non-canonical CWSS motif. The CWSS motif of the T3 polypeptide (also referred to as Orf100) comprises a QVPTG (set forth in SEQ ID NO: 9) amino acid sequence. Results presented elsewhere herein demonstrate this non-canonical CWSS motif is also utilized by SrtC2 to attach the T3 polypeptides to one another. Further presented herein are data that show the SrtC2 enzyme also catalyzes the covalent attachment of the Cpa minor pilin to the T3 protein. Similar to the T3 polypeptide, Cpa also comprises a non-canonical CWSS motif with the amino acid sequence of VPPTG (SEQ ID NO: 10). These data suggest sortase C2 polypeptides recognize and cleave non-canonical CWSS motifs. Thus, in some embodiments, both the major shaft polypeptide expressed by the Gram-positive bacterium and the pilus tip polypeptide (or active variant or fragment thereof) fused to the displayed heterologous polypeptide comprise a non-canonical CWSS motif. In particular embodiments, a tip sortase is one that is capable of covalently attaching a pilus tip polypeptide with a non-canonical CWSS motif to a growing pilin chain or polymerizing a pilus shaft polypeptide having a non-canonical CWSS motif. As used herein, a "non-canonical CWSS motif" is one wherein the sequence does not follow the consensus canonical CWSS motif of LPXTG (SEQ ID NO: 1), wherein X is any amino acid. In some embodiments, the non-canonical CWSS motif comprises a XXPTG (SEQ ID NO: 11) motif. In some of these embodiments, the first amino acid comprises a glutamine or a valine. In other embodiments, the second amino acid comprises a valine or a proline. In yet other embodiments, the first amino acid comprises a glutamine or a valine and the second amino acid comprises a valine or a proline. In certain embodiments, the non-canonical motif is one comprising a XXPTG motif (SEQ ID NO: 11), wherein the first amino acid is not a leucine residue. In other embodiments, the second amino acid residue is not a proline.

The Gram-positive bacteria of the invention comprise a major pilin that functions as the pilus shaft polypeptide. A "pilus shaft polypeptide" is a polypeptide that comprises the shaft of the pilus. In some embodiments, the pilus shaft polypeptide comprises at least about 50%, at least 60%, at least 70%, at least 80%, at least 90%, at least 95%, 96%, 97%, 98%, 99%, or higher of the polypeptides comprising a pilus. In some embodiments, the pilus shaft polypeptide comprises the major pilin protein. In general, the major pilin protein is the T antigen that is often used for serological typing of *S. pyogenes* (Mora et al. (2005) *Proc Natl Acad Sci USA* 102:15641-15646; Schneewind et al. (1990) *J Bacteriol* 172:3310-3317). In some embodiments, the pilus shaft polypeptide comprises a non-canonical CWSS motif within its cell wall sorting signal. In particular embodiments, the pilus shaft polypeptide comprises the T3 polypeptide. In some of these embodiments, the T3 polypeptide is from a M3 strain of *S. pyogenes*. In some of these embodiments, the T3 polypeptide comprises the T3 polypeptide from the AM3 strain of *S. pyogenes*, the amino acid sequence of which is set forth in SEQ ID NO: 12. In particular embodiments, the pilus shaft polypeptide has an amino acid sequence having at least about 50%, at least 60%, at least 70%, at least 80%, at least 90%, at least 95%, at least 96%, at least 97%, at least 98%, at least 99% or high sequence identity to the sequence set forth in SEQ ID NO: 12. The AM3 T3 polypeptide is encoded by the nucleotide sequence set forth in SEQ ID NO: 13. In some embodiments, the pilus shaft polypeptide is encoded by a nucleotide sequence having at least about 50%, at least 60%, at least 70%, at least 80%, at least 90%, at least 95%, at least 96%, at least 97%, at least 98%, at least 99% or higher sequence identity to the nucleotide sequence set forth in SEQ ID NO: 13. Pilus shaft polypeptides and active variants thereof retain the ability to polymerize into a pilus and to be covalently attached to a peptidoglycan molecule in the bacterial cell wall. Assays for detecting this activity include any method known in the art (see, for example, Barnett et al. (2004) J Bacteriol 186:5865-5875) and methods disclosed elsewhere herein (see Experimental Example 1). As disclosed elsewhere herein, the lysine residue at position 173 within the T3 protein is required for covalent attachment of T3 to Cpa. Specifically, the K173 residue is covalently attached to the threonine residue within the CWSS motif of Cpa. The lysine corresponding to amino acid residue 173 of T3 is conserved throughout the major pilin proteins found in at least the FCT-2, FCT-3, and FCT-4 chromosomal regions (see FIG. 5). Thus, in some embodiments, the pilus shaft polypeptide comprises a lysine residue within the major pilin protein in a similar region of the polypeptide as the K173 in T3 protein, which can be determined through alignment of the sequences using methods described elsewhere herein.

In some embodiments of the present invention, the tip sortase functions as a pilin polymerase, facilitating the polymerization of the pilin shaft polypeptides, in addition to its role in attaching the pilus tip polypeptide to the pilin shaft polypeptide. Additionally, in certain embodiments, the tip sortase has the ability to attach the pilus to peptidoglycans within the cell wall. In other embodiments, the tip sortase that attaches the pilus tip polypeptide to the pilus shaft polypeptide is distinct from the pilin polymerase that facilitates attachment of the pilus shaft polypeptides to one another or is distinct from the sortase enzyme that attaches the pilus to the cell wall (e.g., the housekeeping sortase A). In these embodiments, the transformed Gram-positive bacteria further express or comprise a pilin polymerase that can polymerize the pilin shaft polypeptide, a sortase that attaches the pilus to the cell wall (e.g., the housekeeping sortase A), or both.

Attachment of the T3 polypeptide and the Cpa polypeptide to the cell wall of M3 strains of S. pyogenes requires the SipA pilin chaperone polypeptide. As used herein, a pilin chaperone polypeptide is a polypeptide that is required for the stabilization of pilin proteins and that facilitates the polymerization and cell wall attachment of a pilus. Thus, in some embodiments, the Gram-positive bacteria further express a pilin chaperone polypeptide. In certain embodiments, the pilin chaperone polypeptide comprises a SipA polypeptide from an M3 strain of S. pyogenes (Zähner and Scott (2008) J Bacteriol 190:527-535). In some embodiments, the SipA polypeptide is from the AM3 strain of S. pyogenes, the amino acid sequence of which is set forth in SEQ ID NO: 14. In some of these embodiments, the pilin chaperone polypeptide has an amino acid sequence having at least about 50%, at least 60%, at least 70%, at least 80%, at least 90%, at least 95%, at least 96%, at least 97%, at least 98%, at least 99% or higher sequence identity to the sequence set forth in SEQ ID NO: 14. The AM3 SipA polypeptide is encoded by the nucleotide sequence set forth in SEQ ID NO: 15. In some embodiments, the pilin chaperone polypeptide is encoded by a nucleotide sequence having at least about 50%, at least 60%, at least 70%, at least 80%, at least 90%, at least 95%, at least 96%, at least 97%, at least 98%, at least 99% or higher sequence identity to the sequence set forth in SEQ ID NO: 15. A given polypeptide sequence (or a polypeptide encoded by any nucleotide sequence) can be assessed for its ability to function as a pilin chaperone using any method known in the art (see Zähner and Scott (2008) J Bacteriol 190:527-535), including those methods disclosed elsewhere herein (see Experimental Example 1).

In particular embodiments wherein Cpa or an active variant or fragment thereof serves as the pilus tip protein that is fused to the polypeptide of interest, the Gram positive bacterium further expresses or comprises the tip polymerase SrtC2, the T3 pilus shaft polypeptide, and the SipA2 chaperone protein. In some of these embodiments, the SrtC2 tip polymerase has the sequence set forth in SEQ ID NO: 7, the T3 pilus shaft polypeptide has the sequence set forth in SEQ ID NO: 12, and the SipA2 chaperone protein has the sequence set forth in SEQ ID NO: 14.

In some embodiments, at least one of the pilus shaft polypeptide, sortase C polypeptide, and pilin chaperone polypeptide are heterologous to the Gram-positive bacterium that is displaying a polypeptide of interest. In some embodiments, one or all of the polypeptides can be expressed within the bacteria through the introduction of an expression cassette that comprises a polynucleotide that comprises a nucleotide sequence that encodes for at least one of the three polypeptides. In some embodiments, the expression cassette that comprises the polynucleotide that encodes the chimeric polypeptide also comprises a coding sequence for at least one of a SrtC, pilus shaft, and SipA polypeptides. In other embodiments, the expression cassette that comprises a polynucleotide sequence that encodes at least one of the SrtC, pilus shaft, and SipA polypeptides is different from the expression cassette that comprises the polynucleotide that encodes the chimeric polypeptide. In yet other embodiments, each of the polypeptides is encoded by a coding sequence present on a distinct expression cassette.

The transformed Gram-positive bacterium displaying the polypeptide of interest can display more than one polypeptide of interest. In some of these embodiments, the Gram-positive bacterium comprises at least two groups of pili, wherein each group expresses a distinct polypeptide of interest. This can be due to the introduction of at least two distinct polynucleotides, each encoding for a distinct chimeric polypeptide. Alternatively, one polynucleotide can be introduced into the bacterium, wherein the polynucleotide comprises coding sequences for each of the polypeptides that are to be displayed on the surface of the bacterium. In these embodiments, the coding sequence for each chimeric polypeptide (the polypeptide of interest fused to a Gram positive bacterial pilus tip protein or an active variant or fragment thereof) can be operably linked to the same regulatory sequences (monocistronic) or to separate regulatory sequences (polycistronic).

According to the methods of the invention, following the introduction of the polynucleotide comprising an expression cassette encoding the chimeric polypeptide, the Gram-positive bacterium is grown under conditions that allow for the generation of the pilus. The growth conditions used for this step of the presently disclosed methods can be any growth condition known in the art for growth of the Gram-positive bacterium that is displaying the polypeptide of interest. In general, the bacteria can be grown in liquid or solid culture medium. Growth in liquid culture often is facilitated through aeration of the culture medium (e.g., through shaking of the container comprising the medium). In some embodiments, particularly those embodiments wherein the Gram-positive bacterium is a S. pyogenes bacterium, the bacterium is grown in Todd-Hewitt medium (such as the Todd-Hewitt medium that is commercially available from BD, Sparks, Md.). In some of these embodiments, growth supplements are added to the medium. A non-limiting example of a growth supplement is yeast extract. In some embodiments, Todd-Hewitt medium is supplemented with yeast extract at a 0.2% concentration. Another non-limiting example of a growth media for Gram positive bacteria, including L. lactis, is M17 media (such as the M17 media available from Oxoid Limited, Hampshire, UK). The M17 media can be supplemented with glucose (for example, at a concentration of 0.5%).

As used herein, a "polypeptide of interest" refers to any full-length, variant, or fragment of any naturally-occurring polypeptide from any organism (prokaryotic or eukaryotic) or a synthetically derived polypeptide that would find use in the display on the surface of a bacterium. In some embodiments, the polypeptide of interest that is displayed on the surface of the bacterium retains the activity (e.g., enzymatic activity) of the naturally occurring polypeptide or the same polypeptide that has not been fused to the pilus tip polypeptide. As non-limiting examples, the polypeptide can comprise an enzyme, an antigen, or a biosorbent. The polypeptide of interest may be native to the Gram-positive bacterium that is displaying the polypeptide of interest or the polypeptide of interest may be heterologous to the bacterium.

The compositions and methods of the invention can be used for any use known in the art for surface displayed polypeptides (see, for example, Hansson et al. (2001) *Combinatorial Chemistry & High Throughput Screening* 4:171-184; Wu et al. (2008) *Trends in Microbiology* 16:181-188; Wernerus and Stahl (2004) *Biotechnol. Appl. Biochem.* 40:209-228; Chen and Georgiou (2002) *Biotechnol Bioeng* 79:496-503; Lee et al. (2003) *Trends in Biotechnology* 21:45-52; Wernerus et al. (2002) *Journal of Biotechnology* 96:67-78, each of which are herein incorporated by reference). For example, the compositions and methods of the invention are useful in methods for inducing an immunological response in a subject, methods for screening for expression of a heterologous polypeptide, methods for removing a contaminant from a composition (e.g., soil, water), methods for producing ethanol, and methods for improving food and nutritional additives.

As used herein, an "antigen" comprises any polypeptide that can mount an immune response in a subject and is, thus, immunologically active. The present invention provides immunological compositions or vaccines comprising a Gram-positive bacterium displaying an antigen on the tip of a pilus, wherein the antigen is amino terminal to a *Streptococcus pyogenes* pilus tip protein or an active variant or fragment thereof, wherein said pilus tip protein or active variant or fragment thereof comprises a cleaved cell wall sorting signal (CWSS) motif.

The immunological compositions comprising the Gram-positive bacteria displaying an antigen can be used to prevent the development of a particular disease or unwanted condition through the administration of the compositions to a subject. As used herein, the term "prevent" refers to obtaining a desired pharmacologic and/or physiologic effect. Administration of the immunological composition might lead to complete or partial prevention of a particular infection or disease or sign or symptom thereof.

Methods for inducing an immunological response in a subject comprise administering to a subject a composition comprising a Gram-positive bacterium displaying an antigen on the tip of a pilus, wherein the antigen is amino terminal to a *Streptococcus pyogenes* pilus tip protein or an active variant or fragment thereof, wherein said active variant or fragment comprises a cleaved cell wall sorting signal (CWSS) motif.

When referring to the Gram-positive bacteria of the invention or compositions comprising the same, the term "administering," and derivations thereof, comprises any method that allows for the Gram-positive bacteria or compositions comprising the same to contact a cell within the subject to which the composition was administered.

By "subject" is intended an animal, including a mammal, such as a human, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use. In particular embodiments, the subject is a human.

A non-limiting example of an antigen that can be displayed on the tip of a Gram-positive bacterial pili includes domain 1' (residues 168-258) of the protective antigen of the anthrax toxin of *Bacillus anthraces* (the nucleotide and amino acid sequence of which is set forth in SEQ ID NO 91 and 92, respectively), which is the domain that remains at the N-terminus of the toxin following its proteolytic cleavage by proteases ubiquitously present in host tissue. This domain, called the "LEF domain", is involved in binding to the other subunits of the anthrax toxin, LF (lethal factor), and EF (edematous factor). This antigen is useful for methods involving the administration of the Gram-positive bacterium displaying such an antigen for the purposes of providing protection against an infection of *Bacillus anthracis*. Another domain of the anthrax toxin that can be used as an antigen for the purpose of stimulating an immunological response to a *Bacillus anthracis* bacteria is domain 4 (residues 596-735 of SEQ ID NO: 92), called "RBD", which is responsible for binding of the toxin to host cell receptors. The RBD and LEF domains are antigenic as DNA vaccines, have been inserted into the influenza virus fused within the hemagglutinin protein, and have been shown to provide passive protection against the toxin (Li et al (2005) *J Virol* 79:10003-10012).

Other examples of antigens that can be displayed on the pili tip of a Gram-positive bacterium according to the presently disclosed methods include a mutant nontoxic form of the heat labile toxin LT A or LT B proteins, and CooD, an ETEC adhesin, which are useful in providing protection against enterotoxigenic *Escherichia coli* (ETEC). In some embodiments, the mutant LT A protein comprises a triple LT mutant (R7K, S63K, V53E) in which three residues required for toxin activity have been changed in ways that don't alter the protein structure (Pizza et al (1994) J Exp Med 180: 2147-2153; the nucleotide and amino acid sequences of the LT A protein are set forth in SEQ ID NO: 95 and 96, respectively and the nucleotide and amino acid sequences of the LT B protein are set are set forth in SEQ ID NO: 93 and 94, respectively). In those embodiments, wheren the antigen comprises CooD, the cooD gene from a CS1 ETEC strain (the nucleotide and amino acid sequence of which is set forth in SEQ ID NO: 89 and 90, respectively) can be used and its chaperone gene cooB will also be introduced into the Gram-positive bacteria displaying the antigen (Voegele, Sakellaris & Scott (1997) *Proc Natl Acad Sci USA* 94:13257-13261).

Vaccine delivery or immunization via attenuated bacterial vector strains expressing distinct antigenic determinants against a wide variety of diseases is now commonly being developed. Recently, mucosal (for example nasal or oral) vaccination using such vectors has received a great deal of attention. For example, both systemic and mucosal antibody responses against an antigenic determinant of the hornet venom were detected in mice orally colonized with a genetically engineered human oral commensal *Streptococcus gordonii* expressing the antigenic determinant on its surface (Medaglini et al. (1995) *Proc Natl Acad Sci USA* 2:6868-6872). Also, a protective immune response was elicited by oral delivery of a recombinant bacterial vaccine wherein tetanus toxin fragment C was expressed constitutively in *Lactococcus lactis* (Robinson et al. (1997) *Nature Biotechnology* 15:653-657). Mucosal immunization as a means of inducing IgG and secretory IgA antibodies directed against specific pathogens of mucosal surfaces is considered an especially effective route of vaccination. In addition, the existence of a common mucosal immune system permits immunization on one specific mucosal surface to induce secretion of antigen-specific IgA and other specific immune responses at distant mucosal sites. Thus, in some of these embodiments, the Gram-positive bacteria that display an antigen comprise attenuated pathogenic bacteria.

An alternative approach avoids the use of attenuated bacterial strains that may become pathogenic themselves by using recombinant commensal bacteria as vaccine carriers, such as *Streptococcus* spp. and *Lactococcus* spp (see, for example, Buccato et al. (2006) *Journal of Infectious Diseases* 194:331-340). In some embodiments, the Gram-positive bacteria that display an antigen comprise live, non-pathogenic bacteria. Non-limiting examples of non-pathogenic Gram-positive bacteria useful for the development of vaccines include *Streptococcus* gordinii, *Staphylococcus* xylosus, and *Staphylococcus carnosus*. Non-pathogenic bacteria can include, but are not limited to food-grade bacteria. A non-limiting example of a food-grade bacterium is *Lactococcus lactis*. *Lactococcus lactis* is currently used as a probiotic and has been reported to have adjuvant properties. Although it can colonize the intestines temporarily, it is not normally found in the human microflora. Further, it is likely that a continuous cold chain would not be required for delivery of an *L. lactis* vaccine and it would be inexpensive to produce. See Raha et al. (2005) *Appl Microbiol Biotechnol* 68:75-81, which is herein incorporated in its entirety, for a review on the use of *L. lactis* as a vaccine vector)

The presently disclosed immunological compositions can be formulated for delivery, i.e., administering to the subject, by any available route including, but not limited to parenteral (e.g., intravenous), intradermal, subcutaneous, oral, nasal, bronchial, opthalmic, transdermal (topical), transmucosal, rectal, and vaginal routes. In some embodiments, the route of delivery is intravenous, parenteral, transmucosal, nasal, bronchial, vaginal, or oral.

The presently disclosed compositions also can include a Gram-positive bacterium with a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds also can be incorporated into the compositions.

As one of ordinary skill in the art would appreciate, a presently disclosed pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity, such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). The composition should be sterile and should be fluid to the extent that easy syringability exists. In some embodiments, the pharmaceutical compositions are stable under the conditions of manufacture and storage and should be preserved against the contaminating action of microorganisms, such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, isotonic agents, for example, sugars, polyalcohols, such as manitol or sorbitol, or sodium chloride are included in the formulation. Prolonged absorption of the injectable formulation can be brought about by including in the formulation an agent that delays absorption, for example, aluminum monostearate and gelatin.

Sterile injectable solutions can be prepared by incorporating the active compound (e.g., polynucleotide) in the required amount in an appropriate solvent with one or a combination of ingredients enumerated above, as required, followed by filtered sterilization. In certain embodiments, solutions for injection are free of endotoxin. Generally, dispersions are prepared by incorporating the active compound into a sterile vehicle which contains a basic dispersion medium and the required other ingredients from those enumerated above. In those embodiments in which sterile powders are used for the preparation of sterile injectable solutions, the solutions can be prepared by vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions also can be prepared using a fluid carrier for use as a mouthwash. Pharmaceutically compatible binding agents, and/or adjuvant materials can be included as part of the composition. The tablets, pills, capsules, troches, and the like can contain any of the following ingredients, or compounds of a similar nature: a binder, such as microcrystalline cellulose, gum tragacanth or gelatin; an excipient, such as starch or lactose, a disintegrating agent, such as alginic acid, Primogel, or corn starch; a lubricant, such as magnesium stearate or Sterotes; a glidant, such as colloidal silicon dioxide; a sweetening agent, such as sucrose or saccharin; or a flavoring agent, such as peppermint, methyl salicylate, or orange flavoring. Compositions for oral delivery can advantageously incorporate agents to improve stability within the gastrointestinal tract and/or to enhance absorption.

For administration by inhalation, the presently disclosed compositions can be delivered in the form of an aerosol spray from a pressured container or dispenser which contains a suitable propellant, e.g., a gas such as carbon dioxide, or a nebulizer. Liquid aerosols, dry powders, and the like, also can be used.

Systemic administration of the presently disclosed compositions also can be by transmucosal or transdermal means.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds also can be prepared in the form of suppositories (e.g., with conventional suppository bases such as cocoa butter and other glycerides) or retention enemas for rectal delivery.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical or cosmetic carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals. Guidance regarding dosing is provided elsewhere herein.

Depending on the route of administration, the agent may be coated in a material to protect it from the action of enzymes, acids and other natural conditions which may inactivate the agent. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

To administer an agent by other than parenteral administration, it may be necessary to coat the agent with, or co-administer the agent with, a material to prevent its inactivation. Enzyme inhibitors include pancreatic trypsin inhibitor, diisopropylfluorophosphate (DEP) and trasylol.

In some embodiments, the polypeptide of interest displayed on the tip of Gram positive bacterial pili comprises an enzyme. As used herein, an enzyme is any polypeptide that can catalyze a chemical reaction. Thus, the presently disclosed Gram-positive bacteria that display enzymes can be used in methods requiring whole cell biocatalysts. Enzymes useful for the presently disclosed methods and compositions include those enzymes that are capable of degrading organic matter, those that are involved in the production of biofuels, or those that find use in improving the nutritive quality of food products, such as probiotics.

For the production of ethanol, Gram positive bacterium expressing an enzyme at the pilus tip that catalyzes a step in the degradation of plant materials such as starch, cellulosic, lignocellulosic materials or the like can be added to the plant materials. Non-limiting examples of enzymes useful for this purpose include starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; and starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), β-glucosidase (EC 3.2.1.21), endo-1,4-β-glucanase (EC 3.2.1.4) and the like; c) endoglucanases such as endo-1,3-β-glucanase (EC 3.2.1.6); d) L-arabinases, such as endo-1,5-α-L-arabinase (EC 3.2.1.99), α-arabinosidases (EC 3.2.1.55) and the like; e) galactanases such as endo-1,44-β-D-galactanase (EC 3.2.1.89), endo-1,34-β-D-galactanase (EC 3.2.1.90), α-galactosidase (EC 3.2.1.22), β-galactosidase (EC 3.2.1.23) and the like; f) mannanases, such as endo-1,44-β-D-mannanase (EC 3.2.1.78), (3-mannosidase (EC 3.2.1.25), α-mannosidase (EC 3.2.1.24) and the like; g) xylanases, such as endo-1,4-β-xylanase (EC 3.2.1.8), β-D-xylosidase (EC 3.2.1.37), 1,3-β-D-xylanase, and the like; h) other enzymes such as α-L-fucosidase (EC 3.2.1.51), α-L-rhamnosidase (EC 3.2.1.40), levanase (EC 3.2.1.65), inulanase (EC 3.2.1.7) and the like, enzymes capable of degrading maltose maltotriose and α-dextrins obtained from the first degradation of starch, include maltases, α-dexitrinase, α-1,6-glucosidases, glucoamylases α-1,4-glucan glucohydrolases), and the like, and enzymes capable of modifying monosaccharides, such as glucose isomerase, invertase, and the like.

Methods for improving the nutritive quality of food products (e.g., probiotics) include, but are not limited to, the addition of food-grade Gram-positive bacterium displaying an enzyme that assists in digestion of certain food products (e.g., carbohydrates) to food products for animal consumption. Such supplemented food products are particularly useful for subjects that exhibit enzymatic deficiencies and are less able to digest particular food products. In specific embodiments of these methods, the Gram-positive bacteria comprise lactic acid bacteria, which are bacteria that are capable of converting sugars, including lactose and other carbohydrates, into lactic acid. Non-limiting examples of lactic acid bacteria include bacteria from the genera *Lactobacillus* or *Bifidobacterium*. Non-limiting examples of *Lactobacillus* species useful as probiotics include *L. rhamnosus*, *L. reuteri*, *L. casei*, *L. acidophilus*, *L. bulgaricus*, *L. plantarum*, *L. salivarius*, *L. johnsonii*, and *L. helveticus*. Non-limiting examples of *Bifidobacterium* include *B. lactis*, *B. infantis*, *B. longum*, *B. animalis*, and *B. bifidum*. The addition of lactic acid bacteria to food products is particularly useful for the administration of the food products to people with lactose intolerance. Bacterial strains useful for probiotics are known in the art (see, for example, Sanders (2007) *Functional foods & nutraceuticals*; June 2007: pp. 36-41, which is herein incorporated by reference in its entirety). Enzymes that are useful in improving the nutritive quality of food products (e.g., for human or other animals) are known in the art and can be expressed on the pili of Gram positive bacteria (e.g., *Lactobacillus*, *Bifidobacterium*) using the methods described herein. Non-limiting examples of such enzymes include lactase, hemi-cellulase, and phytase.

In other embodiments, the polypeptide of interest that is displayed on the Gram positive pili comprises a biosorbent. As used herein, a biosorbent comprises a polypeptide that specifically binds with a substantially high affinity to a particular molecule. Non-limiting examples of biosorbents include polypeptides with a cellulose-binding domain, or a metal-binding domain, such as a metallothionein or a phytochelatin.

Gram-positive bacteria displaying a biosorbent find use in bioremediation methods. Specifically, the presently disclosed subject matter provides for methods for removing a contaminant from a composition (e.g., soil, water), wherein the method comprises introducing to the composition a Gram-positive bacterium with a polypeptide of interest displayed on the tip of the pilus, wherein the polypeptide of interest comprises a biosorbent capable of specifically binding to the contaminant or an enzyme capable of degrading the contaminant.

As used herein, the term "contaminant" refers to any inorganic or organic molecule that is not desirable in a particular composition (e.g., soil, water). Non-limiting examples of contaminants include environmental chemicals, radioactive elements, bacteria or organisms, the byproduct of the growth of bacteria or organisms, decomposing material, or waste. In some embodiments, the composition comprising the contaminant is soil or water. In some of these embodiments, the contaminant comprises a heavy metal. In these embodiments, the polypeptide of interest comprises a biosorbent, wherein the biosorbent comprises a metal binding polypeptide that specifically binds to heavy metals. In some of these embodiments, the metal binding polypeptide comprises a metallothionein or a phytochelatin.

In other embodiments, the contaminant comprises an organic contaminant. In these embodiments, the heterologous polypeptide comprises an enzyme capable of degrading the organic contaminant. In some embodiments, the organic contaminant comprises an organophosphate. In some of these embodiments, the heterologous polypeptide comprises organophosphorous hydrolase (OPH).

As used herein, the term "removing" when referring to a contaminant means there is less than 99%, less than 98%, less than 97%, less than 96%, less than 95%, less than 90%, less than 80%, less than 70%, less than 60%, less than 50%, less than 40%, less than 30%, less than 20%, less than 10%, less than 5%, less than 1% or less of the contaminant remaining in the composition after the introduction of the bacterium displaying the biosorbent or degrading enzyme relative to the same composition prior to its introduction.

The presently disclosed Gram-positive bacteria also find use in diagnostic methods, wherein the Gram-positive bacteria display a detection reagent, which is a peptide (including, but not limited to, an antibody or a fragment thereof) capable of specifically detecting a disease-associated protein or ligand. In some of these embodiments, the displayed peptide further comprises a detectable label (e.g., a radiolabel, a fluorescent label). The Gram-positive bacteria displaying the detection reagent can be administered to a subject, followed by detection of the bacteria through the detectable label attached thereto. In some of these embodiments, the Gram-positive bacteria that is displaying the detection reagent comprise attenuated pathogenic bacteria or non-pathogenic commensal bacteria.

The following examples are offered by way of illustration and not by way of limitation.

EXPERIMENTAL

Example 1. Cpa Pilins are Present on the Tip of Group A *Streptococcus* Pili To study the covalent linkage of major and minor pilin subunits catalyzed by the pilin polymerase SrtC2, an expression system in *Escherichia coli* has been established (Zähner, D. et al. (2008) *J. Bacteriol.* 190:527-35). In this system, the only GAS genes present are those encoding SrtC2, the pilins T3 and Cpa, and the chaperone, SipA2. Because complete pili are not synthesized in *E. coli*, a large fraction of the total pilin protein consists of the low molecular weight pilin polymers. This genetic approach has allowed the definition of the pilin residues required for covalent linkage of these subunits.

In this work, the linkage of the minor pilin protein Cpa to the backbone protein of T3 pili of GAS was investigated. The results indicate that the noncanonical CWSS motif in Cpa is required for its attachment to the T3 protein by SrtC2. Evidence is also provided that addition of Cpa to T3 requires the same lysine residue in T3 that is needed for polymerization of T3 subunits. This implies that addition of Cpa to a T3 subunit leaves only the C-terminus of this T3 subunit available for addition of another subunit. Therefore, the results strongly suggest that Cpa is located exclusively at the tip of the T3 pilus, and, based on this, a model for biogenesis of these pili has been suggested.

Cpa is not Linked to the N-Terminus of T3

In previous analyses of T3 pilus polymerization in *E. coli*, a presumptive T3-Cpa heterodimer using an HA-tagged derivative of Cpa was identified (Zähner, D. et al. (2008) J. Bacteriol. 190:527-35). This protein was encoded on pJRS1326, which also encodes SipA2, T3 and SrtC2, all derived from the M3 GAS strain AM3 (see FIG. 1). To identify the Cpa(HA) monomer, pJRS1325, a plasmid derived from pJRS1326 by deletion of srtC2 was used. Monomeric Cpa(HA) appeared as a band of approximately 75 kDa on western blots of whole cell lysates of TOP10/pJRS1325 boiled in SDS (Zähner, D. et al. (2008) *J. Bacteriol.* 190:527-35 and FIG. 2A lane 2). In the presence of SrtC2, a second strong band that reacted with both anti-T3 and anti-HA antisera was visible (Zähner, D. et al. (2008) *J. Bacteriol.* 190:527-35 and FIGS. 2A and B lanes 3). The molecular mass difference between this approximately 105 kDa band and the monomeric Cpa(HA) band is approximately that of the mature T3 protein (about 32 kDa). To confirm that the 105 kDa band is a heterodimer of Cpa(HA) covalently bound to T3, a whole cell lysate of *E. coli* TOP10/pJRS1326 was subjected to immunoprecipitation using an anti HA-antibody. The immunoprecipitate was boiled in SDS to dissociate noncovalent protein interactions and separated by SDS-PAGE. The 105 kDa band (FIG. 2B, lane 3) was recovered from a SyproRuby-stained SDS gel, digested with trypsin and subjected to mass spectrometry (MS) for peptide identification. Both T3 and Cpa(HA) peptides were present in the immunoprecipitated sample (see Table 1).

TABLE 1

T3/Cpa peptides identified by mass-spectrometry [a]

| | | | CpaHA | | |
|---|---|---|---|---|---|
| Start[b] | End[b] | Before[c] | Sequence | SEQ ID NO: | After[c] |
| 46 | 54 | G[d] | AEEQSVPNK | 47 | Q |
| 72 | 80 | K | GYPDYSPLK | 48 | T |
| 87 | 93 | K | VNLDGSK | 49 | E |
| 120 | 130 | K | KLEGTNENFIK | 50 | L |
| 121 | 130 | K | LEGTNENFIK | 51 | L |
| 137 | 148 | R | IEDGQLQQNILR | 52 | I |
| 149 | 158 | R | ILYNGYPNDR | 53 | N |
| 164 | 176 | K | GIDPLNAILVTQN | 54 | A |

TABLE 1-continued

T3/Cpa peptides identified by mass-spectrometry [a]

| Start | End | Before | Sequence | SEQ ID NO: | After |
|---|---|---|---|---|---|
| 193 | 202 | K | AFQQEETDLK | 55 | L |
| 236 | 245 | Y | QLSIFQSSDK | 56 | T |
| 271 | 282 | K | YPYDVPDYATEK[e] | 57 | T |
| 289 | 297 | R | KYAEGDYSK | 58 | L |
| 290 | 297 | K | YAEGDYSK | 59 | L |
| 298 | 305 | K | LLEGATLK | 60 | L |
| 306 | 317 | K | LAQIEGSGFQEK | 61 | I |
| 318 | 323 | K | IFDSNK | 62 | S |
| 347 | 355 | Y | GVATPITFK | 63 | V |
| 365 | 376 | K | NKEGQFVENQNK | 64 | E |
| 367 | 376 | K | EGQFVENQNK | 65 | E |
| 450 | 460 | K | YTHVSGYDLYK | 66 | Y |
| 467 | 475 | R | DKDADFFLK | 67 | H |
| 469 | 475 | K | DADFFLK | 68 | H |
| 494 | 501 | K | TLTEAQFR | 69 | A |
| 528 | 534 | K | GYHGFDK | 70 | L |
| 594 | 603 | K | QAPIIPITHK | 71 | L |
| 609 | 618 | K | TVTGTIADKK | 72 | K |

T3

| Start | End | Before | Sequence | SEQ ID NO: | After |
|---|---|---|---|---|---|
| 29 | 38 | A[d] | ETAGVSENAK | 73 | L |
| 76 | 86 | K | DGLEIKPGIVN | 74 | G |
| 107 | 114 | K | STEFDFSK | 75 | V |
| 115 | 124 | K | VVFPGIGVYR | 76 | Y |
| 125 | 130 | R | YTVSEK | 77 | Q |
| 131 | 142 | K | QGDVEGITYDTK | 78 | K |
| 144 | 153 | W | TVDVYVGNK | 79 | E |
| 154 | 161 | K | EGGGFEPK | 80 | F |
| 191/296 | 202/308 | K/K | KNVSGNTGELQK/ TDESADEIVVTNK[f] | 81/82 | E/R |
| 218 | 226 | K | KDQIVSLQK | 83 | G |
| 219 | 226 | K | DQIVSLQK | 84 | G |
| 243 | 253 | K | LKNGESIQLDK | 85 | L |
| 245 | 253 | K | NGESIQLDK | 86 | L |
| 254 | 261 | K | LPVGITYK | 87 | V |
| 262 | 273 | K | VNEMEANKDGYK | 88 | T |

[a] Mass spectrometry performed on trypsin-digested band isolated from SDS-PAGE (105 kDa)
[b] numbering refers to the position in the sequence of the preprotein
[c] residue before/after the peptide cleavage site
[d] residue preceding the predicted signal peptide cleavage site in the preprotein
[e] HA-tag sequence indicated in bold letters
[f] peptides linked by intramolecular isopeptide bond; residues predicted to form bond are underlined.

Since the sample was boiled prior to separation by SDS-PAGE, it is concluded that the 105 kDa band corresponds to a covalently linked T3-Cpa heterodimer produced in E. coli in the presence of SrtC2.

Because a sortase forms an amide bond between the carboxyl group at the C terminus of one protein and an amino group of a second protein, it seemed possible that the Cpa protein was attached at the α-amino group of the distal T3 subunit in the pilus. T3 is synthesized as a preprotein that is predicted to be cleaved by the signal peptidase between alanine 28 and glutamate 29 (Zähner, D. et al. (2008) J. Bacteriol. 190:527-35). Consistent with this, the peptide representing the N-terminus of the mature T3 protein (E29-K38) was recovered by MS, while the first 28 residues of the preprotein of T3 were not among the peptides seen (FIG. 2C). Since trypsin is not expected to cleave between A28 and E29, recovery of peptide E29-K38 indicates that cleavage occurred in E. coli, and not during MS sample preparation. Therefore, recovery of the N-terminal peptide of T3 from the Cpa-T3 heterodimer demonstrates that the α-amino group at the T3 N-terminus is not bound to Cpa(HA).

The VPPTG Motif in the CWSS of Cpa is Required for Linkage of Cpa to T3

Because covalent linkage of Cpa to T3 requires the sortase family enzyme SrtC2, the motif at the start of the CWSS of Cpa was expected to be required for this reaction. However, this motif, VPPTG, differs from the canonical LPXTG motif found in substrates of the housekeeping sortase SrtA, like the M protein. It also differs from the CWSS motif in T3 (QVPTG), which is required for its polymerization by SrtC2 (Barnett, T. C. et al. (2004) J. Bacteriol. 186:5865-75). Therefore, studies were initiated to establish whether the VPPTG motif in the CWSS of Cpa is essential for linkage of Cpa to T3. LPSTG was substituted for the VPPTG motif of Cpa to test the importance of this motif in formation of the Cpa-T3 heterodimer.

Figure 1:
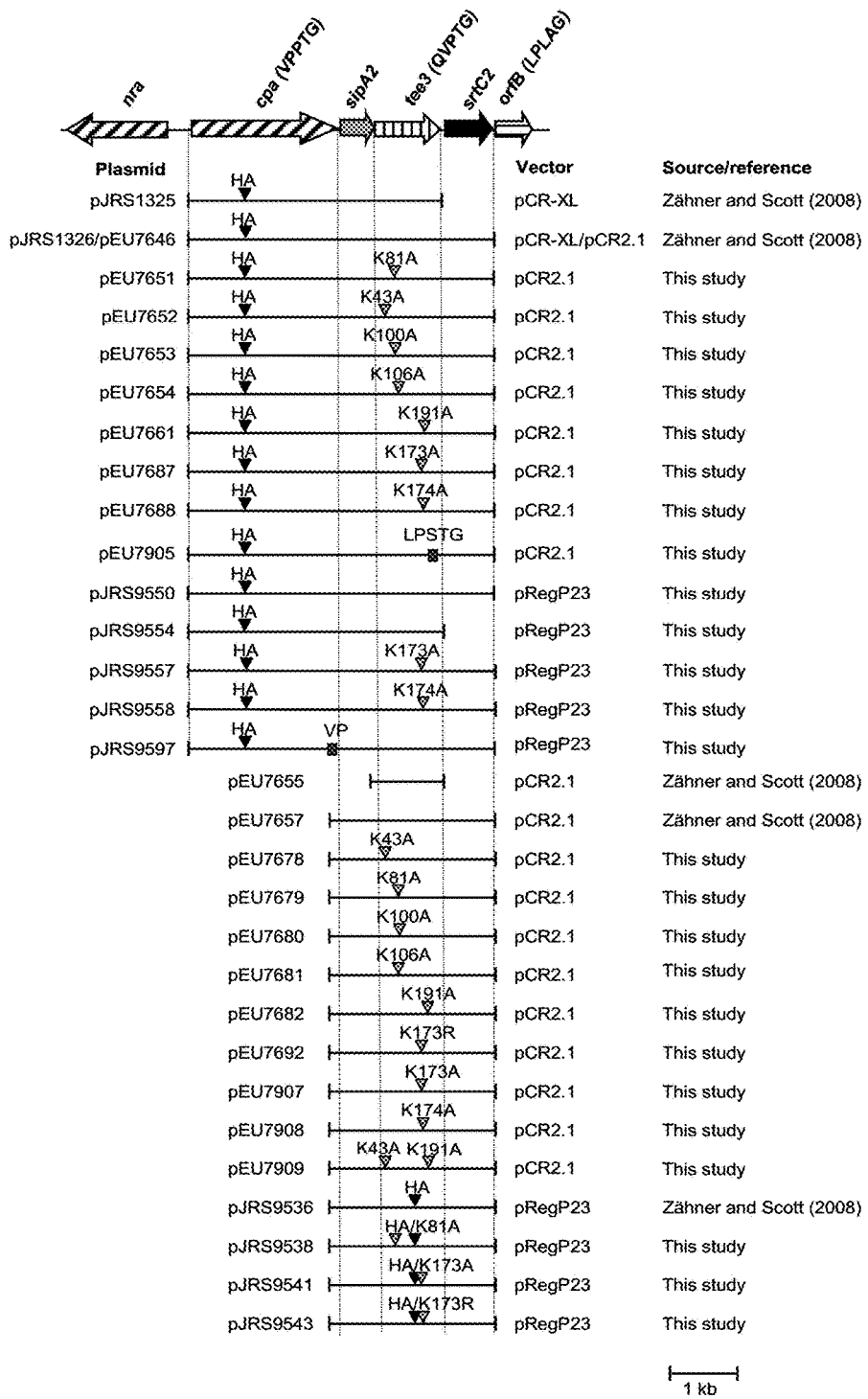
FIG. 1 depicts the FCT region of serotype M3 Group A *Streptococcus* strain M3 and derived constructs. The positions of HA tags and mutations introduced by site-specific mutagenesis are indicated by arrowheads. Vectors pCR2.1 and pCR-XL are *E. coli* cloning vectors (Invitrogen), and pRegP23 (Barnett et al. (2007) J Bacteriol 189:1866-1873), is a Gram-positive-*E. coli* shuttle vector. Zähner and Scott (2008) refers to Zähner and Scott (2008) *J Bacteriol* 190: 527-535, which is herein incorporated by reference in its entirety.
Figure 3A:
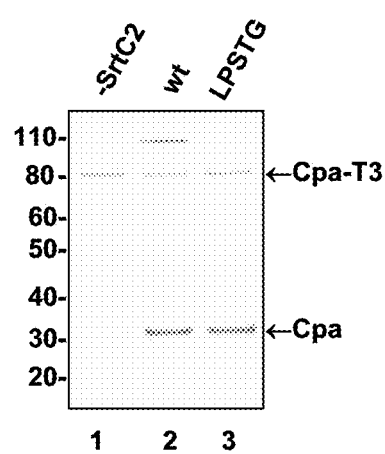
FIGS. 3A-3D demonstrate the effect of mutations in the CWSS motif of Cpa(HA) (FIGS. 3A and 3B) and of T3 (FIGS. 3C and 3D) on formation of the Cpa(HA)-T3 heterodimer in *E. coli*.
Figure 3B:
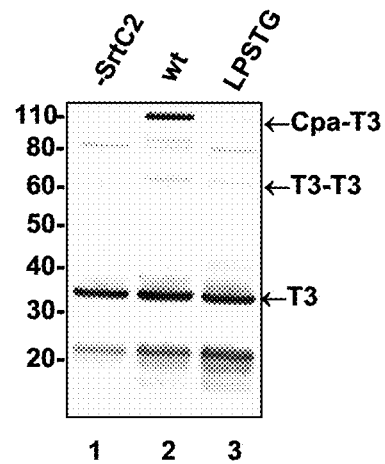

The HA-tagged derivative of Cpa was used in the assay that had been established in E. coli (Zähner, D. et al. (2008) J. Bacteriol. 190:527-35) to investigate this reaction. The desired motif replacement was constructed by site-directed mutagenesis of pEU7646 (FIG. 1). DNA sequencing was used to confirm the presence of the mutation in the resulting plasmid, pEU7904. The formation of the T3-Cpa(HA) heterodimer was examined, as well as the T3-T3 homodimer, by analysis of extracts of E. coli strains that had been boiled in SDS to disrupt non-covalent bonds. TOP10/pJRS1325, which lacks srtC2, was used to facilitate identification of the monomeric form of Cpa (FIG. 3A lane 1) and T3 (FIG. 3B lane 1). As expected, in extracts of strain TOP10/pEU7646, which encodes Cpa(HA) with the wild type CWSS, western blot analysis using an anti-HA antibody showed bands corresponding to the sizes for both the Cpa(HA) monomer (75 kDa) and the Cpa(HA)-T3 heterodimer (105 kDa) (FIG. 3A lane 2). However, no Cpa(HA)-T3 heterodimer was detected in extracts of the strain in which LPSTG replaced the VPPTG motif of the Cpa CWSS (TOP10/pEU7904; FIG. 3A lane 3). Instead, only the Cpa(HA) monomer and its characteristic degradation product, migrating at about 32 kDa, were present. To verify that the absence of the Cpa (HA)-T3 dimer was due to the introduction of the mutation in the Cpa(HA) CWSS motif, and not to an undetected second mutation that might affect the function of SipA2 or SrtC2, the same cell lysates were analyzed by western blot using anti-T3 antiserum (FIG. 3B). In both TOP10/pEU7646 and TOP10/pEU7904 (FIG. 3B lanes 2 and 3), T3 dimers were present, while they were absent from the strain lacking SrtC2 (FIG. 3B lane 1). This indicates that in both plasmids, the genes required for pilus formation functioned normally. The presence of polymerized forms of T3, combined with the absence of the T3-Cpa(HA) dimer in strain TOP10/pEU7904, demonstrate that the VPPTG motif in the CWSS of Cpa is required for linkage of Cpa to T3.

In addition to replacing the VPPTG motif of Cpa with the LPSTG sequence, the VPPTG sequence of the pJRS9550 plasmid was mutated to delete the "PTG" residues of the motif, leaving just "VP" (pJRS9597; FIG. 1). This plasmid was transformed into the heterologous serotype M6 GAS strain JRS4, which lacks the FCT-3 region containing the genes required for T3 pilus production and thus does not express T3 pili (see FIG. 10). A vector control, pJRS9545 (derived from pJRS9508), which consists of the pReg696 backbone and the P23 promoter, was transformed into JRS4 as a negative control. Cell wall fractions of this strain and strains JRS4/pJRS9550 (wt), JRS4/pJRS9554 (−SrtC2), and JRS4/pJRS9597 (VP) that had been boiled in SDS to dissociate noncovalent bonds were examined for formation of the Cpa(HA)-T3 heterodimer and incorporation of Cpa(HA) into HMW T3 polymers using an anti-HA antibody (FIG.

4A, lanes 1-4). Although the high molecular weight (HMW) banding pattern characteristic of pili on Gram-positive bateria (Mora et al. (2005) *Proc Natl Acad Sci USA* 102:15641-15646; Zähner and Scott (2008) *J Bacteriol* 190:527-535) was detected in cell wall extracts of JRS4/pJRS9550, the positive control, no pilus bands were visible in extracts of JRS4/pJRS9597 (the VP mutant) or of the SrtC2-control JRS4/pJRS9554. To be sure that SipA2 and SrtC2 remained functional in the mutant, the production of pili in cell wall fractions was also examined using anti-T3 (FIG. 4 B). The presence of high molecular weight (HMW) forms of T3 in the mutant extract indicated that lack of incorporation of Cpa into pili in JRS4/pJRS9597 is not due to a defect in polymerization of T3. As expected, HMW forms of T3 were present in cell wall extracts of JRS4/pJRS9550 (positive control) but not in those of its SrtC2-derivitive.

The absence of HMW polymers containing Cpa(HA) in cell wall extracts of the mutant might result either from lack of polymerization or from lack of covalent attachment of the pili to the cell wall. If the latter were correct, pilus polymers should be present in the culture supernatant. Therefore, concentrated supernatants were analyzed for the presence of HMW forms containing Cpa(HA) and polymerized T3 (FIG. 4 A, lanes 5-8 and data not shown). As expected, pili containing T3 were present in the concentrated supernatant and Cpa-containing pili were present in the supernatant from the positive control strain. However, Cpa(HA) was not present in HMW pilus forms in the supernatant of the VP mutant. The absence of incorporation of Cpa into the pili when the VPPTG motif is partially deleted indicated that the VPPTG motif at the start of the CWSS of Cpa is required for addition of Cpa to T3 pili.

Figure 3C:
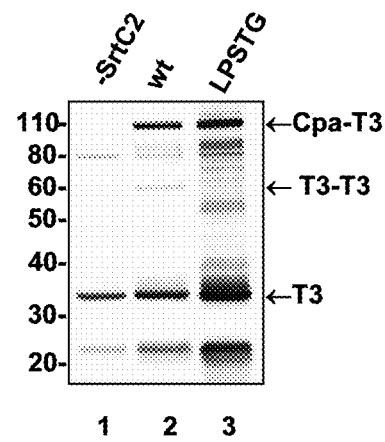
Figure 3D:
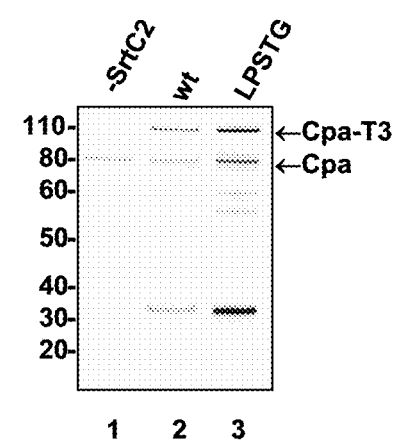

The QVPTG Motif in the T3 CWSS is not Necessary for Formation of the T3-Cpa Heterodimer Previously, it was shown that the QVPTG motif (SEQ ID NO: 9) in the CWSS of T3 is required for polymerization of T3 by SrtC2 (Barnett, T. C. et al. (2004) *J. Bacteriol.* 186:5865-75). To determine whether this motif is also needed for the formation of the Cpa(HA)-T3 heterodimer, it was replaced in pEU7646 with the canonical LPSTG motif (SEQ ID NO: 2; FIG. 1: pEU7905). Whole cell lysates of *E. coli* TOP10/pEU7905 were examined by western blots using anti-T3 antiserum and anti-HA antibody (FIGS. 3 C and D). As described above for the Cpa CWSS motif replacement experiments, TOP10/pJRS1325, which lacks srtC2, was used to identify the monomeric forms of T3 (FIG. 3C lane 1) and Cpa (FIG. 3D lane 1). Whole cell lysates of the control strain TOP10/pEU7646, which encodes T3 with the wild type CWSS, showed bands corresponding to the T3 monomer, the T3 dimer, and the T3-Cpa(HA) heterodimer (FIG. 3C lane 2) as well as the Cpa(HA) monomer and the Cpa(HA)-T3 heterodimer (FIG. 3D, lane 2). As previously found (Barnett, T. C. et al. (2004) *J. Bacteriol.* 186:5865-75), replacement of the native CWSS motif in T3 by LPSTG (in TOP10/pEU7905) prevented formation of multimers of T3, although the T3 monomer was still present (FIG. 3C lane 3). Most importantly, the T3-Cpa(HA) heterodimer was also visible in lysates of this strain (FIGS. 3C and D lanes 3). Thus, although the T3 CWSS motif is necessary for the polymerization of T3, it is not required for the formation of the T3-Cpa(HA) heterodimer.

Lysine Residues Forming Putative Intramolecular Bonds in T3 are not Required for its Polymerization To identify lysine residues in the T3 protein that might be involved in pilus formation, available sequences of the predicted pilus backbone proteins of the FCT-2, FCT-3 and FCT-4 regions of different GAS strains were compared (FIG. 5). Sequence alignment revealed 6 fully conserved lysine residues that correspond to K43, K81, K100, K106, K173, and K191 in the T3 protein. Using pEU7657 (FIG. 1), which expresses T3, SrtC2 and the chaperone-like protein SipA2 (Zähner, D. et al. (2008) *J. Bacteriol.* 190:527-35) as a template, each of these lysines were replaced with alanine and analyzed polymerization of T3 for each mutant in extracts of *E. coli*.

T3 dimers, and usually trimers, were visible on western blots of the cell extracts of the mutants with K to A corresponding to K43, K81, K100, K106, and K191 developed with anti-T3 antiserum (FIG. 6A). Surprisingly, the monomeric and polymeric forms of T3 mutant proteins K43A and K191A migrated with an increased apparent molecular mass relative to the wild type T3 protein (FIG. 6A, lanes 3 and 7). The homologs of K43 and K191 in T1, the homolog of T3 in the FCT-2 region, (FIG. 5), have been shown to be involved in intramolecular bonds (Kang et al. (2007) Science 318:1625-1628). Therefore, these two lysine residues are predicted to participate in intramolecular isopeptide bonds in T3. In support of this, the trypsin fragments of the Cpa(HA)-T3 heterodimer identified by MS analysis included one containing two T3 peptides linked by an isopeptide bond between K191 and N307 (Table 1).

The formation of these intramolecular bonds would be prevented by substituting alanine for the glutamate residue catalyzing formation of this bond (Kang et al. (2007) Science 318:1625-1628) or the lysine residue participating in the bond. Thus, it seems likely that the altered running behavior of the mutant proteins is a result of lack of formation of the intramolecular bonds. In agreement with this, the double mutant K43A,K191A protein migrates even more slowly than either single mutant protein (FIG. 6B). However, for both single mutants and for the double mutant, dimers of T3 protein were present and trimers were also visible on some gels (FIGS. 6A and 6B and data not shown). This indicates that if these lysine residues are essential for intramolecular bond formation, they are not a requirement for polymerization of T3.

Lysine Residue 173 of T3 is Required for T3 Polymerization

Multimeric forms of T3 were present for all mutants except one: K173A (FIG. 6C). In the K173A mutant (FIG. 6C, lane 3), the presence of monomeric T3, which has an apparent molecular mass of 32 kDa when analyzed by SDS PAGE, indicates that the mutant protein is expressed and is stable in this strain. Because it seemed possible that the charge on the lysine was the reason it was required for T3 polymerization, a second mutant in which K173 was replaced with arginine (R) was constructed (FIG. 1: pEU7692). Extracts of the *E. coli* strain containing this mutation also showed only T3 monomers (FIG. 6C, lane 4), indicating the importance of the lysine group for polymerization of the T3 pilin. As a control, the adjacent lysine, K174, was also replaced with A (FIG. 1: pEU7908). As expected, this had no visible effect on T3 polymerization (FIG. 6C, lane 5). This demonstration that K173 is essential for T3 polymerization is consistent with the recent X-ray crystallographic and MS analysis of the M1 major pilin (Kang et al. (2007) Science 318:1625-1628; see FIG. 5).

The role of K173 in T3 pilus formation was also examined in GAS. Previous studies (Zähner, D. et al. (2008) *J. Bacteriol.* 190:527-35) of T3 polymerization in GAS utilized pJRS9536 (FIG. 1), which contains the same DNA fragment from the GAS serotype M3 strain AM3 as used above in *E. coli* (plasmid pEU7657), except that an HA tag was added to the T3 protein (Barnett, T. C. et al. (2004) *J. Bacteriol.* 186:5865-75). This plasmid and its derivatives were analyzed in the heterologous serotype M6 GAS strain JRS4, which lacks the FCT-3 region containing the genes required for T3 pilus production. The high molecular weight (HMW) banding pattern, which is characteristic of pili on Gram-positive bacteria (Mora, M. et al. (2005) *Proc. Natl. Acad. Sci.* 102:15641-6; Zähner, D. et al. (2008) *J. Bacteriol.* 190:527-35) was detected with anti-HA antibody in western blots of cell wall extracts that had been boiled in SDS to dissociate noncovalent bonds. Plasmid pJRS9536 was used as a template for site-directed mutagenesis to introduce the mutations K173A and K173R in T3(HA), resulting in plasmids pJRS9541 and pJRS9543, respectively (FIG. 1). As a control, a K81A mutation was introduced into T3(HA) in plasmid pJRS9536 because this residue did not affect pilus formation in *E. coli* (FIG. 6A). This mutation had no effect on T3 polymerization in GAS as expected, although the total amount of all forms of T3 in GAS was reduced in this mutant relative to its wild type parent (FIG. 7, lane 4 vs 1). In GAS, replacing K173 with either A or R resulted in a loss of HMW T3(HA) polymers, while the monomer remained plentiful (FIG. 7, lanes 2 and 3 vs. lane 1), which is in agreement with the results in *E. coli*. The weak protein band that migrated with an apparent mass of about 65 kDa, consistent with the expected molecular weight of a T3(HA) dimer, does not appear to be a precursor to pilus formation since no higher molecular weight bands were visible. All four cell wall extracts also contained degradation products of approximately 20 kDa (FIG. 7, lanes 1-4).

The absence of HMW T3 polymers in cell wall extracts of the K173A mutant might result either from lack of polymerization or from lack of covalent attachment to the cell wall. If the latter were correct, pilus polymers should be present in the culture supernatant. To determine whether the T3(HA) monomer and/or its polymers are released into the culture medium, concentrated supernatants were analyzed for the presence of T3(HA). The supernatant from GAS strain JRS4/pJRS9536, which expresses the HA-tagged T3 protein along with the rest of the genes needed for pilus synthesis, showed a HMW banding pattern similar to that seen with the cell wall extract from this strain (FIG. 7, lanes 1 and 5). The culture supernatant of the K81A mutant (JRS4/pJRS9538) showed a weak, but discernable, HMW pattern, indicating that polymerization of the T3 protein occurred (FIG. 7, lane 8), although there was less total T3(HA) relative to the amount released from the wild type parent (pJRS9536). In contrast, no HMW bands were detected in culture supernatants of either the K173A or K173R mutants of T3 (JRS4/pJRS9541 or JRS4/pJRS9543, respectively) (FIG. 7, lane 6 and 7). The culture supernatants of all four strains contained a similar pattern of degradation products. The additional band of approximately 65 kDa seen in cell extracts (see above) was also present in supernatants from both the K173A and K173R mutants. From the absence of HMW bands of T3 in both the cell wall and supernatant it is concluded that K173 is essential for polymerization of T3(HA).

Lysine Residue 173 of T3 is Also Required for Attachment of Cpa(Ha) to T3

To identify the lysine in T3 required for the formation of a covalent bond to Cpa(HA), the conserved lysines (FIG. 5) were replaced with alanine using plasmid pEU7646, which encodes Cpa(HA), SipA2, T3 and SrtC2 (FIG. 1). Following confirmation of the induced mutation by sequencing, plasmids were introduced into *E. coli* BL21-CodonPlus(DE3)-RIL, and the formation of T3-T3 homodimer and T3-Cpa heterodimer was analyzed by western blot of whole cell lysates. The monomeric form of Cpa(HA) was identified in an extract from a strain lacking SrtC2 (FIG. 8A lane 1), as before. The Cpa(HA)-T3 heterodimer was present in lysates from T3 mutants K43A, K81A, K100A, K106A, and K191A (FIG. 8A, lanes 3-7), although extracts from mutants K81A and K106A appeared to contain less heterodimer. However, the lysate from mutant K173A showed no heterodimer, while K174A, used as a further control, produced the Cpa(HA)-T3 complex (FIG. 8B). This demonstrates that lysine 173 of T3 is not only required for polymerization of T3, but is also needed for attachment of Cpa(HA) to the T3 shaft protein in *E. coli*.

To demonstrate the role of K173 of T3 in attachment of Cpa to the growing pilus in GAS, the M3 pilus cluster regions from pJRS1325, pEU7646, pEU7687 and pEU7688 (FIG. 1) were cloned into the pReg696-derivative pJRS9508 (Barnett et al. (2007) J Bacteriol 189:1866-73), resulting in plasmids pJRS9554, pJRS9550, pJRS9557 and pJRS9558 respectively. Production of T3 pili by JRS4/pJRS9550 was confirmed by electron microscopy (FIG. 10). A vector control derived from pJRS9508, consisting of the pReg696 backbone and the P23 promoter, was also constructed (pJRS9545). To identify monomeric Cpa(HA) and show its incorporation into the high molecular mass pilus ladder, cell wall extracts of JRS4 with each of these plasmids were prepared, boiled in SDS, and analyzed by western blot using an anti-HA antibody. Since these constructs differ from those used above (FIG. 7) by encoding Cpa(HA) and an untagged version of T3, the same cell wall extracts were also analyzed using an anti-T3 antibody to confirm that in this genetic context K173 is essential for polymerization of T3 and for formation of the T3-Cpa heterodimer in GAS (FIG. 9B). In addition, supernatants of each culture were concentrated 10-fold by TCA precipitation and analyzed by western blot as described above. Strain JRS4/pJRS9554, which lacks srtC2 was used as a control to identify the band corresponding to monomeric T3 (FIG. 9B lanes 2 and 6) and monomeric Cpa(HA) (FIG. 9A lanes 2 and 6). Cell wall extracts and supernatants from strain JRS4/pJRS9550, encoding Cpa(HA), SipA2, T3 and SrtC2, show the HMW forms of the pilus ladder, indicating that Cpa is present in these species (FIG. 9A lanes 3 and 7). Bands corresponding to sizes expected for monomeric Cpa(HA), the Cpa(HA)-T3 heterodimer, the Cpa(HA)-(T3)$^2$ hetero-trimer and the Cpa(HA)-(T3)$^3$ hetero-tetramer are also visible (FIG. 9A lanes 3 and 7). While the Cpa(HA) species mentioned above were also visible in cell wall extracts and supernatants of JRS4/pJRS9558 (T3 K174A) (FIG. 9A, lanes 5 and 9), the cell wall extract and supernatant from strain JRS4/pJRS9557 (T3 K173A) resembled that of the strain lacking SrtC2 (JRS4/pJRS9554): it lacked the prominent bands of the Cpa-T3 heterodimer and higher order polymers observed in the wild type and K174A mutant (compare FIG. 9A lanes 2 and 6 with lanes 4 and 8). Thus, K173 is required for attachment of Cpa to T3 in GAS as well as in *E. coli*.

Cpa(HA) is Located at the Pilus Tip

Next, the position of Cpa(HA) in the T3 pili expressed by GAS was examined using whole-bacteria, negative-stain transmission electron microscopy (EM) coupled with immunogold localization. As expected, strain JRS4 containing the vector-only control plasmid pJRS9545 lacked any detectable pilus fibers (FIG. 10, panel A and D). In contrast, strain JRS4/pJRS9550, encoding Cpa(HA), SipA2, T3, and SrtC2, produced abundant surface fibers (FIG. 10, panels B, C, E, and F). The identity of the surface fibers were identified by incubating the bacteria with anti-T3 rabbit polyclonal antiserum, followed by detection with a secondary anti-rabbit antibody conjugated to 12-nm diameter gold particles. The fibers produced by JRS4/pJRS9550 were abundantly labeled by the gold particles (FIG. 10, panel B and C), whereas only a few stray gold particles were visible on the EM grid with the vector control strain (FIG. 10, panel A). To localize Cpa(HA) in the T3 pili, a dual labeling analysis was performed. For these experiments, the 12-nm gold particles were used to identify T3 pilins, and Cpa(HA) was detected using an anti-HA mouse monoclonal antibody followed by an anti-mouse secondary antibody conjugated to 18-nm diameter gold particles. Dual labeling of the vector control strain again resulted in the presence of only a few, non-specific gold particles (FIG. 10, panel D). However, with strain JRS4/pJRS9550, the larger, HA-specific gold particles could clearly be seen at what appeared to be the tips of some of the pilus fibers labeled by the smaller, T3-specific gold particles (FIG. 10, panels E and F). The EM data suggests that Cpa(HA) can be located at the pilus tips.

Discussion

Motif in the CWSS

Like other proteins covalently linked to the cell wall of Gram-positive bacteria, pilins contain a CWSS at their C termini. Because the enzyme required for pilin polymerization is a member of the sortase family of transpeptidases, it is expected to behave like sortases, which are responsible for covalent attachment of surface proteins to the cell wall. These enzymes recognize the motif at the beginning of the CWSS, usually LPXTG, cleave the substrate protein between the T and G and attach the T residue to an amino group of a second substrate. Unlike all the pilins of the three serologically different *Corynebacterium diphtheriae* pili, as well as pili of *S. pneumoniae, S. agalactiae*, and *Bacillus cereus*, which contain the canonical LPXTG motif, some pilins of Streptococci contain non-canonical motifs in their CWSSs (Scott, J. R. et al. (2006) *Mol. Microbiol*. 62:320-30). For the T3 pilus of GAS, not only is the motif of each of the three pilins that form the pilus non-canonical, but it differs for each of these proteins. Nevertheless, SrtC2 catalyzes both polymerization of T3 and association of the minor pilin, Cpa, with the T3 pilus shaft. It had previously been demonstrated that substitution of the canonical LPSTG motif (SEQ ID NO: 2) for the QVPTG motif (SEQ ID NO: 9) found in the shaft protein, T3, prevents its polymerization (Barnett, T. C. et al. (2004) *J. Bacteriol*. 186:5865-75). The minor pilin, Cpa, has now been examined and it was found that substituting LPSTG (SEQ ID NO: 2) for VPPTG (SEQ ID NO: 10) in this protein prevents its attachment to the shaft protein. In addition, a deletion within the VPPTG motif (SEQ ID NO: 10) in this protein prevents its attachment to the shaft protein, highlighting the necessity of a specific motif at the start of the CWSS for this minor pilin. Thus, it appears that the two different motifs in T3 pilins (XXPTG; SEQ ID NO: 11) are both recognized by SrtC2.

The Second Partner in the Intermolecular Bond Between T3 Subunits

For formation of the peptide bond, the pilin polymerase must recognize a specific motif N-terminal to the CWSS in the second pilin substrate, since the CWSS is cleaved and removed from the pilin. In *C. diphtheriae* SpaA, SpaD and SpaH pilins, Ton-That and Schneewind identified a conserved "pilin motif" WxxxVxVYPK (SEQ ID NO: 97; Ton-That, H. et al. (2003) *Mol. Microbiol.* 50:1429-38) that plays this role. By site-specific mutagenesis, they showed that the K at the end of this motif is required for pilin polymerization, and later demonstrated that this motif, together with the CWSS, is sufficient to cause an unrelated *S. aureus* surface protein to be incorporated into SpaA pili (Ton-That, H. et al. (2004) *Mol. Microbiol.* 53:251-61.).

They suggested, therefore, that the ε-amino group of this K participates in the peptide bond. A similar pilin motif is recognizable in pilins of some other Gram-positive bacteria, but not in all known or putative pilins. It is not present in any of the proteins that constitute GAS pili.

For the GAS T1 major pilin protein, the K that is linked to the T of the CWSS motif of the next T1 subunit was recently identified by structural analysis (Kang, H. J. et al. (2007) *Science* 318:1625-8). The corresponding residue in the homologous T3 pilin is K173, as shown by sequence alignment (FIG. 4). In this work, it was demonstrated that substitution of an A or an R for this residue abrogates T3 polymerization, thus providing biological confirmation of the conclusions of Kang et al. that this bond is required for pilus polymerization.

The presence of two intra-molecular isopeptide bonds within the T1 shaft protein was discovered recently by Kang et al. (Kang, H. J. et al. (2007) *Science* 318:1625-8). Each of these bonds is formed between the ε-amino group of a lysine residue and the carboxyl group of an asparagine (N) residue within the same protein. By site-specific mutagenesis, they demonstrated that a glutamate (E) residue located near each of the two intramolecular bonds is required for formation of this link in a reaction that appears to be spontaneous. Since the wild type T1 protein is more resistant to trypsin digestion than is the mutant protein lacking intramolecular bonds, Kang et al. suggested that the role of the intramolecular bonds might be similar to that of disulfide bonds commonly found in pilins of Gram-negative bacteria i.e. they might stabilize the folded protein and make it more resistant to forces it might encounter in nature. The importance of these intramolecular peptide bonds is suggested by conservation of the residues (KEN) required for their formation in the T1 protein in other pilus backbone proteins (FIG. 5). The MS analysis of the Cpa(HA)-T3 heterodimer (Table 1) identified one of the peptide fragments of T3 formed by an intramolecular isopeptide bond between K191 and N307, as predicted by homology with the T1 protein (Kang et al. (2007) *Science* 318:1625-1628). The inability to identify a peptide containing the second predicted intramolecular bond should not be regarded as significant because the MS coverage of the T3 protein was limited. It was found, however, that substitution of an A for either or both of the K residues predicted to participate in intramolecular bonds does not prevent T3-T3 polymerization or addition of Cpa to T3. Thus, if these K residues are essential for formation of these bonds, then the intramolecular peptide bonds are not required for pilus biogenesis, although they may still play a role in the biological function of the pili.

Linkage of Cpa to T3

Attachment of Cpa to T3 is catalyzed by the same pilin polymerase, SrtC2, as that required for linkage of T3 subunits to each other (3, 43). This enzyme catalyzes formation of a bond between a T in the CWSS and the ε-amino group of a lysine in the next pilus subunit. If linkage of Cpa to T3 proceeds by the same enzymatic mechanism, there are four alternative models of integration of a minor pilin into the pilus structure (FIG. 11), two of which have been proposed previoiusly (Telford et al. (2006) *Nat Rev Microbiol* 4:509-519). It is theoretically possible for Cpa to be located exclusively at the tip of the T3 polymer and for the T in the CWSS motif of Cpa to be linked to the α-amino group of the N-terminal amino acid of T3 (FIG. 11, model A). Because the intact N-terminal peptide of the mature T3 protein in the Cpa-T3 heterodimer was identified in our mass spectrometric analysis, this possibility can be ruled out. It is also possible for the T of the CWSS of T3 to be linked to a K of Cpa. There are two variants of this model. In the one shown in FIG. 11, Model B, Cpa is interspersed within the T3 polymer (a model proposed by Telford et al (2006) *Nat Rev Microbiol* 4:509-519). In the other version of this model (not shown), a minor pilin is anchored directly to the cell wall and forms the base of the pilus, as occurs in GBS and *C. diphtheriae* (Nobbs et al. (2008) *Infect Immun* 76:3550-3560; Mandlik et al. (2008) *Trends Microbiol* 16:33-40). If either variant of Model B were correct for Cpa, the Cpa-T3 heterodimer should still be formed when: (i) the VPPTG (SEQ ID NO: 10) of Cpa is changed (top T3 monomer linked to Cpa in Model B), or (ii) K173 of T3 is mutated to another residue. However, the Cpa-T3 heterodimer for either of these mutations was not seen. Therefore, Model B is unlikely to be correct for Cpa. Model C assumes that Cpa is attached to the T3 polymer by a lysine in T3 different from K173, which links the T3 subunits to each other (FIG. 11, Model C; branched model proposed by Telford et al. (2006) *Nat Rev Microbiol* 4:509-519). In this case, as in Models A and B, K173 of T3 would not be needed to form the Cpa-T3 heterodimer. Since it was found that a K173A mutation of T3 abolished formation of the Cpa-T3 heterodimer, Model C can also be eliminated. The remaining possibility is for the T of the CWSS of Cpa to be linked to T3 by K173 (FIG. 11, model D). This model predicts that mutation of K173 of T3 would prevent formation of the Cpa-T3 heterodimer, which is what was found. Additional support for this model is that replacement of the QVPTG motif (SEQ ID NO: 9) of T3 with LPSTG (SEQ ID NO: 2) did not prevent formation of the dimer with Cpa. In summary, it was found that the same K173 residue that links T3 monomers to each other is required for attachment of Cpa to T3 and the VPPTG motif of Cpa is needed for this attachment, while the QVPTG (SEQ ID NO: 9) of T3 is not required. Thus, model 8D appears to be correct and it appears that Cpa can only be located on the T3 pilus tip.

Localization of Cpa in T3 Pili by Immunogold EM

Model D (FIG. 11) indicates that the minor pilin, Cpa, must be located at the pilus tip. This location was supported by our immunogold EM analysis of the T3 pili expressed by intact GAS bacteria. The electron micrographs indicate that the pilus fibers protrude from the bacterial surface and may well extend beyond the capsule surrounding the GAS strain. The T3 pili appeared as long, thin fibers that tended to twist and bundle together. Dual labeling of the bacteria to detect both the major pilin T3 and minor pilin Cpa demonstrated the presence of Cpa at what appeared to be the pilus tips. This localization was consistently observed, although quantitative analysis of Cpa localization was not possible due to the flexible nature of the pili.

Location of Pilus Adhesin

The tip location of the Cpa minor pilin is similar to that found for the adhesin protein of pili on Gram-negative bacteria that are assembled by the chaperone-usher or alternate chaperone-usher pathways (e.g. Pap and CS1 pili respectively). In these cases, distal location of the adhesin is generally considered to facilitate its interaction with the receptor to which the pilus attaches. However, for GAS, the role of Cpa in adherence of T3 pili or in adherence of the homologus T1 pili is not clear. Abbot et al. (Abbot, E. L. et al. (2007) *Cell Microbiol.* 9:1822-1833) have shown that in a strain producing T1 pili, these pili are required for adherence to primary human keratinocytes or human tonsilar epithelial cells, which are likely to represent the cells to which GAS must attach for initiation of infection. However, in this strain, pili are not needed for attachment to A549 or HEp-2 cells. The Cpa protein of a serotype M49 GAS strain, which has an FCT-3 pilus locus similar to that of the T3 pilus, has been found to bind to type 1 collagen, an important extracellular matrix protein in the human host and to mediate adherence to HEp-2 cells (Kreikemeyer, B. et al. (2005) *J. Biol. Chem.* 280:33228-39). However, for the M1 GAS strain studied by Kehoe's group, collagen binding does not appear to be important for adherence to primary human keratinocytes or human tonsillar epithelial cells, since pre-incubation of either type of human cell with collagen did not affect GAS adherence (Abbot, E. L. et al. (2007) *Cell Microbiol.* 9:1822-1833).

The adhesin for *Streptococcus pneumoniae* (Nelson, A. L. et al. (2007) *Mol. Microbiol.* 66:329-40), *S. agalactiae* (Dramsi, S. et al. (2006). *Mol. Microbiol.* 60:1401-13; Krishnan, V. et al. (2007) *Structure* 15:893-903.) and *C. diphtheriae* (Mandlik, A. et al. (2007) *Mol. Microbiol.* 64:111-24) is a minor pilin protein, encoded by the first gene in the pilus locus, and the pilus shaft protein is dispensable for adherence to the cells studied. In contrast, for the T1 pili of the M1 GAS strain, all three pilin proteins are required for adherence: deletion of the genes for any of the three pilin proteins prevented adherence (Abbot, E. L. et al. (2007) *Cell Microbiol.* 9:1822-1833). However, it is still possible that Cpa is a specific adhesin of T1 and T3 pili, since the shaft protein may be required only to present the adhesin so that it is external to the cell capsule. The role and location of the other minor pilin for T1 or T3 pili has not been investigated yet. It may be interspersed along the shaft of the pilus (Model 8C) as occurs for pilins in *S. agalactiae* (Rosini, R. et al. (2006) *Mol. Microbiol.* 61:126-41) and *S. pneumoniae* (Barocchi, M. A. et al. (2006) *Proc. Natl. Acad. Sci.* 103: 2857-62; Hilleringmann, M., et al. (2008) *PLoS Pathog.* 4:e1000026), or it may be located exclusively at the tip in place of Cpa on some T3 pili. The latter location would produce pili with different specificities on the same bacterial cell.

Comparison with Pili of Gram-Negative Bacteria: Model for Pilus Assembly

Unlike the much larger flagellae in which new subunits are transported through the structure and added at the tip (Macnab, R. M. et al. (2003) *Annu. Rev. Microbiol.* 57:77-100), pili on Gram-negative bacteria grow from the base out. In the well-studied Pap pili, the tip protein is added first and serves to nucleate formation of the pilus structure (reviewed by Sauer, F. G. et al. (2004) *Biochim. Biophys. Acta* 1694: 259-67; Thanassi, D. G. et al. (2005) *Mol. Membr. Biol.* 22:63-72). This is accomplished by the strong affinity of a tip-chaperone complex for the usher protein, which forms a pore in the outer membrane of the Gram-negative cell. Interaction with the usher is proposed to alter the configuration of the tip-chaperone complex so that a shaft subunit can now displace the tip protein from the usher to allow addition of further subunits, leading to continued pilus growth.

Although assembly of pili on Gram-positive bacteria requires a specific pilin polymerase, in both Gram-positive and Gram-negative bacteria, the Sec system is used to transport pilins across the membrane of the cell. It is likely that pili on Gram-positive bacteria also grow by adding new subunits from the bottom because, based on the presence of a predicted membrane-spanning domain, the pilin polymerase is expected to be membrane located. However, the minor pilins are not required to nucleate formation of the pilus structure since they are dispensable for formation of pili in *C. diphtheriae*, *S. agalactiae*, *S. pneumoniae* and GAS. It was found that the minor pilin, Cpa, is likely to be located exclusively at the T3 pilus tip, therefore it must be added first as the pilus grows. In agreement with this idea, Cpa is found in all the HMW bands of growing pili in GAS. Ordered subunit incorporation might be accomplished by a mechanism involving differential affinity, similar to that used for Pap pilus assembly. The membrane-located "gating" protein in Pap pili is the usher, while in Gram-positive bacteria it would be the pilin polymerase. This assembly model predicts that for GAS T3 pili, the polymerase SrtC2 will be found to have a greater affinity for Cpa than for T3. The relative abundance of the Cpa-T3 heterodimer vs. the T3 homodimer in FIG. 3C lane 2 is in agreement with this prediction. When more Cpa becomes available in the cell, growth of a new pilus should be initiated as long as there is an excess of SrtC2 and all other sites and proteins (e.g. SipA2) required. This would lead to limitation of growth of old pili. Thus, regulation of synthesis of the pilin proteins should be important in determining the length and number of pili on the GAS surface.

In summary, the residues required in Cpa and T3 for SrtC2-catalyzed peptide bond formation have been identified. It was also learned that the K residues that appear to be involved in formation of the recently described intramolecular peptide bonds in the shaft protein of the T3 pilus are not required for pilus polymerization, suggesting that the intramolecular peptide bonds are not needed for this process. Finally, because it was found that K173 of T3 is required for addition of Cpa as well as for T3-T3 polymerization, it is likely that Cpa is located exclusively at the tip of the T3 pilus structure.

Materials and Methods for Experimental Example 1

Bacterial Strains and Growth Conditions

GAS strain JRS4 is a spontaneous streptomycin-resistant derivative of the serotype M6 strain D471 (32). GAS strains were grown in Todd-Hewitt medium supplemented with 0.2% yeast extract (Difco). E. coli strains TOP10 (Invitrogen) and BL21-CodonPlus® (DE3)-RIL (Stratagene) were grown in Luria broth (LB) (30). Antibiotics were used in the following concentrations: kanamycin 50 μg/ml and spectinomycin 100 μg/ml. IPTG at a final concentration of 1 mM was used for induction.

Site Specific Mutagenesis

Mutagenesis was performed using the QuikChange II XL mutagenesis Kit (Stratagene) according to the manufacturer's protocol using the primers shown in Table S1. Mutagenized plasmids were transferred into E. coli BL21-CodonPlus® (DE3)-RIL (Stratagene) or TOP10 (Invitrogen). Correct nucleotide replacement was confirmed by DNA sequencing of the mutagenized gene.

Preparation of Cell Lysates and Cell Wall Extracts

Cell lysates of E. coli were obtained from overnight cultures grown with antibiotics and IPTG if appropriate. Samples were prepared from E. coli and GAS as described previously (Zähner, D. et al. (2008) J. Bacteriol. 190:527-35).

Sodium Dodecyl Sulfate Polyacrylamide Gel Electrophoresis (SDS-PAGE) and Immunoblot Analysis Proteins were separated by SDS-PAGE on 4 to 12% gradient gels (NuPAGE®, Invitrogen) and transferred to nitrocellulose membrane (BIORAD) for immunoblot analysis. The monoclonal anti-HA antibody (clone HA-7, Sigma) was used at a 1:2,000 dilution. The polyclonal anti-T3 antiserum, used at a 1:250 dilution is a T3 typing serum provided by Dr. B. Beall (CDC, Atlanta). T3 typing sera have been demonstrated to cross-react with Cpa and other proteins encoded in the FCT region (15).

Immunoprecipitation of Cpa(HA)-T3. E. coli

Top10/pJRS1326 cells were grown to $OD_{600nm}$ of 1.2, and the cell pellet resuspended in 1/50 volume of RIPA buffer (150 mM NaCl, 1.0% Igepal CA-630, 0.5% sodium deoxycholate, 0.1% sodium dodecyl sulfate [SDS], 50 mM Tris; pH 8.0). Cells were disrupted by sonication, and insoluble cell debris was removed by centrifugation at 12,000×g for 15 min at 4° C. Immunoprecipitation of crude cell extracts was performed using "EZview Red Anti-HA Affinity Gel" (Sigma) according to the manufacturer's protocols. The immunoprecipitated protein was subjected to SDS-PAGE on a 4 to 12% gradient gel (NuPAGE®, Invitrogen) followed by visualization with SYPRO® Ruby (Invitrogen) according to the manufacturer's instructions. The band migrating with an apparent molecular weight of 105 kDa, corresponding to the Cpa(HA)-T3 heterodimer was excised, and stored at 4° C. until analysis by mass spectrometry.

Peptide Preparation and Mass Spectrometry

The excised protein band was subjected to trypsin digestion and mass spectrometric analysis (MALDI-TOF-MS/MS analysis) (Medzihradszky, K. F. et al. (2000) Anal. Chem. 72:552-8; Venkataraman, N. et al. (2005) J. Immunol. 175:7560-7) at the microchemical and proteomics facility at Emory University as described previously (Freeman, W. M. et al. (2005) Pharmacogenomics J. 5:203-14; Tseung, C. W. et al. Biochem J. 380:211-8). GPS Explorer 2.0 software (Applied Biosystems) and a MASCOT (www.matrixscience.com/) search engine were used for identification of peptide fragments. The National Center for Biotechnology Information nonredundant database was used for the searches.

Electron Microscopy

For immunogold-EM, S. pyogenes strains JRS4/pJRS9545 (vector control) or JRS4/pJRS9550 (expressing T3 pili with Cpa(HA)) were grown as described above, harvested, washed with PBS, and then adsorbed to polyvinyl formal-carbon-coated grids (E. F. Fullam, Inc.) for 2 minutes and fixed with 1% glutaraldehyde for 1 minute. For single labeling experiments, the grids were washed twice with PBS, blocked with PBS+1% BSA, and then incubated for 1 hour with a 1:200 dilution (in PBS+1% BSA) of the rabbit polyclonal anti-T3 antiserum described above. The grids were washed three times with PBS and then incubated for 1 hour with a 1:50 dilution (in PBS+1% BSA) of anti-rabbit IgG antibody conjugated to 12-nm diameter colloidal gold particles (Sigma-Aldrich). The grids were washed three times with PBS and twice with water, and then negatively stained with 0.5% phosphotungstic acid (Ted Pella, Inc.) for 35 seconds. For dual labeling experiments, grids prepared as described above were then incubated for 1 hour with 1:50 dilutions of both the anti-T3 antiserum and the anti-HA mouse monoclonal antibody described above. The grids were washed three times with PBS and then incubated for 1 hour with 1:50 dilutions of both the 12-nm gold anti-rabbit IgG antiserum and an anti-mouse IgG antibody conjugated to 18 nm diameter colloidal gold particles (Sigma-Aldrich). The grids were then washed and stained as described above. The grids containing the negatively stained bacteria were examined on an FEI TECNAI™ 12 BioTWIN G02 microscope (FEI) at 80 kV accelerating voltage. Digital images were acquired with an AMT XR-60 CCD digital camera system (Advanced Microscopy Techniques).

Table 2 presents information on the primers that were used in these studies.

TABLE 2

Primers used in these experiments[A].

| Primer | SEQ ID NO: | Sequence (5'-3') | Plasmids[B] |
|---|---|---|---|
| Orf100K43A_F | 16 | CCGAAAATGCAAAATTAATAGTAAAAgctACATTTGACTCTTATACAGAC | pEU7646→pEU7652, pEU7657→pEU7678 |
| Orf100K43A_R | 17 | GTCTGTATAAGAGTCAAATGTAgcTTTTACTATTAATTTTGCATTTTCGG | pEU7646→pEU7652, pEU7657→pEU7678 |
| Orf100K81A-F | 18 | CGAAAGACGGTTTAGAGATTGCTCCAGGTATTGTTAATGGTTTAACAG | pEU7646→pEU7651, pEU7657→pEU7679 |
| Orf100K81A-R | 19 | CTGTTAAACCATTAACAATACCTGGAGCAATCTCTAAACCGTCTTTCG | pEU7646→pEU7651, pEU7657→pEU7679 |
| Orf100K100A_F | 20 | CAGCTATACTAATACTGATgcaCAGATAGTAAAGTTAAAAGTACAGAG | pEU7646→pEU7653, pEU7657→pEU7679 |
| Orf100K100A_R | 21 | CTCTGTACTTTTAACTTTACTATCTGGtgcATCAGTATTAGTATAGCTG | pEU7646→pEU7653, pEU7657→pEU7679 |
| Orf100K106A_F | 22 | CTGATAAACCAGATAGTAAAGTTgcaAGTACAGAGTTTGATTTTCAAAAG | pEU7646→pEU7654, pEU7657→pEU7681 |
| Orf100K106A_R | 23 | CTTTTGAAAAATCAAACTCTGTACTtgcAACTTTACTATCTGGTTTATCAG | pEU7646→pEU7654, pEU7657→pEU7681 |
| Orf100K173A_F | 24 | CTAAGGAACAAGGAACAGACGTCgcAAAACCAGTTAATTTTAACAAC | pEU7646→pEU7687, pEU7657→pEU7907 |
| Orf100K173A_R | 25 | GTTGTTAAAATTAACTGGTTTTcgGACGTCTGTTCCTTGTTCCTTAG | pEU7646→pEU7687, pEU7657→pEU7907 |
| Orf100K173R_F | 26 | CTAAGGAACAAGGAACAGACGTCcgAACCAGTTAATTTTAACAAC | pEU7657→pEU7692 |
| Orf100K173R_R | 27 | GTTGTTAAAATTAACTGGTTTTcgGACGTCTGTTCCTTGTTCCTTAG | pEU7657→pEU7692 |
| Orf100K174A_F | 28 | CTAAGGAACAAGGAACAGACGTCAAAgcACCAGTTAATTTTAACAAC | pEU7646→pEU7688, pEU7657→pEU7908 |
| Orf100K174A_R | 29 | GTTGTTAAAATTAACTGGTgcTTTGACGTCTGTTCCTTGTTCCTTAG | pEU7646→pEU7688, pEU7657→pEU7908 |
| Orf100K191A_F | 30 | GCAACTACTTCGTTAAAAGTTAAGgcaAATGTATCGGGGAATACTGG | pEU7646→pEU7661, pEU7657→pEU7682, pEU7678→pEU7909 |
| Orf100K191A_R | 31 | CCAGTATTCCCCGATACATTtgcCTTAACTTTTAACGAAGTAGTTGC | pEU7646→pEU7661, pEU7657→pEU7682, pEU7678→pEU7909 |
| Cpa_LPSTG_Sense | 32 | GAAAACCGAAAAGATCTTcTCCCAtCAACTGGTTTGACAACAGATGG | pEU7646→pEU7904 |
| Cpa_LPSTG_Anti | 33 | CCATCTGTTGTCAAACCAGTTGaTGGGAgAAGATCTTTTCGGTTTTC | pEU7646→pEU7904 |
| T3_LPSTG_Sense | 34 | GTCACAAATAAGCGTGACACTCtACCttCAACTGGTGTTGTAGGCACCCTTGCTCC | pEU7646→pEU7905 |
| T3_LPSTG_Anti | 35 | GGAGCAAGGGTGCCTACAACACCAGTTGaAggTaGAGTGTCACGCTTATTTGTGAC | pEU7646→pEU7905 |
| Cpa_VP1_Sense | 45 | GAAAACCGAAAAGATCTTGTCCCATTGACAACAGATGG | pJRS9550→pJRS9597 |
| Cpa_VP1_Anti | 46 | CCATCTGTTGTCAATGGGACAAGATCTTTTCGGTTTTC | pJRS9550→pJRS9597 |

[A]Uppercase letters represent bases complementary to GAS sequence. Lowercase letters represent bases added or changed to facilitate cloning or mutagenesis.
[B]Templates used in PCR with according primer pairs, and the resulting plasmids.

Example 2. Expression of a Polypeptide Fused to Cpa in *E. coli*

Constructs containing a polynucleotide encoding a fusion protein comprising the maltose binding protein (encoded by the malE gene) and amino acid residues 594-744 of Cpa (SEQ ID NO: 6) were transformed into *E. coli* strain XL10. The fusion protein further comprised an amino-terminal Sec-dependent signal sequence. Constructs used in this study were pJRS9555 (comprises the FCT-3 region from M3 GAS strain AM3 from the MBP/Cpa gene through SrtC2) or pJRS9556 (comprises the same FCT-3 region from M3 GAS strain AM3 from the MBP/Cpa through T3), which are derivatives of the pJRS1326 construct (see FIG. 1). Cell lysates and cell wall extracts were prepared as described in Zähner and Scott (2008) *J Bacteriol* 190:527-535. The extracts were treated with hot SDS to dissociate molecules that are not covalently linked. Immunoblot analysis with an anti-MBP and anti-T3 antibody was performed as described in Experimental Example 1 and results are shown in FIG. 12. Lanes 3, 6, and 7 have the genes needed to link the MBP/Cpa fusion protein to the growing T3 polymer (MBP/Cpa, T3, SipA, and SrtC2). In lanes 3, 6, and 7 MBP/Cpa is covalently linked to T3. Lanes 8, 9, and 10 are negative controls lacking the gene encoding the enzyme that catalyzes this process (SrtC2). Lanes 3, 6, and 7 were confirmed by PCR analysis to have the desired insert; lanes 2, 4, and 5 lack the insert and lanes 8-10 lack srtC2. Therefore, the MBP/Cpa fusion protein can be added to the T3 polymer in *E. coli*.

Example 3. Expression of a Polypeptide Fused to Cpa in *Lactococcus lactis*

A plasmid, referred to herein as pJRS9565, was constructed which comprises the FCT-3 region from the M3 GAS strain AM3 including the Cpa gene, SipA2, T3, and SrtC2 (see FIG. 13), wherein the gene encoding maltose binding protein was inserted within the Cpa gene. The plasmid thus encodes a MBP/Cpa fusion protein which is referred to herein as MBP*. The nucleotide and amino acid sequences of the MBP/Cpa fusion are set forth in SEQ ID NOs: 98 and 99, respectively. The nucleotide sequence comprises 30 nucleotides in the 5' untranslated region of Cpa, followed by the first 56 codons of the coding sequence, the MBP coding sequence, and then the nucleotide sequence encoding amino acid residues 594-744 of Cpa. This construct comprises the coding sequence for the Sec-dependent signal peptide sequence of Cpa (the amino acid sequence is set forth in SEQ ID NO: 100). Once the expressed protein is translocated, the Sec-dependent signal peptide is cleaved, resulting in a MBP/Cpa fusion protein comprising the sequence set forth in amino acids SEQ ID NO: 102. A control plasmid pJRS9566, which lacks SrtC2, was also constructed and used in the following studies.

*Lactococcus lactis* strain MG1363 was transformed with the pJRS9565 or the control pJRS9566 plasmid and the exposure of the MBP* antigen and T3 on the surface of intact MG1363/pJRS9565 was examined by whole cell dot blot with a monoclonal anti-MBP antibody and polyclonal anti-T3 antiserum. The MBP* antigen and T3 are both surface exposed in MG1363/pJRS9565 as demonstrated by reaction with the anti-MBP antibody and anti-T3 antiserum (FIGS. 14A and 14B, lanes 1-4, rows E, F (+)). As expected, MG1363/pJRS9566, which lacks SrtC2, does not react with either of these antibodies (FIGS. 14A and 14B lanes 1-4, row G (−SrtC)).

To examine whether the MBP* antigen is incorporated into HMW polymers characteristic of pili in Gram-positive bacteria (Scott and Zähner (2006) *Mol Microbiol* 62:320-330; Telford et al. (2006) *Nat Rev Microbiol* 4:509-519; Mandlik et al. (2008) *Trends Microbiol* 16:33-40), cell wall fractions of strains MG1363/pJRS9565 (MBP*), MG1363/pJRS9566 (−SrtC2), and MG1363/pJRS9545 (vector control) were prepared and analyzed by western blot with anti-MBP and anti-T3. The MBP*-T3 heterodimer (80 kDa) and the high molecular mass ladder characteristic of pili are seen in cell wall extracts of MG1363/pJRS9565 analyzed with anti-MBP and anti-T3, indicating that MBP* is incorporated into the pilus structure and that T3 pilus polymerization occurs normally (FIGS. 15A and 15B, lanes 1 and 2). As expected, analysis of the cell wall fraction from MG1363/pJRS9566 (SrtC2-) with anti-MBP and anti-T3 shows only the monomeric forms of MBP* and T3, with apparent molecular masses of 57 kDa and 32 kDa respectively (FIGS. 15A and 15B, lane 3). No cross reactivity with either the anti-MBP antibody or the anti-T3 antiserum is observed with the cell wall fraction of MG1363/pJRS9545.

Negative-stain transmission electron microscopy of whole bacteria coupled with immunogold localization (performed using similar methods as those described in Experimental Example 1) reveals that abundant surface fibers are expressed by MG1363/pJRS9565. Analysis with polyclonal anti-T3 antiserum followed by detection with a secondary anti-rabbit gold-conjugate antibody indicates that these fibers are composed of the T3 protein (FIGS. 16A and 16B). As expected, MG1363 containing the vector control does not express pili or react with the T3 antibody (FIG. 16C).

To determine whether MBP* is synthesized in MG1363 in an active form, lysates of MG1363/pJRS9565 and MG1363/pJRS9566 were applied to amylose resin, and the eluate, flow through and crude lysate fractions were analyzed by western blot with the anti-MBP antibody and the anti-T3 antiserum for the presence of HMW pilus polymers. Lysates of MG1363/pJRS9545 treated in the same fashion were used as a negative control. HMW pilus forms are detected by both the anti-MBP antibody and the anti-T3 antiserum in the eluate fraction of MG1363/pJRS9565, indicating that MBP remains active and confers the ability to bind amylose resin to hybrid pili (FIGS. 17A and 17B, lane 2). As expected, only the monomeric form of the MBP* is seen in the eluate fraction of MG1363/pJRS9566 when analyzed in this fashion (FIGS. 17A and 17B, lane 3). No cross reactivity with either the anti-MBP antibody or the anti-T3 antiserum is observed with extracts of MG1363/pJRS9545.

To examine the possibility that the binding of MBP* pili to the amylose resin is nonspecific in nature, lysates of MG1363/pJRS9550, which produces wild type (wt) T3 pili, were purified using the amylose resin and analyzed with anti-MPB and anti-T3 as described above. Duplicate samples corresponding to the elution (E) fraction of MG1363/pJRS9565 and the elution (E), flow through (F) and crude lysate fractions of MG1363/pJRS9550 were transferred to nitrocellulose. The membrane was cut down the middle (slide 10 lane 5) and half was analyzed with monoclonal anti-MBP antibody (FIG. 18, lanes 1-4) while the other half was analyzed with monoclonal anti-HA antibody (FIG. 18, lanes 6-9). As expected, the pili produced by MG1363/pJRS9565 (MBP*) bind to the amylose resin and can be eluted with maltose as HMW forms that react with anti-MBP (FIG. 18, lane 1). In contrast, the pili of MG1363/pJRS9550 do not bind to the amylose beads, and are detected in the flow through and crude lysate fractions using the anti-HA antibody (FIG. 18, lanes 8, 9). These data demonstrate that the binding of hybrid pili to the amylose resin is not a result of interactions between the wild type pilus subunits and the amylose beads, but is rather due to the ability to bind amylose conferred upon hybrid pili by MBP*.

Materials and Methods for Experimental Example 3

Strains, Plasmids and Growth Conditions

*Lactococcus lactis* MG1363 was cultured without shaking at 30° C. in M17 media (OXOID) supplemented with 0.5% glucose (GM17). MG1363 was made competent by the method of Holo and Nes (Holo and Nes (1989) *Appl Environ Microbiol* 55:3119-3123). Spectinomycin was used at a concentration of 100 µg/mL.

Cell Wall Extraction

Cell wall fractions of MG1363 were obtained using a modification of the procedure of Buccato et al. (2006) *J Infect Dis* 194:331-340, as follows. Overnight cultures of MG1363 were centrifuged at 4000 rpm for 10 minutes at 4° C. in an Eppendorf 5810R tabletop centrifuge with an A-4-62 swinging bucket rotor. The pellet was resuspended in ⅒ volume of saline (0.9% m/v NaCl), transferred to a 1.5 mL Eppendorf tube, and centrifuged at 13000 rpm for 1 minute at 4° C. in a Spectrafuge 16M microcentrifuge. The pellet was resuspended in the same volume of saline solution, and the optical density at 600 nm (OD600) was determined at a dilution of 1:100. The concentration of cells in cell units/mL [CU/mL] was calculated as previously described (Biswas et al. (2001) *Infect Immun* 69:7029-7038). Four CU was transferred to a new 1.5 mL tube, and centrifuged as above. Cell wall extraction was performed in 160 µL of lysis buffer (50 mM Tris-HCl 6.8, 30% raffinose, Roche Complete protease inhibitors, 4 mg/mL lysozyme, 400 U/mL mutanolysin) at 37° C. for 3 hours with gentle rotation. Samples were centrifuged at 13000 rpm for 1 minute at room temperature, and the supernatant was transferred to a new tube, and recentrifuged at 13000 rpm for 4 minutes at room temperature. Then, 75 µL of the second supernatant was combined with 25 µL of 4×SDS sample buffer (Sambrook et al., 1989) in a new tube and samples were heated to 100° C. for 10 min.

Dot Blot

Dot blot was performed by a slight modification of the procedure of Biswas et al. (2001) Infect Immun 69:7029-7038. Briefly 5 µL of an overnight culture of MG1363 that had been washed in saline solution as described above, was spotted onto a nitrocellulose membrane (BIO-RAD) and dried for 3 hours at room temperature. Membranes were blocked at room temperature in blocking solution (3% BSA in TBS 7.6, 0.02% NaN3) for 30 minutes with gentle orbital rotation, followed by analysis with the appropriate antibody.

Amylose Purification of Hybrid Pili

Overnight cultures of MG1363 were centrifuged at 4000 rpm at 4° C. for 10 minutes, and the pellets were resuspended in 1/10 volume of saline solution at 4° C. The $OD_{600}$ was used to calculate the number of cell units/mL [CU/mL] as previously described (Biswas et al. (2001) Infect Immun 69:7029-7038). Ten CU were transferred to a sterile 1.5 mL Eppendorf tube and centrifuged at 13000 rpm for 1 minute at 4° C. Samples were incubated in lysis buffer (50 mM Tris-HCl 6.8, Roche Complete protease inhibitors, 4 mg/mL lysozyme, 400 U/mL mutanolysin) for 30 min at 37° C. Samples were then incubated at 4° C. for 10 minutes followed by sonication at 4° C. for 2×15 seconds, with 15 second pauses between sonications. Reactions were centrifuged at 13,000 rpm for 5 minutes at 4° C., and the supernatant was transferred to a new tube and recentrifuged at 4° C. for 10 min at 13000 rpm. A sample of this supernatant, corresponding to crude lysate, was saved for later analysis. The remainder was transferred to a 200 µL slurry volume of amylose resin (New England Biolabs), which had been washed and pre-equilibrated with column wash buffer (20 mM Tris-HCl 7.4, 200 mM NaCl, 1 mM EDTA, 1 mM DTT). Samples were batch purified by incubation at 4° C. for 30 minutes with gentle tapping every 5 minutes. Reactions were then centrifuged at 6000 rpm for 1 min at 4° C. and a sample corresponding to the flow-through fraction was stored for later analysis. The resin was washed with 3×1 mL of column wash buffer at 4° C. with a 1 minute centrifugation at 6000 rpm between washes. Bound protein was eluted in 350 µL column wash buffer containing 25 mM maltose. SDS sample buffer (Sambrook et al., 1989) was added and samples were heated to 100° C. for 10 minutes.

SDS PAGE and Western Blot

SDS PAGE was conducted using NuPAGE 4-12% gradient gels (Invitrogen) with MES running buffer as previously described (Zähner and Scott (2008) J Bacteriol 190: 527-535). Proteins were transferred to nitrocellulose membranes (BIO-RAD) using a BIO-RAD MINI TRANS-BLOT® system with transfer buffer (25 mM Tris 8.3, 192 mM glycine) at a constant voltage of 100V for 1 hour at 4° C. Blocking solution (3% BSA in TBS 7.6, 0.02% NaN3) was used to block membranes and for incubation of primary and secondary antibodies. The polyclonal anti-T3 antiserum was used at a dilution of 1:250. The mouse monoclonal anti-MBP antibody, a product of New England Biolabs, and the mouse monoclonal anti-HA antibody (HA-7), a product of Sigma-Aldrich, were used at dilutions of 1:2,000. Goat anti-mouse and goat anti-rabbit alkaline phosphatase conjugated secondary antibodies (Sigma-Aldrich) were used at a dilution of 1:3000. Signals were detected using a nitrotetrazolium blue (NBT), 5-bromo-4-chloro-3-indolyl phosphate p-toluidine (BCIP) detection system.

Example 4. Intranasal Vaccination of Mice with Lactococcus lactis Expressing the Maltose Binding Protein on the Pilus Tip To determine if the L. lactis bacteria comprising the pJRS9565 plasmid could elicit an immune response to the displayed MBP protein in mice, CD1 mice were vaccinated intranasally with the MG1363/pJRS9565 (encodes MBP*) or the MG1363/pJRS9545 (vector control) bacteria. Blood samples and lung lavage fluids were obtained from the mice. Anti-MBP IgG or IgA antibodies in the fluids were measured using an ELISA. As seen in FIGS. 19 and 20, mice that were vaccinated with the plasmid expressing the MBP-Cpa fusion protein had developed an immune response to the displayed MBP. Therefore, polypeptides displayed on the tips of bacterial pili are effective at mounting an immune response in mice, demonstrating the utility of such methods for the development of vaccines to various antigens.

Materials and Methods for Experimental Example 4

Mouse Immunization

Cells (MG1363/pJRS9545 or MG1363/pJRS9565) grown at 30° C. in M17 with glucose containing 100 µg/ml spectinomycin, were washed and resuspended in PBS to give 5×10$^7$ cfu/ml. Female CD1 mice were vaccinated intranasally by administration of 20 µl of cell suspension (10$^9$ CFU). The mice were vaccinated every 10 days with a dose of 10$^9$ CFU for three consecutive days, (i.e., the animals were vaccinated on days 1, 2, 3, 14, 15, 16, and on days 27, 28, and 29). Blood samples were collected every 10 days (on days 1, 14, 27, and 39). The mice were sacrificed on the 39th day, and lung lavage fluids were obtained post mortem by inserting a nylon cannula into the exposed trachea, which was tied in place. A 1.0 ml syringe was used to inject and withdraw 1 ml of 0.9% sodium chloride solution three times, the supernatants were then stored at −80° C.

ELISA Detection of Antigen-Specific Antibodies in Serum and Lung Lavage

A 96-well EIA/RIA microplate (Costar, Corning Inc.) was coated overnight at 4° C. with 100 ng of MBP per well. The coated plate was blocked with 5% soy milk in PBS-Tween to prevent nonspecific binding. Sera (1:50 dilution) or lung fluid was reacted with the coated wells Antibody production was detected by using anti-mouse IgG or anti-mouse IgA secondary antibodies coupled to alkaline phosphatase (Sigma). Absorbance was measured at 405 nm after 45 min following the addition of p-nitrophenyl phosphate hexahydrate disodium salt (pNPP) tablets dissolved in diethanolamine buffer solution (KPL). The values were corrected for background by subtracting the reading obtained with sera or lung fluid of non-immunized mice.

Example 5. Development of a Live Lactococcus lactis Vaccine

As model epitopes, two different domains of the protective antigen subunit of the anthrax toxin are used to provide protection against Bacillus anthraces. Domain 1' (residues 168-258 of SEQ ID NO: 92), which is the domain that remains at the N-terminus of the toxin following its proteolytic cleavage by proteases ubiquitously present in host tissue is used. This domain, called "LEF domain", is involved in binding to the other subunits of the anthrax toxin, LF (lethal factor), and EF (edematous factor). The second domain used is domain 4 (residues 596-735 of SEQ ID NO: 92), called "RBD", which is responsible for binding of the toxin to host cell receptors. The RBD and LEF domains are antigenic as DNA vaccines, have been inserted into the influenza virus fused within the hemagglutinin protein, and have been shown to provide passive protection against the toxin (Li et al (2005) J Virol 79:10003-10012).

Two other model antigens are used that are likely to be protective against enterotoxigenic *Escherichia coli* (ETEC): a mutant nontoxic form of the heat labile toxin LT, and CooD, an ETEC adhesin.

The following two antigens are used separately to generate vaccines: 1) a triple LT A mutant (whose nucleotide and amino acid sequences are set forth in SEQ ID NOs: 95 and 96, respectively) is constructed (R7K, S63K, V53E) in which three residues required for toxin activity have been changed in ways that don't alter the protein structure (Pizza et al (1994) *J Exp Med* 180:2147-2153); and 2) cooD from a CS1 ETEC strain (whose nucleotide and amino acid sequences are set forth in SEQ ID NOs: 89 and 90, respectively), which will be cloned into the plasmid together with its chaperone gene cooB (Voegele, Sakellaris & Scott (1997) *Proc Natl Acad Sci USA* 94:13257-13261). Using standard recombinant DNA technology, a fusion protein is engineered that has the entire antigenic protein (either LT or CooD) fused to the C terminus of the pilus tip protein (Cpa) in a plasmid that contains all the genes needed to make T3 pili from *S. pyogenes*. Following DNA sequence confirmation of each plasmid construction, western blots are used to show that, in *Escherichia coli*, the guest protein is polymerized with T3. Each plasmid is transformed into signal sequence and a western blot is used to identify the presence of the guest antigen in polymerized pili. Whole cell dot immunoblots is used to confirm surface localization in *L. lactis* of the guest antigen.

Each of the two *L. lactis* strains are introduced intraperitoneally and intranasally into mice. Serum is collected and tested in the ELISA assay for IgG and IgA reactivity with LT or CooD. Mice are sacrificed and IgA assayed in nasal lavage, bronchio-alveolar lavage, and gut lavage fluid.

Upon detection of antibody, the ability of the anti-LT to neutralize toxicity of whole LT-producing ETEC bacteria or anti-CooD to prevent adherence of CS1 ETEC bacteria is determined.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

What we claim:

1. A recombinant nucleic acid encoding a pilus tip fusion protein comprising an antigen fused to a carboxy-terminus of a fragment of Cpa (SEQ ID NO: 101) comprising a cell wall sorting signal (CWSS) motif, wherein the CWSS is VPPTG (SEQ ID NO: 10) and wherein the pilus tip fusion protein comprises an amino-terminal sec-dependent signal sequence.

2. The recombinant nucleic acid of claim 1 wherein the fragment of Cpa comprising the CWSS motif comprises is a polypeptide having at least 50% sequence identity to SEQ ID NO: 101.

3. The recombinant nucleic acid of claim 1 wherein the amino-terminal dec-dependent signal sequence is a polypeptide having at least 40% sequence identity to SEQ ID NO: 100.

4. The recombinant nucleic acid of claim 1 further comprising genes sipA2, tee3, and srtC2.

5. An expression cassette comprising the recombinant nucleic acid of claim 1.

6. A vector comprising the expression cassette of claim 5.

7. The expression cassette of claim 5 further comprising genes sipA2, tee3, and srtC2.

8. A pili expressing bacteria comprising the recombinant nucleic acid of claim 1 and a nucleic acid comprising genes sipA2, tee3, and srtC2, wherein expression of the genes and the pilus tip fusion protein localizes the pilus tip fusion protein to the tip of pili.

9. The recombinant nucleic acid of claim 1 wherein the fragment of Cpa is SEQ ID NO: 4.

* * * * *